(12) United States Patent
Olwill et al.

(10) Patent No.: US 10,703,810 B2
(45) Date of Patent: Jul. 7, 2020

(54) FUSION POLYPEPTIDES WHICH BIND VASCULAR ENDOTHELIAL GROWTH FACTOR A (VEGF-A) AND ANGIOPOIETIN-2 (ANG-2)

(71) Applicant: Pieris Australia Pty Ltd., Sydney (AU)

(72) Inventors: Shane Olwill, Freising (DE); Rachida-Siham Bel Aiba, Munich (DE); Alexander Wiedenmann, Ulm (DE)

(73) Assignee: Pieris Australia Pty Ltd., Sydney (AU)

( * ) Notice: Subject to any disclaimer, the term of this patent is extended or adjusted under 35 U.S.C. 154(b) by 0 days.

(21) Appl. No.: 15/777,340

(22) PCT Filed: Nov. 30, 2016

(86) PCT No.: PCT/AU2016/051168
§ 371 (c)(1),
(2) Date: May 18, 2018

(87) PCT Pub. No.: WO2017/091850
PCT Pub. Date: Jun. 8, 2017

(65) Prior Publication Data
US 2018/0334499 A1 Nov. 22, 2018

(30) Foreign Application Priority Data

Nov. 30, 2015 (EP) .................................... 15197019

(51) Int. Cl.
| | | |
|---|---|---|
| C07K 16/22 | (2006.01) | |
| C07K 14/515 | (2006.01) | |
| C07K 14/475 | (2006.01) | |
| C07K 14/47 | (2006.01) | |
| A61K 39/00 | (2006.01) | |

(52) U.S. Cl.
CPC .............. *C07K 16/22* (2013.01); *C07K 14/47* (2013.01); *C07K 14/475* (2013.01); *C07K 14/515* (2013.01); *A61K 2039/505* (2013.01); *C07K 2317/31* (2013.01); *C07K 2317/565* (2013.01); *C07K 2317/73* (2013.01); *C07K 2317/76* (2013.01); *C07K 2317/90* (2013.01); *C07K 2317/92* (2013.01); *C07K 2318/20* (2013.01); *C07K 2319/00* (2013.01)

(58) Field of Classification Search
CPC ...... C07K 16/22; C07K 14/47; C07K 14/475; C07K 14/515; C07K 2317/31; C07K 2317/565; C07K 2317/73; C07K 2317/76; C07K 2317/90; C07K 2317/92; C07K 2318/20; C07K 2319/00; A61K 2039/505
See application file for complete search history.

(56) References Cited

U.S. PATENT DOCUMENTS

| | | |
|---|---|---|
| 5,728,553 A | 3/1998 | Goodey et al. |
| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | De Sauvage et al. |
| 6,696,245 B2 | 2/2004 | Winter et al. |
| 7,250,297 B1 | 7/2007 | Beste et al. |
| 7,252,998 B2 | 8/2007 | Skerra et al. |
| 9,051,382 B2 | 6/2015 | Trentmann et al. |
| 9,260,492 B2 | 2/2016 | Matschiner et al. |
| 9,549,968 B2 | 1/2017 | Skerra et al. |
| 9,884,898 B2 | 2/2018 | Corvey et al. |

(Continued)

FOREIGN PATENT DOCUMENTS

| | | |
|---|---|---|
| DE | 4417598 A1 | 12/1995 |
| DE | 19641876 A1 | 4/1998 |

(Continued)

OTHER PUBLICATIONS

"Chain a Crystal Structure of Siderocalin (Ngal, Lipocalin 2) Complexed With Trencam-3,2-Hopo, A Cepabactin Analogue," GenBank Accession No. 1X71_A, Sep. 24, 2008.

(Continued)

*Primary Examiner* — Robert S Landsman
(74) *Attorney, Agent, or Firm* — Brian E. Reese; Dana M. Daukss; Choate, Hall & Stewart, LLP

(57) ABSTRACT

The disclosure provides fusion polypeptides comprising a moiety specific for Ang-2 and another for VEGF-A, which fusion polypeptide can be useful for antagonizing Ang-2 and VEGF-A. In a preferred embodiment, the Ang-2-specific moiety is comprised of a human neutrophil gelatinase associated lipocalin (hNGAL) mutein. Such fusion polypeptide can be used in many pharmaceutical applications, for example, as an agent useful to inhibit or reduce angiogenesis. The present disclosure also concerns methods of making the fusion polypeptides described herein as well as compositions comprising such fusion polypeptides. The present disclosure further relates to nucleic acid molecules encoding such fusion polypeptides, their amino acid sequences and to methods for the generation of such fusion polypeptides and nucleic acid molecules. In addition, the application discloses therapeutic and/or diagnostic uses of such fusion polypeptide as well as compositions comprising one or more of such fusion polypeptides.

19 Claims, 7 Drawing Sheets

Figure 1:
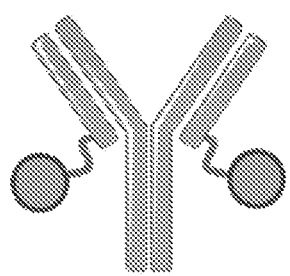
Figure 1:
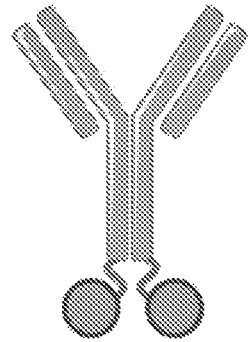
Figure 1:
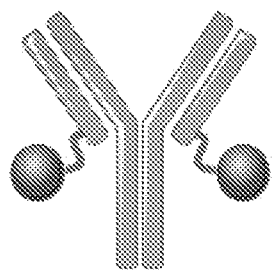
Figure 1:
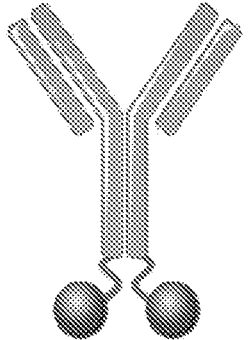

Specification includes a Sequence Listing.

(56) References Cited

U.S. PATENT DOCUMENTS

| | | |
|---|---|---|
| 2003/0069395 A1 | 4/2003 | Sato et al. |
| 2006/0058510 A1 | 3/2006 | Skerra et al. |
| 2006/0088908 A1 | 4/2006 | Skerra et al. |
| 2010/0159587 A1 | 6/2010 | Brinkmann et al. |
| 2013/0079286 A1 | 3/2013 | Skerra et al. |
| 2017/0114109 A1 | 4/2017 | Skerra et al. |
| 2017/0369542 A1 | 12/2017 | Trentmann et al. |
| 2018/0016312 A1 | 1/2018 | Bel Aiba et al. |
| 2018/0141988 A1 | 5/2018 | Hinner et al. |
| 2018/0148484 A1 | 5/2018 | Hinner et al. |

FOREIGN PATENT DOCUMENTS

| | | |
|---|---|---|
| DE | 19742706 A1 | 4/1999 |
| DE | 19926068 C1 | 1/2001 |
| EP | 0 330 451 A2 | 8/1989 |
| EP | 0 361 991 A2 | 4/1990 |
| JP | 2005503829 A | 2/2005 |
| JP | 2007284351 A | 11/2007 |
| WO | WO-96/23879 A1 | 8/1996 |
| WO | WO-98/16873 A1 | 4/1998 |
| WO | WO-99/16873 A1 | 4/1999 |
| WO | WO-99/064016 A1 | 12/1999 |
| WO | WO-00/075308 A1 | 12/2000 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO-2006/056464 A2 | 6/2006 |
| WO | WO-2007/038619 A2 | 4/2007 |
| WO | WO-2009/052390 A1 | 4/2009 |
| WO | WO-2009/156456 A1 | 12/2009 |
| WO | WO-2014/076321 A1 | 5/2014 |

OTHER PUBLICATIONS

Altschul et al., Gapped Blast and PSI-Blast: a new generation of protein database search programs, Nucleic Acids Res., 25(17):3389-3402 (1997).

Altschul, S. et al., Basic Local Alignment Search Tool; J. Mol. Biol., 215:403-410 (1990).

Amstutz, P. et al., In vitro display technologies: novel developments and applications, Curr. Opin. Biotechnol., 2001, 12:400-405.

Bachmann, Barbara J., Linkage Map of Escherichia coli K-12. Edition 8, Microbial. Rev., Jun. 1990, 54(2):130-197.

Beck, et al., Nucleotide Sequence and Genome Organisation of Filamentous Bacteriophages f1 and fd, Gene, vol. 16, pp. 35-58, 1981.

Beste, G. et al., Small antibody-like proteins with prescribed ligand specificities derived from the lipocalin fold, Proc. Natl. Acad. Sci. USA, Mar. 1999, 96:1898-1903.

Bittker, J. et al., Nucleic acid evolution and minimization by nonhomologous random recombination, Nat. Biotechnol., Oct. 2002, 20:1024-1029.

Bos et al., OctoDEX.TM.—Controlled Release of Pharmaceutical Proteins from Hydrogels, Business Briefing: Pharmatech, 2003:1-6.

Breustedt, D. et al., Comparative ligand-binding analysis of ten human lipocalins, Biochim. Biophys. Acta, 2006, 1764:161-173.

Broders, O et al., Hyperphage. Improving antibody presentation in phage display, Methods Mol. Biol., 2003, 205:295-302.

Brody et al., Active and Passive Immunotherapy for Neurodegenerative Disorders, Annu. Rev. Neurosci., 2008, 31:175-193.

Bruckdorfer, T., et al., From Production of Peptides in Milligram Amounts for Research to Multi-Tons Quantities for Drugs of the Future, Curr. Pharm. Biotechnol., 2004, 5:29-43.

Bullock, W. et al., XL1-Blue: A High Efficiency Plasmid Transforming recA Escherichia coli Strain with Beta-Galactosidase Selection, Biotechniques, 1987, 5(4):376-378.

Bundgaard, J.R. et al., Molecular Cloning and Expression of a cDNA Encode NGAL: A Lipocalin Expressed in Human Neutrophils, Biochemical and Biophysical Research Communications, Aug. 15, 1994, pp. 1468-1475, vol. 202, No. 3, XP002036694.

Carnemolla et al., Phage Antibodies with PAN-Species Recognition of the Oncofoetal Angiogenesis Marker Fibronectin ED-B Domain, Int. J. Cancer, 1996, 68:397-405.

Chan et al., The primary structure of rat α 2μ globulin-related protein, Nucleic Acids Research, vol. 16, No. 23, pp. 11368, 1988.

Coles, et al., The Solution Structure and Dynamics of Human Neutrophil Gelatinase-associated Lipocalin, J. Mol. Biol., vol. 289, pp. 139-157, 1999.

Database Geneseq Human mature lipocalin 2 (NGAL) mutant protein L36M. XP002756088, retrieved from EBI accession No. GSP:BBG44509 sequence, Jul. 17, 2014.

Database Geneseq, Human mature NGAL-tear lipocalin mutant fusion protein, SEQ 16., XP002756094, retrieved from EBI accession No. GSP:BBG44294, Database accession No. BBG44294 sequence, Jul. 17, 2014.

Database Geneseq, Human neutrophil gelatinase-associated lipocalin mutein, SEQ ID 2., XP002756089, retrieved from EBI accession No. GSP:AXV25593, Database accession No. AXV25593 sequence, Apr. 1, 2010.

Dennis, M. et al., Albumin Binding as a General Strategy for Improving the Pharmacokinetics of Proteins, J. Biol. Chem., Sep. 20, 2002, 277(38):35035-35043.

Dodel et al., Immunotherapy for Alzheimer's disease, Lancet Neurology, Apr. 2003, 2:215-220.

Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.

Fitzgerald, Kevin, In Vitro Display Technologies—New Tools for Drug Discovery, Reviews, vol. 5, No. 6, pp. 253-258, Jun. 2000.

Fling, S. and Gregerson, D., Peptide and Protein Molecular Weight Determination by Electrophoresis Using a High-Molarity Tris Buffer System without Urea, Anal. Biochem., 1986, 155:83-88.

Flower, Darren R., The lipocalin protein family: structure and function, Biochem. J., 1996, 318:1-14.

Frank, Ronald, The Spot-synthesis technique Synthetic Peptide arrays on membrane supports—principles and applications, J. Immunol. Methods, 2002, 267:13-26.

Fuerteges, F. and Abuchowski, A., The Clinical Efficacy of Poly(Ethylene Glycol)-Modified Proteins,: J. Control. Release, 1990, 11:139-148.

Fujii, Phage display and beyond antibody—molecular target by antibody molecule, Seikagaku, 2010, vol. 82, No. 8, pp. 710-726, Abstract.

Gaillard, P. et al., Diphtheria toxin receptor-targeted brain drug delivery, International Congress Series., 2005, 1277:185-198.

Gaillard, P. et al., Targeted delivery across the blood-brain barrier, Expert Opin Drug Deliv., 2005, 2(2):299-309.

Gasteiger et al., ExPASy: the proteomics server for in-depth protein knowledge and analysis, Nucleic Acids Res., 2003, 31(13):3784-3788.

Goetz, D. et al., Ligand Preference Inferred from the Structure of Neutrophil Gelatinase Associated Lipocalin, Biochemistry, 2000, 39:1935-1941.

Gronwall et al., Selection and characterization of Affibody ligands binding to Alzheimer amyloid β peptides, J. Biotechnol., 2007, 128:162-183.

Haass et al., Soluble protein oligomers in neurodegeneration: lessons from the Alzheimer's amyloid β-peptide, Nat. Rev. Mol. Cell. Biol., Feb. 2007, 8:101-112.

Hansen et al., Effects of angiopoietins-1 and -2 on the receptor tyrosine kinase Tie2 are differentially regulated at the endothelial cell surface, Cellular Signalling, vol. 22, 2010, pp. 527-532.

Hengen, Paul N., Methods and Reagents, Trends Biochem. Sci., vol. 21, pp. 75-76, 1996.

Hoess, Ronald H., Phage Display of Peptides and Protein Domains, Structural Biology, vol. 3, pp. 572-279, 1993.

(56) References Cited

OTHER PUBLICATIONS

Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.
Hortschansky et al., The aggregation Kinetics of Alzheimer's β-amyloid peptide is controlled by stochastic nucleation, Protein Sci., 2005, 14:1753-1759.
Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.
International Search Report and Written Opinion issued in corresponding application No. PCT/EP2016/051657 dated Apr. 8, 2016.
Karlsson et al., Kinetic analysis of monoclonal antibody-antigen interactions with a new biosensor based analytical system, J. Immunol. Methods, 1991, 145:229-240.
Kaspar et al., Fibronectin as target for tumor therapy, Int. J. Cancer, 2006, 118:1331-1339.
Khurana et al., Mechanism of thioflavin T binding to amyloid fibrils, J. Struct. Biol., 2005, 151:229-238.
Kim, H. et al., High-Affinity Recognition of Lanthanide(III) Chelate Complexes by a Reprogrammed Human Lipocalin 2, J. Am. Chem. Soc., 2009, 131:3565-3576.
Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. and Skerra, A., Use of an albumin-binding domain for the selective immobilization of recombinant capture antibody fragments on ELISA plates, J. Immunol. Methods, 1998, 218:73-83.
Korean Office Action issued in corresponding application No. 10-2012-7017730 dated Jul. 28, 2018 with English translation.
Kraulis, et al., The Serum Albumin-Binding Domain of *Streptococcal* Protein G is a Three-Helical Bundle: A Heteronuclear NMR Study, FEBS Letters, vol. 378, pp. 190-194, 1996.
Leahy et al., Crystallization of a Fragment of Human Fibronectin: Introduction of Methionine by Site-Directed Mutagenesis to Allow Phasing via Selenomethionine, Proteins, 1994, 19:48-54.
Lichtlen et al., Antibody-based approaches in Alzheimer's research: safety, pharmacokinetics, metabolism, and analytical tools, J. Neurochem., 2007, 104:859-874.
Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.
Murakami, H. et al., Random insertion and deletion of arbitrary number of bases for codon-based random mutation of DNAs, Nat. Biotechnol., Jan. 2002, 20:76-81.
Notice of Reasons for Rejections dated Jan. 20, 2015 issued in Japanese Application No. 2012-542505, with English translation.
Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.
Paine et al., The Lipocalin website, Elsevier Science B.V., Biochimica et Biophysica Acta 1482, pp. 351-352, 2000.

Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between α1-Acid Glycoprotein and Serum Retinol-Binding Protein and Its Relatives, 1987, The FASEB journal 1.3 (1987): 209-214.
Pini et al., Design and Use of a Phage Display Library, J. Biol. Chem., Aug. 21, 1998, 273(34):21769-21776.
Pini, A. et al., Phage Display and Colony Filter Screening for High-Throughput Selection of Antibody Libraries, Comb. Chem. High Throughput Screen., 2002, 5:503-510.
Pujuguet et al., Expression of Fibronectin ED-A+ and ED-B+ Isoforms by Human and Experimental Colorectal Cancer, Am. J. Pathol., Feb. 1996, 148(2):579-592.
Redl, Bernhard, Human tear lipocalin, Biochim. Biophys. Acta, 2000, 1482:241-248.
Roberts, Richard W., Totally In Vitro Protein Selection Using mRNA-Protein Fusions and Ribosome Display, Current Opinion in Chemical Biology, vol. 3, pp. 268-273, 1999.
Rodi, D. and Makowski, L., Phage-display technology—finding a needle in a vast molecular haystack, Curr. Opin. Biotechnol., 1999, 10:87-93.
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. et al., A Novel Type of Receptor Protein, Based on the Lipocalin Scaffold, with Specificity for Digoxigenin, J. Mol. Biol., 2000, 297:1105-1120.
Schliemann et al., Antibody-based targeting of the tumor vasculature, Biochim. Biophys. Acta, 2007, 1776:175-192.
Schmidt et al., The Strep-tag system for one-step purification and high-affinity detection of capturing of proteins, Nat. Protoc., 2007, 2(6):1528-1535.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Schonfeld, D. et al. An engineered lipocalin specific for CTLA-4 reveals a combining site with structural and conformational features similar to antibodies, PNAS, 106(20): 8198-8203 (2009).
Skerra et al., 'Anticalins': a new class of engineered ligand-binding proteins with antibody-like properties, Reviews in Molecular Biotechnology, 2001, 74:257-275.
Skerra, A., et al., Lipocalins as a scaffold, Elsevier Science B.V., Biochimica et Biophysica Acta 1482, pp. 337-350, 2000.
Skerra, Anticalins as alternative binding proteins for therapeutic use; Current Opinion in Molecular Therapeutics, 9(4): 336-344 (Aug. 2007).
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.
Vajo, Z. and Duckworth, W., Genetically Engineered Insulin Analogs: Diabetes in the New Millennium, Pharmacol. Rev., 2000, 52(1):1-9.

(56) References Cited

OTHER PUBLICATIONS

Venturi, M. et al., High Level Production of Functional Antibody Fab Fragments in an Oxidizing Bacterial Cytoplasm, J. Mol. Biol., 2002, 315:1-8.

Virnekas et al., Trinucleotide phosphoramidites: ideal reagents for the synthesis of mixed oligonucleotides for random mutagenesis, Nucleic Acids Res, 1994, 22(25):5600-5607.

Vogt, M. and Skerra, A., Construction of an Artificial Receptor Protein ("Anticalin") Based on the Human Apolipoprotein D, ChemBioChem, 5: 191-199 (2004).

Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.

Wang et al., Expanding the Genetic Code of *Escherichia coli*, Science, Apr. 20, 2001, 292:498-500.

Wang et al., Expanding the genetic code, Chem. Comm., 2002, 1:1-11.

Wang, A. M. et al., Molecular Cloning of the Complementary DNA for Human Tumor Necrosis Factor, Science, vol. 228, pp. 149-154, 1985 (Abstract).

Wells, J. et al., Rapid Evolution of Peptide and Protein Binding Properties In Vitro, Current Opinion in Structural Biology, vol. 2, pp. 597-604, 1992.

Wilson, D. et al., The use of mRNA display to select high-affinity protein-binding peptides, Proc. Natl. Acad. Sci. USA, Mar. 27, 2001, 98(7):3750-3755.

Yanisch-Perron, C. et al., Improved M13 phage cloning vectors and host strains: nucleotide sequences of the M13mp18 and pUC19 vectors, Gene, 1985, 33:103-119.

Zaccolo, M.et al., An Approach to Random Mutagenesis of DNA Using Mixtures of Triphosphate Derivatives of Nucleoside Analogues, J. Mal. Biol., 1996, 255:589-603.

Zardi, L. et al., Transformed human cells produce a new fibronectin isoform by preferential alternative splicing of a previously unobserved exon, EMBO J, 6(8):2337-42 (1987).

SEQ ID NO's: 8 and 11

SEQ ID NO's: 9 and 10

SEQ ID NO's: 8 and 15

SEQ ID NO's: 9 and 14

FUSION POLYPEPTIDES WHICH BIND VASCULAR ENDOTHELIAL GROWTH FACTOR A (VEGF-A) AND ANGIOPOIETIN-2 (ANG-2)

CROSS-REFERENCE TO RELATED APPLICATIONS

This application is a U.S. National Stage application which claims priority to the international PCT Application No. PCT/AU2016/051168, filed on Nov. 30, 2016, which claims priority to the EP Application No. 15197019.1, filed Nov. 30, 2015, each of which are hereby incorporated by reference in their entirety.

I. BACKGROUND

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular diseases, arthritis, and psoriasis, the process can go awry. (Folkman, J., Nat. Med., 1:27-31 (1995).) There are a number of diseases known to be associated with deregulated or undesired angiogenesis. Such diseases include, but are not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid (or hematopoietic) tumors (such as leukemias and lymphomas). Other diseases associated with undesired angiogenesis will be apparent to those skilled in the art.

Although many signal transduction systems have been implicated in the regulation of angiogenesis, one of the best-characterized and most endothelial cell-selective systems involves the Tie-2 receptor tyrosine kinase that is selectively expressed within the vascular endothelium (referred to as "Tie-2" or "Tie-2R" (also referred to as "ORK"), murine Tie-2 is also referred to as "tek") and its ligands, the angiopoietins (Yancopoulos, G. D., et al., Nature 407:242-48 (2000); Gale, N. W. and Yancopoulos, G. D., Genes Dev. 13:1055-1066 (1999)).

There are four known angiopoietins; angiopoietin-1 ("Ang-1," alternatively abbreviated as ANGPT1 or Ang1) through angiopoietin-4 ("Ang-4"). These angiopoietins are also referred to as "Tie-2 ligands" (Davis, S., et al., Cell, § 7:1161-1169 (1996); Grosios, K., et al., Cytogenet Cell Genet, § 4:118-120 (1999); Holash, J., et al., Investigative Ophthalmology & Visual Science, 42:1611-1625 (1999); Koblizek, T. I., et al., Current Biology, S:529-532 (1998); Lin, P., et al., Proc Natl Acad Sci USA, 95:8829-8834 (1998); Maisonpierre, P. C., et al., Science, 277:55-60 (1997); Papapetropoulos, A., et al., Lab Invest, 79:213-223 (1999); Sato, T. N., et al., Nature, 375:70-74 (1998); Shyu, K. G., et al., Circulation, 95:2081-12087 (1998); Suri, C, et al., Cell, 37:1171-1180 (1996); Suri, C., et al., Science, 252:468-471 (1998); Valenzuela, D. M., et al., Proc Natl Acad Sci USA, 96:1904-1909 (1999); Witzenbichler, B., et al., J Biol Chem, 273:18514-18521 (1998)).

Both Ang-1 and -2 bind to Tie-2 with an affinity of 3 nM ($K_d$) (Maisonpierre, P. C., et al., Science 277 (1997) 55-60). Whereas Ang-1 binding to Tie-2 stimulates receptor phosphorylation in cultured endothelial cells, Ang-2 has been observed to both agonize and antagonize Tie-2 receptor phosphorylation (Davis, S., et al., (1996), supra; Maisonpierre, P. C., et al., (1997), supra; Kim, I, J. H. Kim, et al., Oncogene 19(39): 4549-4552 (2000); Teichert-Kuliszewska, K., P. C. Maisonpierre, et al., Cardiovascular Research 49(3): 659-70 (2001)). The phenotypes of mouse Tie-2 and Ang-1 knockouts are similar and suggest that Ang-1-stimulated Tie-2 phosphorylation mediates remodeling and stabilization of developing vessels in utero through maintenance of endothelial cell-support cell adhesion (Dumont, D. J., et al., Genes & Development, 8:1897-1909 [1994]; Sato, T. N., et al., Nature, 376:10-14 (1995); Suri, C, et al., (1996), supra). The role of Ang-1 in vessel stabilization is thought to be conserved in the adult, where it is expressed widely and constitutively (Hanahan, D., Science, 277:48-50 (1997); Zagzag, D., et al., Experimental Neurology, 59:391-400 (1999)). In contrast, Ang-2 expression is primarily limited to sites of vascular remodeling, where it is thought to block Ang-1 function, thereby inducing a state of vascular plasticity conducive to angiogenesis (Hanahan, D., (1997), supra; Holash, J., et al., Science, 284:1994-1998 (1999); Maisonpierre, P. C, et al., (1997), supra).

Human angiopoietin-2 ("Ang-2," alternatively abbreviated as ANGPT2 or Ang2) is described in Maisonpierre, P. C., et al., Science 277 (1997) 55-60 and Cheung, A. H., et al., Genomics 48 (1998) 389-91. Numerous published studies have purportedly demonstrated vessel-selective Ang-2 expression in disease states associated with deregulated angiogenesis (Bunone, G., et al., American Journal of Pathology, 155:1961-1916 (1999); Etoh, T., et al., Cancer Research, 67:2145-2153 (2001); Hangai, M., et al., Investigative Ophthalmology & Visual Science, 42:1611-1625 (2001); Holash, J., et al., (1999) supra; Kuroda, K., et al., Journal of Investigative Dermatology, 116:113-120 (2001); Otani, A., et al., Investigative Ophthalmology & Visual Science, 40:1912-1920 (1999); Stratmann, A., et al., American Journal of Pathology, 153: 1459-1466 (1998); Tanaka, S., et al., J Clin Invest, 203:34-345 (1999); Yoshida, Y., et al., International Journal of Oncology, 25:1221-1225 (1999); Yuan, K., et al., Journal of Periodontal Research, 35:165-171 (2000); Zagzag, D., et al., (1999) supra). An effective anti-Ang-2 therapy will benefit a vast population of patients with angiogenesis-associated diseases, such as cancer, retinopathies, arthritis, and psoriasis.

A prominent factor also involved in physiological angiogenesis and various diseases and disorders associated with deregulated angiogenesis, for example solid tumor growth, is the vascular endothelial growth factor VEGF-A (also known as VEGF) (Ferrara, Nature (2005) 438, 967-974). Indeed, experiments with neutralizing antibodies and other inhibitors have shown that blockade of the VEGF-A pathway can be sufficient to significantly suppress the angiogenesis associated with tumor growth in many models (Willett, Cancer Cell (2007) 10(2), 145-147; Batchelor, Cancer Cell (2007) 11(1), 83-95) and many therapies targeting this factor have been successful as vascular normalization agents in patients suffering from various conditions arising from pathological angiogenesis, including neovascular age-related macular degeneration (nAMD) (Rosenfeld, N Engl J Med (2006) 355(14), 1419-1431; Trichonas G, Ophtalmol Ther (2013) 2(2), 89-98; Martin, N Engl J Med (2011) 364(2), 1897-1908; Solomon, Cochrane Database Syst Rev (2013) 8, Art.No.:CD005139).

However, recent research on targeted VEGF blockade therapy has revealed that such therapies may promote a more invasive cellular phenotype and enhance tumor cell dissemination (Casanovas, Cancer Cell (2005) 8(4), 299-309; Pae-Ribes, Cancer Cell (2009) 15, 220-231). One theory that accounts for this effect relies on the severe restriction of the oxygen supply to the tumor that occurs when anti-angiogenic agents are used, creating a state of hypoxia. Hypoxia can lead to the transcriptional activation of a number of genes through the stabilization of the HIF-1α transcription factor, which, in the presence of oxygen, is earmarked for proteosomal destruction by oxygen-dependent prolyl-hydroxylases. Targeted genes for activation include VEGF-A, itself, which would, in a normal situation, promote angiogenesis in order to overcome the hypoxia. It has also been reported that Ang-2's expression can be induced by VEGF-A under hypoxic conditions, and may thus further contribute to destabilising vessels in the process of physiological or pathological angiogenesis (Simon, J Cell Physiol (2008) 217(3), 809-818).

More recently, a functional link has been further drawn between Ang-2 and VEGF-A when it was proposed that Ang-2 could be responsible for compensatory tumor revascularization and growth during anti-VEGF therapy and was shown to interfere with anti-VEGFR-2-induced vessel normalization (Bullock, J Clin Oncol (2010) 28, abstr 4630). Data also support a complementary mode of action of antagonists of Ang-2 and VEGF in the context preventing tumor angiogenesis and growth (Hashizume, Cancer Res (2010) 70, 2213-2223).

Given the overlapping and compensatory modes of action of key angiogenic factors with high therapeutic potential such as Ang-2 and VEGF-A, the clinical potential of current monotherapies is clearly limited (Bergers, Nat Rev Cancer (2008) 8, 592-603). Indeed, pre-clinical data recently showed that the simultaneous block of both factors result in enhanced antitumor, antiangiogenic and antimetastatic activity when compared to that of certain monospecific agents used alone (Kienast, Clin Cancer Res (2013) 19(24), 6730-6740). In this context, there is a clear need for the development of potent, dual targeting agents such as the polypeptide disclosed herein.

The present invention satisfies this need and provides anti VEGF-A/Ang2 bispecific therapeutic proteins. Current bispecific antibodies specific for VEGF-A and Ang-2 are, however, sub-optimal, being limited, e.g., by monovalency and geometry, which can impact target engagement and efficacy, not to mention having a relatively high molecular weight of approximately 150 kDa. The present disclosure overcomes these and other limitations by providing novel bi- and multi-specific fusion polypeptides that are at least bivalent for each of the desired therapeutic targets and have unique geometry for improved target engagement.

II. DEFINITIONS

The following list defines terms, phrases, and abbreviations used throughout the instant specification. All terms listed and defined herein are intended to encompass all grammatical forms.

As used herein, "Ang-1", unless specified as being from a non-human species (e.g., "mouse Ang-1," "monkey Ang-1," etc.), means human Ang-1, a full-length protein defined by Swiss Prot Q15389 or a biologically active fragment thereof (e.g., a fragment of the Ang-1 protein which is capable of inducing angiogenesis in vitro or in vivo).

Figure 6:
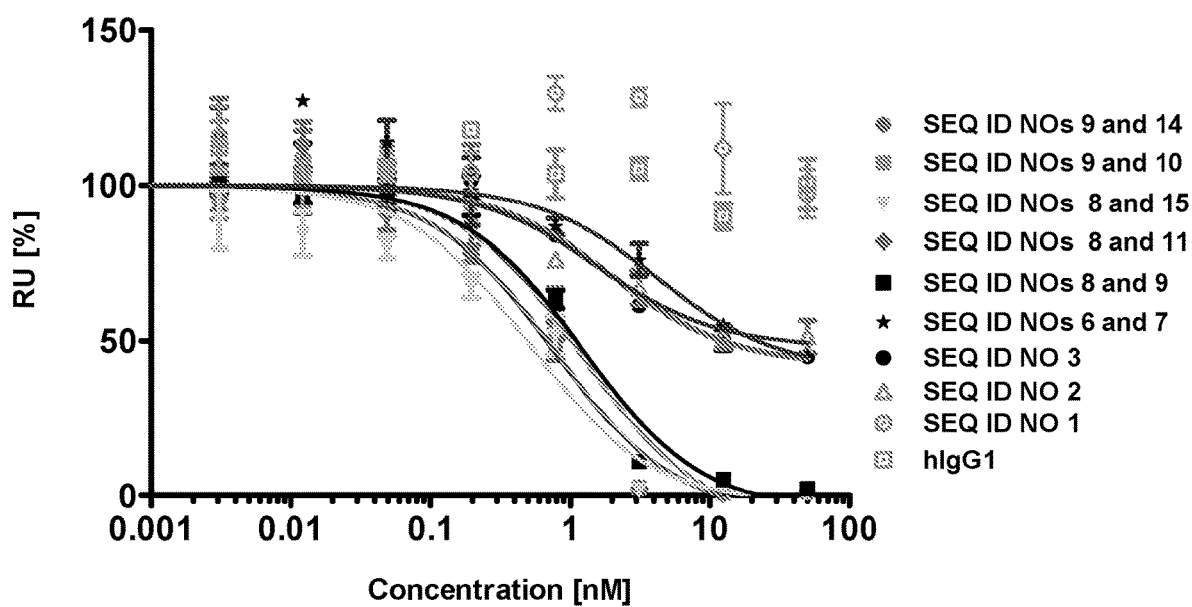

As used herein, "Ang-2", unless specified as being from a non-human species (e.g., "mouse Ang-2," "monkey Ang-2," etc.), means human Ang-2, a full-length protein defined by Swiss Prot O15123, (also see, FIG. 6 of U.S. Pat. No. 6,166,185; incorporated herein by reference in its entirety) or a biologically active fragment thereof (e.g., a fragment of the Ang-2 protein which is capable of inducing angiogenesis in vitro or in vivo).

The term "Tie-2" (also referred to in the art as "tek") unless specified as being from a non-human species (e.g., "mouse Tie-2," "monkey Tie-2," etc.), refers to human Tie-2 or a biologically active fragment thereof. Human Tie-2 has the amino acid sequence as set forth in the NCBI protein sequence database under Accession No. AAA61130.

As used herein, "VEGF-A" may be the human protein with the amino acid sequence of Swiss Prot Data Bank Accession No. P15692, the hamster protein with the amino acid sequence of Swiss Prot Data Bank Accession No. Q99PS1, the bovine protein with the amino acid sequence of Swiss Prot Data Bank Accession No. P15691, the pig protein with the amino acid sequence of Swiss Prot Data Bank No. P49151, the horse protein with the amino acid sequence of Swiss Prot Data Bank Accession No. Q9GKR0, the sheep protein with the amino acid sequence of Swiss Prot Data Bank Accession No. P50412, the mouse protein with the amino acid sequence of Swiss Prot Data Bank Accession No. Q00731, the rat protein with the amino acid sequence of Swiss Prot Data Bank Accession No. P16612, the chicken protein with the amino acid sequence of Swiss Prot Data Bank Accession No. P67964, the guinea pig protein with the amino acid sequence of Swiss Prot Data Bank Accession No. P26617, or of a fragment of the respective protein. The term "VEGF" as mentioned herein includes VEGF-A, VEGF-B, VEGF-C, VEGF-D and/or PLGF. Examples of VEGF proteins are described herein. Preferably, said term, when used in the context of the disclosure and in particular when used in the context of one of the lipocalin muteins of the disclosed combination, refers to VEGF-A. The term "VEGF" thus includes full-length VEGF, but also includes fragments of VEGF, preferably of VEGF-A, and/or variants such as splice variants of VEGF, preferably VEGF-A. Preferably, said fragments or variants are functional, i.e., they have VEGF, preferably VEGF-A activity/function as described herein. Accordingly, when one of the lipocalin muteins of the disclosed combination is referred to as being specific to VEGF, it means that such lipocalin mutein can bind VEGF, preferably VEGF-A, (a) fragment(s) of VEGF, preferably VEGF-A and/or (a) variant(s) of VEGF-A, preferably VEGF-A.

As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of human lipocalin 2) to a selected target (in the present case, Ang-1 or Ang-2), can be measured (and thereby $K_d$ values of a mutein-ligand complex be determined) by a multitude of methods known to those skilled in the art. Such methods include, but are not limited to, fluorescence titration, direct ELISA, competition ELISA, calorimetric methods, such as isothermal titration calorimetry (ITC), and surface plasmon resonance (Biacore). Such methods are well established in the art and examples thereof are also detailed below.

It is also noted that the complex formation between the respective binder and its ligands is influenced by many different factors such as the concentrations of the respective binding partners, the presence of competitors, pH and the ionic strength of the buffer system used, and the experimental method used for determination of the dissociation constant $K_d$ (for example fluorescence titration, direct ELISA, competition ELISA or surface plasmon resonance, just to name a few) or even the mathematical algorithm which is used for evaluation of the experimental data.

Therefore, it is also clear to the skilled person that the $K_d$ values (dissociation constant of the complex formed between the respective binder and its target/ligand) may vary within a certain experimental range, depending on the method and experimental setup that is used for determining the affinity of a particular mutein for a given ligand. This means that there may be a slight deviation in the measured $K_d$ values or a tolerance range depending, for example, on whether the $K_d$ value was determined by surface plasmon resonance (Biacore), by competition ELISA, or by "direct ELISA."

As used herein, a compound such as a mutein of the disclosure "specifically binds" a target (for example, Ang-1 or Ang-2) or has "binding specificity" for a target if it is able to discriminate between that target and one or more reference targets, since binding specificity is not an absolute, but a relative property. "Specific binding" can be determined, for example, in accordance with Western blots, ELISA-, RIA-, ECL-, IRMA-tests, IHC and peptide scans.

The term "human lipocalin 2" or "human Lcn 2" or "human NGAL" or "hNGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 1 is used as reference sequence.

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. The term "mutein," as used herein, also includes its functional fragments or variants. Fragments or variants of particular muteins described in the present disclosure preferably retain the function of binding to Ang-1 or Ang-2, e.g. with detectable or even higher affinity, and such fragments or variants are "functional fragments or variants" of the reference muteins disclosed herein.

The term "fragment" as used herein in connection with the lipocalin muteins of the disclosure relates to proteins or peptides derived from full-length mature human lipocalin 2 that are N-terminally and/or C-terminally shortened, i.e. lacking at least one of the N-terminal and/or C-terminal amino acids. Such fragments may include at least 10 or more such as 20 or more or 30 or more consecutive amino acids of the primary sequence of the mature human lipocalin 2 and are usually detectable in an immunoassay of the mature human lipocalin 2. Such a fragment may lack up to 2, up to 3, up to 4, up to 5, up to 10, up to 15, up to 20, up to 25, or up to 30 (including all numbers in between) of the N-terminal and/or C-terminal amino acids. It is understood that the fragment is preferably a functional fragment of the full-length mature human lipocalin 2 (mutein), which means that it preferably comprises the binding pocket of the full length mature human lipocalin 2 (mutein) it is derived from. As an illustrative example, such a functional fragment may comprise at least amino acids 28-134, preferably at least amino acids 13-157 of the linear polypeptide sequence of the full length mature human lipocalin 2.

In general, the term "fragment", as used herein with respect to the corresponding protein ligand of a mutein of the disclosure or of the combination according to the disclosure, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature human lipocalin 2 can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the disclosure.

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any mutein of the disclosure).

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a mutein different from the wild-type human lipocalin 2 corresponds to a certain position in the amino acid sequence of the wild-type human lipocalin 2, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, the wild-type human lipocalin 2 can serve as "subject sequence" or "reference sequence", while the amino acid sequence of a mutein different from the wild-type human lipocalin 2 described herein serves as "query sequence". The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By a "native sequence" human lipocalin 2 is meant human lipocalin 2 that has the same amino acid sequence as the corresponding polypeptide derived from nature. Thus, a native sequence human lipocalin 2 can have the amino acid sequence of the respective naturally-occurring human lipocalin 2. Such native sequence polypeptide can be isolated from nature or can be produced by recombinant or synthetic means. The term "native sequence" polypeptide specifically encompasses naturally-occurring truncated or secreted forms of the human lipocalin 2, naturally-occurring variant forms such as alternatively spliced forms and naturally-occurring allelic variants of human lipocalin 2. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally, a variant has at least about 70%, including at least about 80%, such as at least about 85% amino acid sequence identity, including at least about 90% amino acid sequence identity or at least about 95% amino acid sequence identity with the native sequence polypeptide.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) human lipocalin 2. Similarly, the position of a given nucleotide in accordance with the present disclosure which may be substituted may vary due to deletions or additional nucleotides elsewhere in a mutein or wild type human lipocalin 2 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a mutein based on a reference scaffold in accordance with the disclosure, it is preferably to be understood that the positions of nucleotides/amino acids are structurally corresponding to the positions elsewhere in a mutein or wild-type human lipocalin 2, even if they may differ in the indicated number.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

The term "metastasis" according to the disclosure refers to the transmission of cancerous cells from the primary tumor to one or more sites elsewhere in a patient where secondary tumors develop. Means to determine if a cancer has metastasized are known in the art and include bone scan, chest X-ray, CAT scan, MRI scan, and tumor marker tests. The term "prevention of metastasis" means that the metastasis of the primary, tumor or cancer is prevented, delayed, or reduced and thus the development of secondary tumors is prevented, delayed, or reduced. Preferably the metastasis i.e. secondary tumors of the lung are prevented or reduced, which means that metastatic transmission of cancerous cells from the primary tumor to the lung is prevented or reduced.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the oesophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "vascular diseases" includes Cancer, Inflammatory diseases, Atherosclerosis, Ischemia, Trauma, Sepsis, COPD, Asthma, Diabetes, AMD, Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes (such as proliferative retinopathies or age-related macular degeneration (AMD)), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A., Vascular diseases, In: Pathobiology of ocular disease, A dynamic approach, Garner, A., and Klintworth, G. K. (eds.), 2nd edition, Marcel Dekker, New York (1994), pp 1625-1710).

The term "antibody", as used herein, is intended to refer to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hyper variability, termed complementarity determining regions (CDRs), interspersed with regions that are more conserved, termed framework regions (FR). Each $V_H$ and $V_1$ is composed of three CDRs and four FRs, arranged from amino-terminus to carboxyl-terminus in the following order: FR1, CDR1, FR2, CDR2, FR3, CDR3, FR4. In different embodiments of the disclosure, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs. CDR sequences can be easily determined based on the sequences of the light chain and/or heavy chain variable regions. The preferred method in the context of the invention is the IMGT method as described in Lefranc, M.-P., The Immunologist, 7, 132-136 (1999). CDR1 consists of positions 27 to 38, CDR2 consists of positions 56 to 65, CDR3 for germline V-genes consists of positions 105 to 116, CDR3 for rearranged V-J-genes or V-D-J-genes consists of positions 105 to 117 (position preceding J-PHE or J-TRP 118) with gaps at the top of the loop for rearranged CDR3-IMGT with less than 13 amino acids, or with additional positions 112.1, 111.1, 112.2, 111.2, etc. for rearranged CDR3-IMGT with more than 13 amino acids. The positions given in this paragraph are according to the IMGT numbering described in Lefranc, M.-P., The Immunologist, 7, 132-136 (1999).

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

III. DESCRIPTIONS OF FIGURES

FIG. 1: provides an overview of the design of the representative fusion polypeptides described in this application, which are bispecific with regard to the targets VEGF-A and Ang-2. Representative fusion polypeptides were made based on an antibody specific for VEGF-A (SEQ ID NOs: 8 and 9) and a lipocalin mutein specific for Ang-2 (SEQ ID NO: 2 or SEQ ID NO: 3). Lipocalin muteins were fused to either one of the two C-termini of the antibody. The resulting fusion polypeptides have the SEQ ID NOs: 9 and 10, SEQ ID NOs: 8 and 11, SEQ ID NOs: 9 and 14, SEQ ID NOs: 8 and 15.

Figure 2:
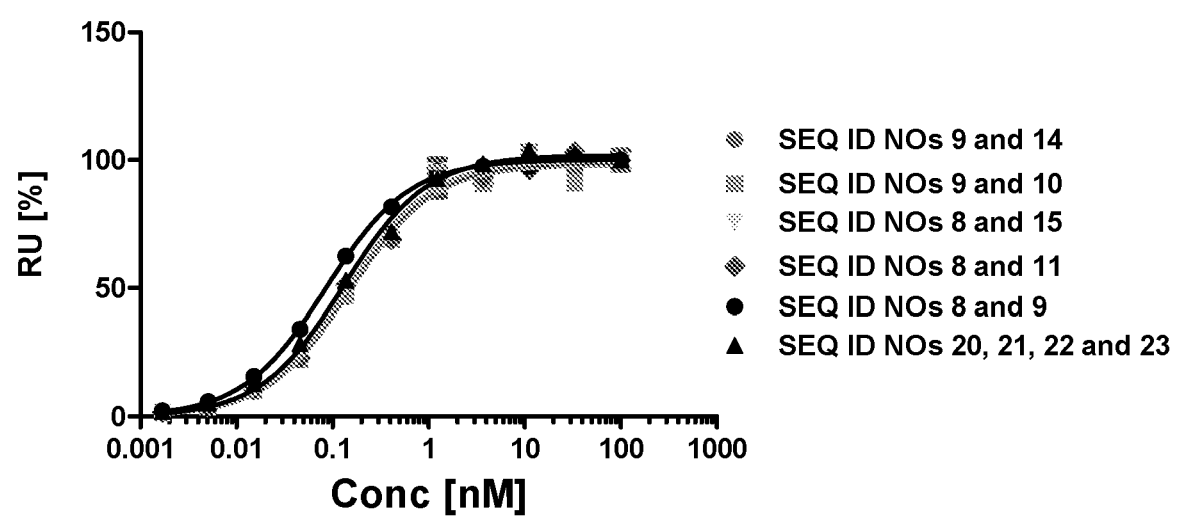

FIG. 2: depicts the results of ELISA experiments in which the affinity of representative fusion polypeptides, the benchmark bispecific antibody (SEQ ID NOs: 20, 21, 22 and 23) and positive control antibody (SEQ ID NOs: 8 and 9) against VEGF-A was determined. Recombinant VEGF-A was coated on a microtiter plate, and the tested agents were titrated starting from a concentration of 100 nM. Bound agents under study were detected via an anti-human IgG Fc antibody as described in Example 2. The data was fit with a 1:1 binding model with EC50 value and the maximum signal as free parameters, and a slope that was fixed to unity.

Figure 3:
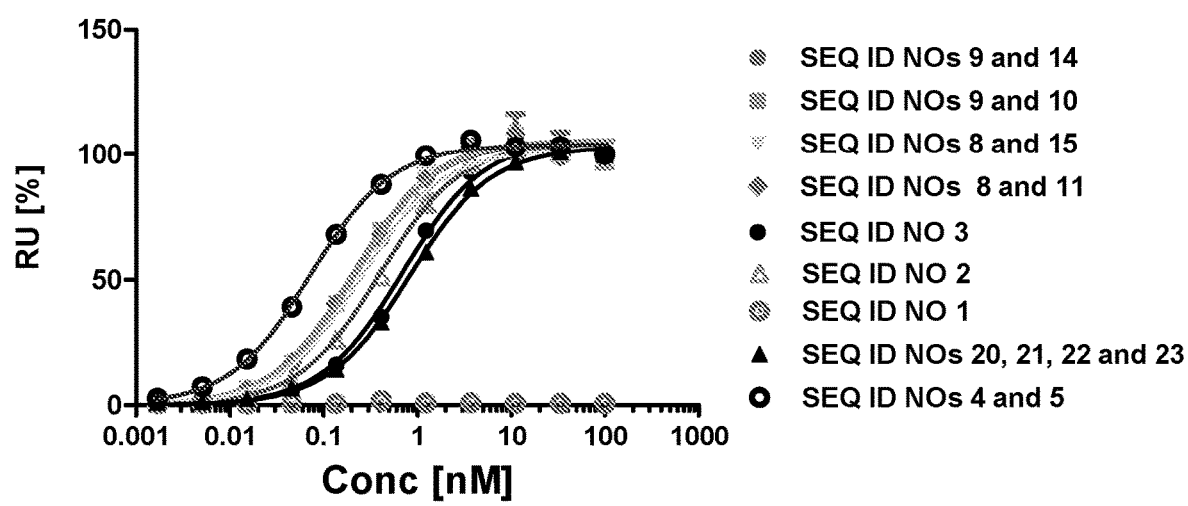

FIG. 3: shows the results of ELISA experiments in which the affinity of representative fusion polypeptides (SEQ ID NOs: 9 and 10, SEQ ID NOs: 8 and 11, SEQ ID NOs: 9 and 14, SEQ ID NOs: 8 and 15), benchmark bispecific antibody (SEQ ID NOs: 20, 21, 22 and 23) and the positive control lipocalin muteins against Ang-2 (SEQ ID NOs: 2 and 3) was determined. Recombinant Ang-2 was coated on a microtiter plate, and the tested agents were titrated starting from a concentration of 100 nM. Bound agents under study were detected via an anti-human-IgG-Fc antibody or anti-lipocalin antibody as described in Example 3. The data was fit with a 1:1 binding model with EC50 value and the maximum signal as free parameters, and a slope that was fixed to unity.

Figure 4:
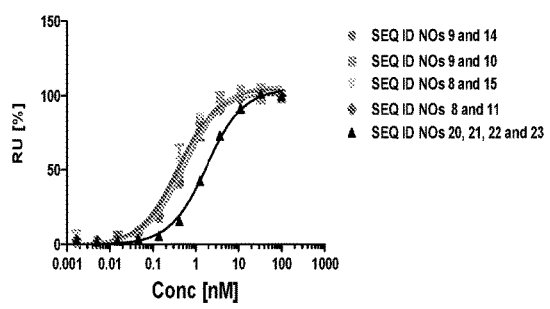
Figure 4:
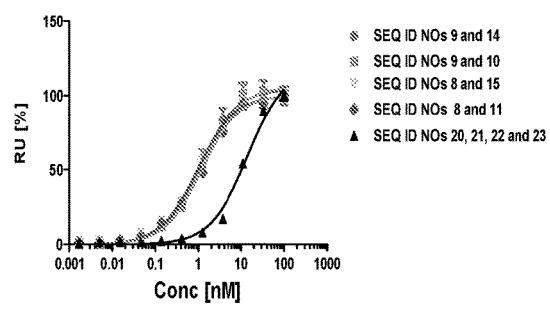

FIG. 4: illustrates the results of an ELISA experiment in which the ability of representative fusion polypeptides (SEQ ID NOs: 9 and 10, SEQ ID NOs: 8 and 11, SEQ ID NOs: 9 and 14, SEQ ID NOs: 8 and 15), to simultaneously bind both targets, VEGF-A and Ang-2, was determined. (A) Recombinant VEGF-A was coated on a microtiter plate, followed by a titration of the fusion polypeptides starting from a concentration of 100 nM. Subsequently, a constant concentration of biotinylated human Ang-2 was added, which was detected via extravidin as described in Example 4. (B) An alternative format was also used where Ang-2 was coated on a microtiter plate, followed by a titration of the fusion polypeptides starting from a concentration of 100 nM. Subsequently, a constant concentration of biotinylated human VEGF-A was added.

Figure 5:
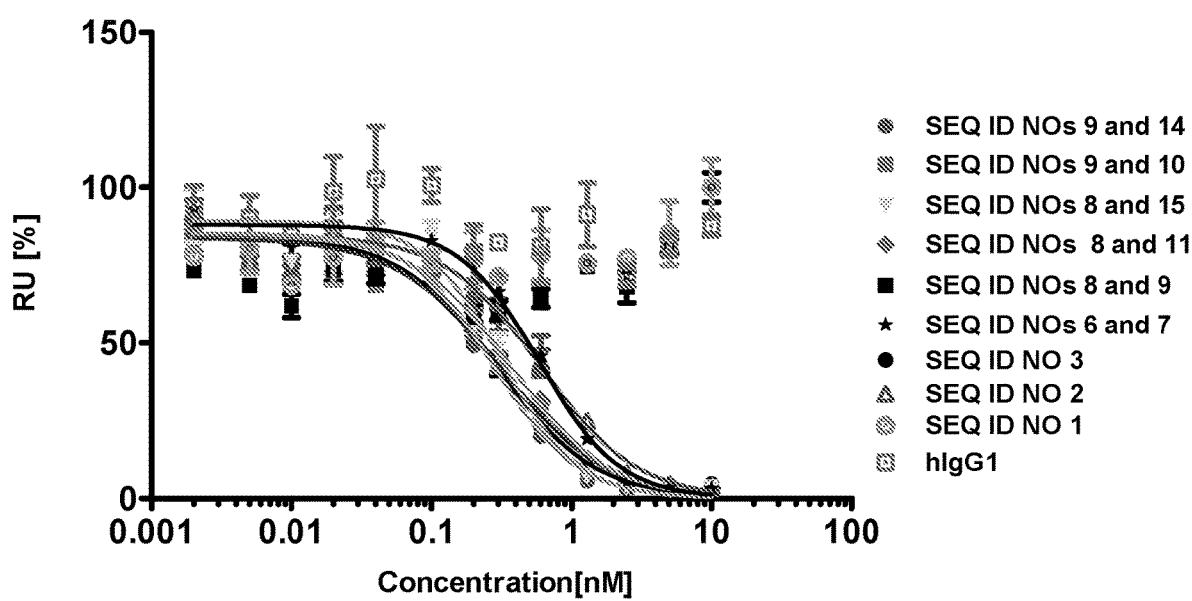

FIG. 5: demonstrates fusion polypeptides (SEQ ID NOs: 9 and 10, SEQ ID NOs: 8 and 11, SEQ ID NOs: 9 and 14, SEQ ID NOs: 8 and 15) and benchmark control (SEQ ID NOs: 6 and 7) are capable of blocking the interaction between human Ang-2 and its receptor human Tie-2, over expressed on HEK cells. A constant concentration of human Ang-2 was pre-incubated with variable concentrations of fusion polypeptides (SEQ ID NOs: 9 and 10, SEQ ID NOs: 8 and 11, SEQ ID NOs: 9 and 14, SEQ ID NOs: 8 and 15) or benchmark control (SEQ ID NOs: 6 and 7). Non-neutralized Ang-2 was detected via an anti-HIS-tag antibody. The data were fitted with a single-site binding model.

FIG. 6: demonstrates that the fusion polypeptides (SEQ ID NOs: 9 and 10, SEQ ID NOs: 8 and 11, SEQ ID NOs: 9 and 14, SEQ ID NOs: 8 and 15) and benchmark controls (SEQ ID NOs: 6 and 7; SEQ ID NOs: 8 and 9) are capable of blocking the biological activity of VEGF-A and/or hAng-2 in a cell-based proliferation assay. In the assay, the fusion polypeptides, an IgG isotype negative control and two benchmark antibodies were added to VEGF-A supplemented Human Lymphatic Endothelial Cells (LEC). The experiment shows that LEC proliferation is blocked by the fusion polypeptides (SEQ ID NOs: 9 and 10, SEQ ID NOs: 8 and 11, SEQ ID NOs: 9 and 14, SEQ ID NOs: 8 and 15) with IC50 values ranging from 1.2-0.5 nM. The VEGF-A benchmark antibody control (SEQ ID NOs: 8 and 9) inhibited proliferation with an IC50 value of 1.2 nM. The lipocalin muteins (SEQ ID NO: 2 or SEQ ID NO: 3) partially inhibited cell proliferation with an IC50 of 1.9-1.7 nM while the Ang-2 benchmark antibody (SEQ ID NOs: 6 and 7) had an IC50 of 4.2 nM. The IgG isotype and SEQ ID NO: 1 negative controls had no effect on cell proliferation. Data were fitted with a sigmoidal dose-response model.

Figure 7:
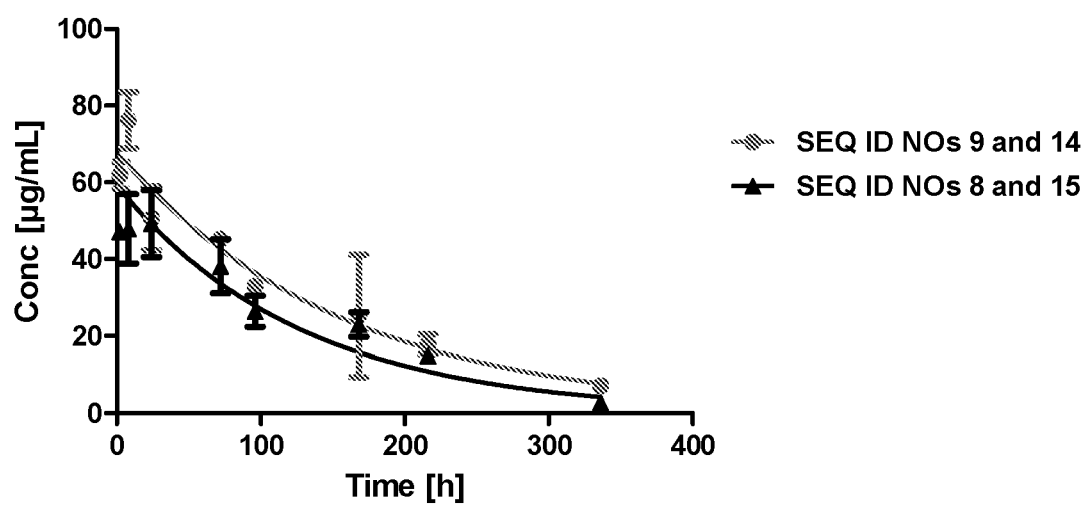

FIG. 7: provides the result of a pharmacokinetic analysis of the bispecific fusion polypeptides (SEQ ID NOs: 9 and 14, SEQ ID NOs: 8 and 15) in rabbits. Female rabbits received test articles as an intravitreal injection in the right eye at a dose of 100 ug/eye. Drug levels were detected using a Sandwich ELISA detecting the full bispecific construct via the targets VEGF-A and Ang-2. The data were fitted using a non-compartmental model.

IV. DETAILED DESCRIPTION OF THE DISCLOSURE

In some embodiments, a fusion polypeptide of the disclosure contains at least two subunits in any order: a first subunit that comprises a full-length immunoglobulin or an antigen-binding domain thereof specific for VEGF-A, and a second subunit that comprises a lipocalin mutein specific for Ang-2. The subunits can be linked via a covalent bond, e.g., a peptide bond.

In some embodiments, one subunit can be linked to another subunit as essentially shown in FIG. 1. For example, one lipocalin mutein can be linked, via a peptide bond, to the C-terminus of the immunoglobulin heavy chain, the N-terminus of the immunoglobulin heavy chain, the C-terminus of the of the immunoglobulin light chain, and/or the N-terminus of the immunoglobulin light chain. In some particular embodiments, a lipocalin mutein subunit can, therefore, be fused at its N-terminus and/or its C-terminus to an immunoglobulin subunit. In some still further embodiments, two subunits can be joined by a peptide linker. The linker can be of any make-up and size and will be apparent to the skilled worker. A preferred linker is a (G4S)3 linker, for example, as shown in SEQ ID NO: 19.

In some embodiments, the fusion polypeptide also may contain a third or additional subunit. For instance, the polypeptide may contain a third subunit comprising a lipocalin mutein specific for a target other than Ang-2 or VEGF-A, which third subunit may be attached at its N or C terminus to the C or N terminus, respectively, of either the first or second subunit.

In some embodiments, in a fusion polypeptide of the disclosure, a VEGF-A-specific subunit is fused to a Ang-2-specific subunit.

In some more specific embodiments, the VEGF-A specific subunit comprises a full-length immunoglobulin (such as a monoclonal antibody) or an antigen-binding domain thereof and the Ang-2-specific subunit comprises a lipocalin mutein. In some embodiments, the fusion polypeptide comprises amino acid sequences selected from the group consisting of SEQ ID NOs: 9 and 10, SEQ ID NOs: 8 and 11, SEQ ID NOs: 9 and 12, SEQ ID NOs: 8 and 13, SEQ ID NOs: 9 and 14, SEQ ID NOs: 8 and 15, SEQ ID NOs: 9 and 16, SEQ ID NOs: 8 and 17, SEQ ID NOs 9 and 24, SEQ ID NOs 8 and 25, SEQ ID NOs 9 and 26, SEQ ID NOs 8 and 27, SEQ ID NOs 9 and 28, SEQ ID NOs 8 and 29, SEQ ID NOs 9 and 30, SEQ ID NOs 8 and 31, SEQ ID NOs 9 and 32, SEQ ID NOs 8 and 33, SEQ ID NOs 9 and 34, SEQ ID NOs 8 and 35, SEQ ID NOs 9 and 36, SEQ ID NOs 8 and 37, SEQ ID NOs 9 and 38, SEQ ID NOs 8 and 39, SEQ ID NOs 9 and 40, SEQ ID NOs 8 and 41, SEQ ID NOs 9 and 42, SEQ ID NOs 8 and 43, SEQ ID NOs 9 and 44, SEQ ID NOs 8 and 45, SEQ ID NOs 9 and 46, SEQ ID NOs 8 and 47, SEQ ID NOs 9 and 48, SEQ ID NOs 8 and 49, SEQ ID NOs 9 and 50, SEQ ID NOs 8 and 51, SEQ ID NOs 9 and 52, SEQ ID NOs 8 and 53, SEQ ID NOs 9 and 54, SEQ ID NOs 8 and 55, SEQ ID NOs 9 and 56, SEQ ID NOs 8 and 57, SEQ ID NOs 9 and 58, SEQ ID NOs 8 and 59, SEQ ID NOs 9 and 60, SEQ ID NOs 8 and 61, SEQ ID NOs 9 and 62, SEQ ID NOs 8 and 63, SEQ ID NOs 9 and 64, SEQ ID NOs 8 and 65, SEQ ID NOs 9 and 66, SEQ ID NOs 8 and 67, SEQ ID NOs 9 and 68, SEQ ID NOs 8 and 69, SEQ ID NOs 9 and 70 and SEQ ID NOs 8 and 71. In some embodiments, the VEGF-A specific subunit comprises a full-length immunoglobulin (such as a monoclonal antibody) or an antigen-binding domain thereof wherein the monoclonal antibody has the heavy chain complementarity-determining regions (CDRs) and the and the light chain CDRs contained in an antibody selected from the group consisting of SEQ ID NOs: 9 and 10, SEQ ID NOs: 8 and 11, SEQ ID NOs: 9 and 12, SEQ ID NOs: 8 and 13, SEQ ID NOs: 9 and 14, SEQ ID NOs: 8 and 15, SEQ ID NOs: 9 and 16, SEQ ID NOs: 8 and 17, SEQ ID NOs 9 and 24, SEQ ID NOs 8 and 25, SEQ ID NOs 9 and 26, SEQ ID NOs 8 and 27, SEQ ID NOs 9 and 28, SEQ ID NOs 8 and 29, SEQ ID NOs 9 and 30, SEQ ID NOs 8 and 31, SEQ ID NOs 9 and 32, SEQ ID NOs 8 and 33, SEQ ID NOs 9 and 34, SEQ ID NOs 8 and 35, SEQ ID NOs 9 and 36, SEQ ID NOs 8 and 37, SEQ ID NOs 9 and 38, SEQ ID NOs 8 and 39, SEQ ID NOs 9 and 40, SEQ ID NOs 8 and 41, SEQ ID NOs 9 and 42, SEQ ID NOs 8 and 43, SEQ ID NOs 9 and 44, SEQ ID NOs 8 and 45, SEQ ID NOs 9 and 46, SEQ ID NOs 8 and 47, SEQ ID NOs 9 and 48, SEQ ID NOs 8 and 49, SEQ ID NOs 9 and 50, SEQ ID NOs 8 and 51, SEQ ID NOs 9 and 52, SEQ ID NOs 8 and 53, SEQ ID NOs 9 and 54, SEQ ID NOs 8 and 55, SEQ ID NOs 9 and 56, SEQ ID NOs 8 and 57, SEQ ID NOs 9 and 58, SEQ ID NOs 8 and 59, SEQ ID NOs 9 and 60, SEQ ID NOs 8 and 61, SEQ ID NOs 9 and 62, SEQ ID NOs 8 and 63, SEQ ID NOs 9 and 64, SEQ ID NOs 8 and 65, SEQ ID NOs 9 and 66, SEQ ID NOs 8 and 67, SEQ ID NOs 9 and 68, SEQ ID NOs 8 and 69, SEQ ID NOs 9 and 70 and SEQ ID NOs 8 and 71.

In some embodiments, the second subunit is comprised of a lipocalin mutein which comprises amino acid sequences selected from the group consisting of SEQ ID NOs: 2, 3, 86, 87, 88, 89, 90, 91, 92, 93, 94, 95, 96 and 97.

In some embodiments, the second subunit is comprised of a lipocalin mutein which comprises nucleic acid sequences selected from the group consisting of SEQ ID NOs: 72-85.

In some embodiments, the Fc portion of the immunoglobulin included in a fusion polypeptide of the disclosure may contribute to maintaining the serum levels of the fusion polypeptide, critical for its stability and persistence in the body. For example, when the Fc portion binds to Fc receptors on endothelial cells and on phagocytes, the fusion polypeptide may become internalized and recycled back to the blood stream, enhancing its half-life.

In some embodiments, a fusion polypeptide of the disclosure may be able to bind VEGF-A with an EC50 value of about 1 nM or less, such as about 0.5 nM, about 0.3 nM or about 0.15 nM, for example, when said affinity for VEGF-A is measured in an ELISA assay essentially as described in Example 2.

In some embodiments, a fusion polypeptide of the disclosure may be able to bind VEGF-A with an EC50 value, comparable to the EC50 value of the immunoglobulin specific for VEGF-A as included in such fusion polypeptide, such as the antibody having the heavy and light chains provided by SEQ ID NOs: 8 and 9, for example, when said immunoglobulin and the fusion polypeptide are measured in as ELISA assay essentially as described in Example 2.

In some embodiments, a fusion polypeptide of the disclosure may be able to bind Ang-2 with an EC50 value of about 1 nM or less, such as about 0.5 nM, about 0.25 nM or about 0.1 nM, for example, when said affinity for Ang-2 is measured in an ELISA assay essentially as described in Example 3. A fusion polypeptide of the disclosure may be able to bind Ang-2 with an EC50 value comparable to the EC50 value of the lipocalin mutein specific for Ang-2 as included in such fusion polypeptide, such as lipocalin muteins of SEQ ID NOs: 2 and 3, for example, when said lipocalin mutein and the fusion polypeptide are measured in as ELISA assay essentially as described in Example 3.

In some embodiments, the fusion polypeptides of the disclosure specific for both VEGF-A and Ang-2 may be capable of simultaneously binding VEGF-A and Ang-2, for example, when said fusion polypeptide is measured in an ELISA assay essentially described in Example 4.

In some embodiments, the fusion polypeptides of the disclosure may be able to block the binding of human Ang-2 to human Tie-2 expressing cells in a competition cell electrochemoluminescence (ECL) assay format as essentially described in Example 5.

In some embodiments, the fusion polypeptide of the disclosure is able to block VEGF-A dependent cell proliferation, in particular neutralize the biological activity of VEGF-A in a short-term proliferation assay using lymphatic microvascular endothelial cells (LEC) as essentially described in Example 6.

A. Exemplary Immunoglobulins as Included in the Fusion Polypeptides.

In some embodiments, with respect to the fusion polypeptide, the first subunit comprises a full-length immunoglobulin or an antigen-binding domain thereof specific for VEGF-A. The immunoglobulin, for example, may be IgG1, IgG2, IgG3 or IgG4, and preferentially is IgG1. In further embodiments, the immunoglobulin is a monoclonal antibody against VEGF-A. A few illustrative examples for such immunoglobulins include bevacizumab (trade name Avastin) and ranibizumab (trade name Lucentis), for example.

B. Exemplary Lipocalin Muteins as Included in the Fusion Polypeptides.

As used herein, a "lipocalin" is defined as a monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

As noted above, a lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind Ang-2 with detectable affinity.

In one particular embodiment, a lipocalin mutein disclosed herein is a mutein of human lipocalin 2. The term "human lipocalin 2" or "human Lcn 2" or "human NGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 1 is used as reference sequence.

In some embodiments, a lipocalin mutein comprised in the fusion polypeptide of the disclosure binding Ang-2 with detectable affinity may include at least one amino acid substitution of a native cysteine residue by another amino acid, for example, a serine residue. In some other embodiments, a lipocalin mutein binding Ang-2 with detectable affinity may include one or more non-native cysteine residues substituting one or more amino acids of a wild-type lipocalin. In a further particular embodiment, a lipocalin mutein according to the disclosure includes at least two amino acid substitutions of a native amino acid by a cysteine residue, hereby to form one or more cysteine bridges. In some embodiments, said cysteine bridge may connect at least two loop regions. The definition of these regions is used herein in accordance with Flower (Flower, 1996, supra, Flower, et al., 2000, supra) and Breustedt et al. (2005, supra).

Polypeptides of the disclosure, which are, in part, directed against or specific for Ang-2, include any number of specific-binding protein muteins that are based on a defined protein scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred. However, it is preferred that a lipocalin mutein of the disclosure is still capable of binding Ang-2.

In one aspect, the present fusion polypeptide of the disclosure comprises various lipocalin muteins that bind Ang-2 with at least detectable affinity. In this sense, Ang-2 can be regarded a non-natural ligand of the reference wild-type lipocalin, where "non-natural ligand" refers to a compound that does not bind to wild type lipocalins under physiological conditions. By engineering wild type lipocalins with one or more mutations at certain sequence positions, the present inventors have demonstrated that high affinity and high specificity for the non-natural ligand, Ang-2, is possible. In some embodiments, at 1, 2, 3, 4, 5, 6, 7, 8, 9, 10, 11, 12 or even more nucleotide triplet(s) encoding certain sequence positions on wild type lipocalins, a random mutagenesis may be carried out through substitution at these positions by a subset of nucleotide triplets.

Further, the lipocalin muteins comprised in the fusion polypeptide of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of the reference lipocalin.

A fusion polypeptide of the disclosure may include the wild-type (natural) amino acid sequence of the "parental" protein scaffold (such as a lipocalin) outside the mutated amino acid sequence positions. In some embodiments, a lipocalin mutein comprised in the fusion polypeptide of the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the hNGAL as long as these deletions or insertion result in a stable folded/functional mutein (for example, hNGAL muteins with truncated N- and C-terminus). In such mutein, for instance, one or more amino acid residues are added or deleted at the N- or C-terminus of the polypeptide. Generally, such a mutein may have about at least 70%, including at least about 80%, such as at least about 85% amino acid sequence identity, with the amino acid sequence of the mature hNGAL. As an illustrative example, the present disclosure also encompasses NGAL muteins as defined above, in which amino acid residues (Lys-Asp-Pro, positions 46-48) of the linear polypeptide sequence of the mature human lipocalin 2 (hNGAL) have been deleted (SEQ ID NO: 1).

The amino acid sequence of a lipocalin mutein comprised in the fusion polypeptide disclosed herein has a high sequence identity to the reference lipocalin when compared to sequence identities with other lipocalins. In this general context, the amino acid sequence of a lipocalin mutein of the disclosure is at least substantially similar to the amino acid sequence of the reference lipocalin, with the proviso that possibly there are gaps (as defined below) in an alignment that are the result of additions or deletions of amino acids. A respective sequence of a lipocalin mutein of the disclosure, being substantially similar to the sequences of the reference lipocalin, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the reference lipocalin, with the proviso that the altered position or sequence is retained and that one or more gaps are possible.

As used herein, a lipocalin mutein comprised in the fusion polypeptide of the disclosure "specifically binds" a target (for example, Ang-2) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the lipocalin muteins of the disclosure are fused at its N-terminus and/or its C-terminus to a fusion partner which is a protein domain that extends the serum half-life of the mutein. In further particular embodiments, the protein domain is a Fc part of an immunoglobulin, a CH3 domain of an immunoglobulin, a CH4 domain of an immunoglobulin, an albumin binding peptide, or an albumin binding protein.

In another embodiment, the lipocalin muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immunoglobulin, a CH4 domain of an immunoglobulin, an albumin binding peptide, and an albumin binding protein.

In yet another embodiment, the current disclosure relates to a nucleic acid molecule comprising a nucleotide sequence encoding a fusion polypeptide comprising a lipocalin mutein disclosed herein. The disclosure encompasses a host cell containing said nucleic acid molecule.

In one aspect, the present disclosure provides a fusion polypeptide comprising a lipocalin mutein that binds Ang-2 and useful applications therefor. The disclosure also provides methods of making such fusion polypeptide comprising an Ang-2 binding subunit described herein as well as compositions comprising such a fusion polypeptide. The Ang-2 binding subunit of the disclosure as well as compositions thereof may be used in methods of detecting Ang-2 in a sample or in methods of binding of Ang-2 in a subject. No such fusion polypeptide comprising such human lipocalin muteins having these features attendant to the uses provided by present disclosure have been previously described.

1. Exemplary Lipocalins Muteins Specific for Ang-2

In one aspect, the present disclosure provides a fusion polypeptide comprising an Ang-2 binding human lipocalin 2 (human Lcn2 or hNGAL) muteins.

One embodiment of the current disclosure relates to a fusion polypeptide comprising a mutein that is capable of binding Ang-2 with detectable affinity, such as an affinity measured by a $K_d$ of about 200 nM or lower, such as about 150 nM or lower.

In one aspect, the current disclosure provides a fusion polypeptide comprising an hNGAL mutein that is capable of binding Ang-2 with a $K_d$ of about 5 nM or lower, for example when measured by Biacore T200 instrument in a Surface Plasmon Resonance (SPR).

In some further embodiments, one or more hNGAL muteins comprised in the fusion polypeptide of the disclosure are capable of binding Ang-2 with an affinity measured by an EC50 value of about 5 nM or lower, when measured in an ELISA assay.

In some other embodiments, one or more hNGAL muteins comprised in the fusion polypeptide of the disclosure are capable of binding Ang-2 with an affinity measured by an IC50 value of about 5 nM or lower, when measured in a competition ELISA format assay.

In some other embodiments, one or more hNGAL muteins comprised in the fusion polypeptide of the disclosure are capable of inhibiting or reducing lymphatic microvascular endothelial cells proliferation mediated by Ang-2 with an IC50 value of about 5 nM or lower in a cell-based proliferation assay.

In some other embodiments, one or more hNGAL muteins comprised in the fusion polypeptide of the disclosure are cross-reactive with both human Ang-2 and mouse Ang-2. In some embodiments, one or more such muteins are capable binding both human Ang-2 and mouse Ang-2 with detectable affinity, such as an affinity measured by a $K_d$ of about 200 nM or lower, such as about 150 nM or lower.

In some still further embodiments, one or more such muteins comprised in the fusion polypeptide of the disclosure are capable of binding mouse Ang-2 with an affinity measured by an IC50 value of about 5 nM or lower, when measured in an ELISA assay.

In some still further embodiments, one or more such muteins comprised in the fusion polypeptide of the disclosure are capable of blocking binding of human Ang-2 to hTie-2 and mouse Ang-2 to hTie-2 with an IC50 value of about 25 nM or lower, respectively, in a competition cell ECL format.

In some embodiments, one or more hNGAL muteins comprised in the fusion polypeptide of the disclosure are not cross-reactive with human Ang-4. In some embodiments, one or more hNGAL muteins comprised in the fusion polypeptide of the disclosure are not cross-reactive with mouse Ang-3. In some embodiments, one or more hNGAL muteins comprised in the fusion polypeptide of the disclosure are not cross-reactive with human VEGF-A.

In this regard, the disclosure relates to a fusion polypeptide, wherein said fusion polypeptide includes an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40, 41, 49, 52, 65, 68, 70, 72-74, 77, 79, 81, 87, 96, 100, 103, 106, 116, 125, 126, 127, 129, 132 and 134, and wherein said polypeptide binds Ang-2 with detectable affinity.

In some embodiments, an Ang-2-binding hNGAL mutein comprised in the fusion polypeptide of the disclosure includes, at any one or more of the sequence positions 36, 40, 41, 49, 52, 68, 70, 72-73, 77, 79, 81, 96, 100, 103, 106, 125, 127, 132 and 134 of the linear polypeptide sequence of the mature hNGAL (SEQ ID NO: 1), one or more of the following mutated amino acid residues: Leu 36→Gln, Glu, His, Val, Met or Phe; Ala 40→Val, Tyr, His or Trp; Ile 41→His, Tyr, Trp or Val; Gln 49→Gly, Ile, Val, Glu or Val; Tyr 52→Trp, His, Thr or Ser; Ser 68→Gly, Asp, Gln, Glu or Ile; Leu 70→Ser, Thr, Gly, Arg, Tyr or Ala; Arg 72→Gly, Ala, Trp, Thr or Glu; Lys 73→Pro, Phe, Leu, Arg, Ala or Gln; Asp 77→Asn, Lys, Ser or Val; Trp 79→Thr, Arg, Ser or Asn; Arg 81→Trp, His or Tyr; Asn 96→Gly, Ala, Pro, Gln or Asp; Tyr 100→Pro, Trp, Gly, Ser, Leu or Asp; Leu 103→Gly, Glu, Asp, Met or Gln; Tyr 106→Thr, Leu or Phe; Lys 125→His, Thr or Gly; Ser 127→Leu or Met; Tyr 132→Phe, Trp or Val; and Lys 134→Ala, Glu or Trp. In some embodiments, an hNGAL mutein of the disclosure includes two or more, such as 3, 4, 5, 6, 7, 8, 9, 10, 11, 12, 13, 14, 15, 16, or even more or all mutated amino acid residues at these sequence positions of the mature hNGAL.

Additionally, an Ang-2-binding hNGAL mutein comprised in the fusion polypeptide of the disclosure may also comprise the following substitution in comparison with the linear polypeptide sequence of the mature hNGAL: Gln 28→His; Asn 65→Asp; Lys 74→Glu; Cys 87→Ser; Asn 116→Asp; Val 126→Met and Asn 129→Asp.

In some additional embodiments, an hNGAL mutein comprised in the fusion polypeptide of the disclosure which binds to Ang-2 includes the following amino acid replacements in comparison with the linear polypeptide sequence of the mature hNGAL:

(a) Leu 36→Gln; Ala 40 Tyr; Gln 49→Gly; Tyr 52→Trp; Ser 68→Gly; Leu 70→Ser; Arg 72→Gly; Lys 73→Pro; Asp 77→Asn; Trp 79→Thr; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;

(b) Leu 36→Phe; Ala 40 His; Ile 41→Arg; Gln 49→Gly; Tyr 52→His; Ser 68→Asp; Leu 70→Thr; Arg 72→Ala; Lys 73→Phe; Asp 77→Asn; Trp 79→Arg; Arg 81→His; Tyr 100→Trp; Leu 103→Glu; Tyr 106→Thr; Lys 125→Thr; Ser 127→Met; Tyr 132→Trp; Lys 134→Trp;

(c) Leu 36→Val; Ala 40→Trp; Ile 41→Tyr; Gln 49→Ile; Tyr 52→Thr; Ser 68→Gln; Leu 70→Gly; Arg 72→Glu; Lys 73→Gln; Asp 77→Lys; Trp 79→Ser; Arg 81→His; Tyr 100→Trp; Leu 103→Asp; Tyr 106→Leu; Lys 125→Gly; Ser 127→Met; Tyr 132→Val; Lys 134→Ala;

(d) Leu 36→Glu, Ala 40 Val; Ile 41→Glu; Gln 49→Val; Tyr 52→Thr Ser 68→Glu; Leu 70→Arg; Arg 72→Trp; Lys 73→Leu; Asp 77→Lys; Trp 79→Asn; Arg 81→His; Asn 96→Ala; Tyr 100→Gly; Leu 103→Met; Tyr 106→Thr; Lys 125→Thr; Ser 127→Met; Tyr 132→Trp; Lys 134→Trp;

(e) Leu 36→Gln; Ala 40→Tyr; Ile 41→Trp; Gln 49→Ile; Tyr 52→Ser; Ser 68→Ile; Leu 70→Tyr; Arg 72→Thr; Lys 73→Arg; Asp 77→Ser; Trp 79→Arg; Arg 81→Tyr; Asn 96→Pro; Leu 103→Asp; Tyr 106→Thr; Lys 125→His; Ser 127→Tyr; Tyr 132→Trp; Lys 134→Glu;

(f) Leu 36→Gln; Ala 40→Tyr; Gln 49→Glu; Tyr 52→Trp; Asn 65→Asp; Ser 68→Gly; Leu 70→Ser; Arg 72→Gly; Lys 73→Pro; Asp 77→Asn; Trp 79→Arg; Arg 81→Trp; Asn 96→Gly; Tyr 100→Ser; Leu 103→Gln; Tyr 106→Thr; Lys 125→His; Ser 127→Leu; Tyr 132→Phe; Lys 134→Glu;

(g) Leu 36→His; Ala 40 Tyr; Gln 49→Glu; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Pro; Leu 103→Asp; Tyr 106→Thr; Lys 125→His; Ser 127→Leu; Tyr 132→Phe; Lys 134→Glu;

(h) Leu 36→Gln; Ala 40 Tyr; Gln 49→Gly; Tyr 52→Trp; Asn 65→Asp; Ser 68→Glu; Leu 70→Ser; Arg 72→Gly; Lys 73→Ala; Asp 77→Asn; Trp 79→Arg; Arg 81→Trp; Asn 96→Gly; Tyr 100→Asp; Leu 103→Gly; Tyr 106→Thr; Lys 125→His; Ser 127→Leu; Tyr 132→Phe; Lys 134→Glu;

(i) Leu 36→His; Ala 40 Tyr; Gln 49→Gly; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;

(j) Leu 36→Gln; Ala 40 Tyr; Gln 49→Gly; Tyr 52→Trp; Asn 65→Asp; Ser 68→Gly; Leu 70→Ser; Arg 72→Gly; Lys 73→Ala; Asp 77→Val; Trp 79→Arg; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;

(k) Leu 36→Gln; Ala 40 Tyr; Gln 49→Val; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Leu; Leu 103→Gly; Tyr 106→Thr; Lys 125→His; Ser 127→Leu; Tyr 132→Phe; Lys 134→Glu;

(l) Leu 36→Val; Ala 40 Tyr; Ile 41→Tyr; Gln 49→Ile; Tyr 52→Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Tyr 100→Trp; Leu 103→Asp; Tyr 106→Pro; Asn 116→Asp; Lys 125→Gly; Ser 127→Met; Asn 129→Asp; Tyr 132→Val; Lys 134→Ala;

(m) Leu 36→Val; Ala 40 Tyr; Ile 41→Tyr; Gln 49→Ile; Tyr 52→Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Asn 96→Asp; Tyr 100→Trp; Leu 103→Asp; Tyr 106→Pro; Lys 125→Gly; Val 126→Met; Ser 127→Met; Asn 129→Asp; Tyr 132→Val; Lys 134→Ala; or (n) Leu 36→Met; Ala 40→Tyr; Ile 41→Asp; Gln 49→Ile; Tyr 52→Thr; Asn 65→Asp; Ser 68→Gln; Leu 70→Gly; Arg 72→Glu; Lys 73→Gln; Asp 77→Lys; Trp 79→Ser; Arg 81→His; Asn 96→Gln; Tyr 100→Trp; Leu 103→Asp; Tyr 106→Pro; Lys 125→Gly; Ser 127→Met; Tyr 132→Val; Lys 134→Ala.

Each of these sets of amino acid replacements may further include the replacements Gln 28→His and Cys 87→Ser.

In the residual region, i.e. the region differing from sequence positions 28, 36, 40, 41, 49, 52, 65, 68, 70, 72-74, 77, 79, 81, 87, 96, 100, 103, 106, 116, 125, 126, 127, 129, 132 and 134, an hNGAL mutein comprised in the fusion polypeptide of the disclosure may include the wild type (natural) amino acid sequence outside the mutated amino acid sequence positions.

In further particular embodiments, a mutein comprised in the fusion polypeptide of the disclosure according to the current disclosure comprises an amino acid sequence selected from the group consisting of SEQ ID NOs: 2, 3, 86, 87, 88, 89, 90, 91, 92, 93, 94, 95, 96 or 97 or a functional fragment or variant thereof. In some embodiments, such fragment or variant is a structural homologue of a mutein defined in any one of SEQ ID NOs: 2, 3, 86, 87, 88, 89, 90, 91, 92, 93, 94, 95, 96 or 97.

The amino acid sequence of an Ang-2-binding hNGAL mutein comprised in the fusion polypeptide of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 2, 3, 86, 87, 88, 89, 90, 91, 92, 93, 94, 95, 96 or 97.

In some still embodiments, an hNGAL mutein cross-reactive with human Ang-2 and/or mouse Ang-2 according to the disclosure comprises an amino acid sequence selected from the group consisting of SEQ ID NOs: 2, 3, 86, 87, 88, 89, 90, 91, 92, 93, 94, 95, 96 or 97 and functional fragments or variants thereof.

The disclosure also includes structural homologues of an hNGAL mutein comprised in the fusion polypeptide of the disclosure having an amino acid sequence selected from the group consisting of SEQ ID NOs: 2, 3, 86, 87, 88, 89, 90, 91, 92, 93, 94, 95, 96 or 97, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

An Ang-2-binding hNGAL mutein comprised in the fusion polypeptide of the disclosure can be obtained by means of mutagenesis of a naturally occurring form of human lipocalin 2 (or hNGAL). In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Ang-2, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

The present disclosure also relates to a pharmaceutical composition that includes at least one fusion polypeptide of the disclosure comprising an Ang-2-binding hNGAL mutein, or conjugate or fusion protein thereof as described herein, and optionally, a pharmaceutically acceptable excipient.

Accordingly, the Ang-2-binding hNGAL muteins comprised in the fusion polypeptide of the disclosure can be formulated into compositions using pharmaceutically acceptable ingredients as well as established methods of preparation (Gennaro and Gennaro (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used.

C. Muteins Comprised in the Fusion Polypeptide of the Disclosure.

When used herein in the context of the fusion polypeptide of the present disclosure, the term "specific for", in reference to a mutein that binds to Ang-2, includes that the mutein is directed against, binds to, or reacts with Ang-2. Thus, being directed to, binding to or reacting with includes that the mutein specifically binds to Ang-2. The term "specifically" in this context means that the mutein engages Ang-2, as described herein, but essentially not with another target. Whether the mutein specifically binds or engages a target as defined above can easily be tested, inter alia, by comparing the reaction of a hNGAL mutein comprised in the fusion polypeptide of the present disclosure with Ang-2 and the reaction of said mutein with (an) other target(s). "Specific binding" can also be determined, for example, in accordance with Western blots, ELISA-, RIA-, ECL-, IRMA-tests, FACS, IHC and peptide scans.

The amino acid sequence of a mutein comprised in the fusion polypeptide of the disclosure has a high sequence identity to human lipocalin 2 when compared to sequence identities with another lipocalin (see also above). In this general context the amino acid sequence of a mutein of the combination according to the disclosure is at least substantially similar to the amino acid sequence of the corresponding lipocalin (the wild-type hNGAL). A respective sequence of a mutein of the combination according to the disclosure, being substantially similar to the sequence of mature hNGAL, such as at least 65%, at least 70%, at least 75%, at least 80%, at least 82%, at least 85%, at least 87%, at least 90% identity, including at least 95% identity to the sequence of mature hNGAL. In this regard, a mutein of the disclosure of course may contain, in comparison substitutions as described herein which renders the mutein capable of binding to Ang-2. Typically, a mutein of hNGAL includes one or more mutations—relative to the native sequence of hNGAL—of amino acids in the four loops at the open end of the ligand binding site of hNGAL. As explained above, these regions are essential in determining the binding specificity of a mutein for Ang-2. A mutein derived hNGAL or a homologue thereof, may have one, two, three, four or more mutated amino acid residues at any sequence position in the N-terminal region and/or in the three peptide loops BC, DE, and FG arranged at the end of the β-barrel structure that is located opposite to the natural binding pocket.

A mutein comprised in the fusion polypeptide of the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native hNGAL lipocalin, provided that such a mutein should be capable of binding to Ang-2. For example, a mutein can have a substitution at a position corresponding to a distinct position (i.e. at a corresponding position) of hNGAL. In some embodiments a mutein of the combination according to the disclosure includes at least two amino acid substitutions, including 2, 3, 4, 5, or even more, amino acid substitutions of a native amino acid by an arginine residue. Accordingly, the nucleic acid of a protein 'reference' scaffold as described herein is subject to mutagenesis with the aim of generating a mutein which is capable of binding to Ang-2.

Also, a mutein comprised in the fusion polypeptide of the present disclosure can comprise a heterologous amino acid sequence at its N- or C-Terminus, preferably C-terminus, such as a Strep-tag, e.g., Strep II tag without affecting the biological activity (binding to its target e.g. Ang-2) of the mutein.

Specifically, in order to determine whether an amino acid residue of the amino acid sequence of a mutein comprised in the fusion polypeptide of the disclosure different from wild-type hNGAL corresponds to a certain position in the amino acid sequence of wild-type hNGAL, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, wild-type hNGAL can serve as "subject sequence" or "reference sequence", while the amino acid sequence of a mutein different from the wild-type hNGAL described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the mutein comprised in the fusion polypeptide of the disclosure retains its capability to bind Ang-2, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn Gln, His; Asp→Glu; Cys Ser; Gln Asn; Glu→Asp; Gly→Ala; His→Arg, Asn, Gln; Ile Leu, Val; Leu Ile, Val; Lys→Arg, Gln, Glu; Met→Leu, Tyr, Ile; Phe→Met, Leu, Tyr; Ser Thr; Thr Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

a. Alanine (Ala), Glycine (Gly);
b. Aspartic acid (Asp), Glutamic acid (Glu);
c. Asparagine (Asn), Glutamine (Gln);
d. Arginine (Arg), Lysine (Lys);
e. Isoleucine (Ile), Leucine (Leu), Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg Gln; Asn→Asp, Lys, Arg, His; Asp→Asn; Cys→Ala; Gln Glu; Glu Gln; His→Lys; Ile→Met, Ala, Phe; Leu→Ala, Met, Norleucine; Lys→Asn; Met→Phe; Phe→Val, Ile, Ala; Trp Phe; Tyr→Thr, Ser; Val→Met, Phe, Ala.

Substantial modifications in the biological properties of hNGAL are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: asparitic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of hNGAL also may be substituted, generally with serine, to improve the oxidative stability of the molecule and prevent aberrant crosslinking. Conversely, cysteine bond (s) may be added to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of hNGAL as long as these deletions or insertion result in a stable folded/functional mutein.

Modifications of the amino acid sequence include directed mutagenesis of single amino acid positions in order to simplify sub-cloning of the mutated hNGAL gene or its parts by incorporating cleavage sites for certain restriction enzymes. In addition, these mutations can also be incorporated to further improve the affinity of a mutein for a given target such as Ang-2. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective mutein.

It is also possible to mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages.

In some embodiments, if one of the above moieties is conjugated to a mutein comprised in the fusion polypeptide of the disclosure, conjugation to an amino acid side chain can be advantageous. Suitable amino acid side chains may occur naturally in the amino acid sequence of hNGAL or may be introduced by mutagenesis. In case a suitable binding site is introduced via mutagenesis, one possibility is the replacement of an amino acid at the appropriate position by a cysteine residue.

With respect to a mutein of human lipocalin 2 comprised in the fusion polypeptide of the disclosure, exemplary possibilities of such a mutation to introduce a cysteine residue into the amino acid sequence of a lipocalin including human lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of human NGAL. In some embodiments where a human lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No. P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human lipocalin 2 mutein.

In another embodiment, in order to provide suitable amino acid side chains for conjugating one of the above compounds to a mutein comprised in the fusion polypeptide of the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

In some embodiments, a mutein comprised in the fusion polypeptide of the disclosure may be fused at its N-terminus or its C-terminus to a protein, a protein domain or a peptide, for instance, a signal sequence and/or an affinity tag.

Affinity tags such as the Strep-Tag® or Strep-Tag® II (Schmidt, T. G. M. et al. (1996) *J. Mol. Biol.* 255, 753-766), the myc-tag, the FLAG-tag, the His$_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for muteins of the disclosure as well.

In general, it is possible to label the muteins comprised in the fusion polypeptide of the disclosure with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins comprised in the fusion polypeptide of the disclosure. The muteins comprised in the fusion polypeptide of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The muteins comprised in the fusion polypeptide of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a mutein comprised in a fusion polypeptide of the disclosure may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a mutein with binding activity for albumin. Accordingly, suitable conjugation partners for extending the half-life of a mutein comprised in a fusion polypeptide of the disclosure include an albumin binding protein, for example, a bacterial albumin binding domain, such as the one of streptococcal protein G (König, T., & Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in U.S. Patent Application 2003/0069395 (incorporated herein by reference in its entirety) or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself (Osborn, B. L. et al., 2002, *J. Pharmacol. Exp. Ther.* 303, 540-548), or a biological active fragment of albumin can be used as conjugation partner of a mutein comprised in a fusion polypeptide of the disclosure. The term "albumin" includes all mammal albumins such as human serum albumin or bovine serum albumin or rat albumin. The albumin or fragment thereof can be recombinantly produced as described in U.S. Pat. No. 5,728,553 or European Patent Applications EP 0 330 451 and EP 0 361 991 (incorporated herein by reference in their entirety). Recombinant human albumin (Recombumin®) Novozymes Delta Ltd. (Nottingham, UK) can be conjugated or fused to a mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins comprised in a fusion polypeptide of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins comprised in a fusion polypeptide of the disclosure, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the muteins of the disclosure is to fuse to the N- or C-terminus of the muteins long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the disclosure for the purpose of serum half-life extension.

In addition, a mutein comprised in a fusion polypeptide of the disclosure may be fused to a moiety which may confer new characteristics to the muteins of the disclosure such as enzymatic activity or binding affinity for other molecules. Examples of suitable fusion partners are alkaline phosphatase, horseradish peroxidase, gluthation-S-transferase, the albumin-binding domain of protein G, protein A, antibody fragments, oligomerization domains or toxins.

In particular, it may be possible to fuse a mutein comprised in a fusion polypeptide of the disclosure herein with a separate enzyme active site such that both "components" of the resulting fusion protein together act on a given therapeutic target. The binding domain of the mutein comprised in a fusion polypeptide of the disclosure attaches to the disease-causing target, allowing the enzyme domain to abolish the biological function of the target.

The present disclosure also relates to nucleic acid molecules (DNA and RNA) that include nucleotide sequences encoding the muteins comprised in the fusion polypeptide of the disclosure. Since the degeneracy of the genetic code permits substitutions of certain codons by other codons specifying the same amino acid, the disclosure is not limited to a specific nucleic acid molecule encoding a mutein as described herein but encompasses all nucleic acid molecules that include nucleotide sequences encoding a functional mutein. In this regard, the present disclosure provides nucleotide sequences, as shown in SEQ ID NOs: 72-85, encoding some muteins comprised in a fusion polypeptide of the disclosure.

In one embodiment of the disclosure, the method includes subjecting the nucleic acid molecule to mutagenesis at nucleotide triplets coding for at least one, or even more, of the sequence positions corresponding to the sequence positions 28, 36, 40, 41, 49, 52, 65, 68, 70, 72-74, 77, 79, 81, 87, 96, 100, 103, 106, 116, 125, 126, 127, 129, 132 and 134 of the linear polypeptide sequence of human NGAL (SEQ ID NO: 1).

The disclosure also includes nucleic acid molecules encoding the muteins comprised in the fusion polypeptide of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a mutein comprised in a fusion polypeptide as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g., HeLa cells or CHO cells) or primary mammalian cells.

The disclosure also relates to a method for the production of a mutein comprised in a fusion polypeptide as described herein, wherein the mutein or polypeptide, a fragment of the mutein or a fusion protein of the mutein is produced starting from the nucleic acid coding for the mutein or polypeptide by means of genetic engineering methods. The method can be carried out in vivo, the mutein or polypeptide can for example be produced in a bacterial or eukaryotic host organism and then isolated from this host organism or its culture. It is also possible to produce a protein in vitro, for example by use of an in vitro translation system.

When producing the mutein comprised in the fusion polypeptide of the disclosure in vivo a nucleic acid encoding such mutein or polypeptide is introduced into a suitable bacterial or eukaryotic host organism by means of recombinant DNA technology (as already outlined above). For this purpose, the host cell is first transformed with a cloning vector that includes a nucleic acid molecule encoding a mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in hNGAL muteins comprised in the fusion polypeptide of the disclosure. Accordingly, such muteins can be produced in a cell compartment having a reducing redox milieu, for example, in the cytoplasm of Gram-negative bacteria.

In case a mutein comprised in the fusion polypeptide of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmic reticulum of eukaryotic cells and usually favors the formation of structural disulfide bonds.

It is, however, also possible to produce a mutein comprised in the fusion polypeptide of the disclosure in the cytosol of a host cell, preferably *E. coli*. In this case, the mutein or polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

However, the mutein or polypeptide comprised in the fusion polypeptide as described herein may not necessarily be generated or produced only by use of genetic engineering. Rather, such mutein or polypeptide can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for Ang-2. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the mutein or polypeptide comprised in the fusion polypeptide of the disclosure may be produced by in vitro transcription/translation employing well-established methods known to those skilled in the art.

The skilled worker will appreciate methods useful to prepare muteins or polypeptides comprised in a fusion polypeptide thereof contemplated by the present disclosure but whose protein or nucleic acid sequences are not explicitly disclosed herein. As an overview, such modifications of the amino acid sequence include, e.g., directed mutagenesis of single amino acid positions in order to simplify subcloning of a mutated hNGAL gene or its parts by incorporating cleavage sites for certain restriction enzymes. In addition, these mutations can also be incorporated to further improve the affinity of a mutein for its target (e.g. Ang-2 or Ang-1, respectively). Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

The muteins or polypeptides comprised in the fusion polypeptide thereof disclosed herein and their derivatives can be used in many fields similar to antibodies or fragments thereof. For example, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, muteins or polypeptides thereof of the disclosure can serve to detect chemical structures by means of established analytical methods (e.g., ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

D. Exemplary Uses, Applications and Production of the Fusion Polypeptides.

Angiogenesis requires the binding of signaling molecules, such as vascular endothelial growth factor (VEGF), to receptors on the surface of normal endothelial cells. When VEGF and other endothelial growth factors bind to their receptors on endothelial cells, signals within these cells are initiated that promote the growth and survival of new blood vessels. One approach to developing an effective anti-angiogenic treatment modality has been to combine agents that act on different targets involved in angiogenesis, preferably targets that act on well isolated signaling pathways.

The present disclosure, therefore, encompasses the use of a fusion polypeptide comprising two subunits, where a first subunit comprises an immunoglobulin or a functional fragment thereof specific for VEGF-A and a second subunit which comprises a hNGAL mutein specific for Ang-2. In some embodiments, the fusion polypeptide is capable of blocking or contributing to block at least one of such signals that promote the growth and survival of new blood vessels.

In some further embodiments, the fusion polypeptide may be used in combination with one or more further anti-angiogenic agents. As used here, an "anti-angiogenic agent" means any substance capable of inhibiting or interfering with the binding of one of such signaling molecules to its receptor. In some embodiments the anti-angiogenic agent is capable of blocking or contributes to block the one of signals that promotes the growth and survival of new blood vessels.

In some particular embodiments, such further anti-angiogenic agents comprise (i) antagonists of Ang-1, Ang-3, Ang-4 and/or Tie-2; (ii) antagonists of Fltl, KDR, Flt4, VEGF-B, VEGF-C, VEGF-D, VEGF-E, PIGF and/or EG-VEGF; (iii) delta like ligand 4 (DLL4, a vascular-specific Notch ligand) antagonists, (iv) epidermal growth factor receptor (EGFR) antagonists and (v) cytokine inhibitors. In some further embodiments, the DLL4 antagonist may be an anti-DLL4 antibody (e.g., an antiDLL4antibody disclosed in U.S. Patent Application No. 2009/0142354 such as REGN421 and etc.). In some further embodiments, the EGFR antagonist may be an anti-EGFR antibody or small molecule inhibitor of EGFR activity. Other anti-angiogenic agents that may be beneficially administered in combination with the anti-Ang-2 hNGAL muteins of the disclosure include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, and/or to their respective receptors.

In this regard, the present disclosure also includes therapeutic combinations comprising any of the fusion polypeptides mentioned herein and an anti-angiogenic agent such as an antagonist of one or more of DLL4, EGFR, or any of the aforementioned cytokines, wherein the antagonist may be an aptamer, an antisense molecule, a ribozyme, an siRNA, a peptibody, a nanobody, an antibody, an antibody fragment (e.g., Fab fragment; F(ab')$_2$ fragment; Fd fragment; Fv fragment; scFv; dAb fragment; an engineered molecule (such as diabody, triabody, tetrabody, minibody and minimal recognition unit); an antiviral, an antibiotic, an analgesic, a corticosteroids and/or an nonsteroidal anti-inflammatory drug (NSAID).

In some embodiments, said engineered molecule may be an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, a "kappabody" (Ill. et al. "Design and construction of a hybrid immunoglobulin domain with properties of both heavy and light chain variable regions" Protein Eng 10:949-57 (1997)), a "minibody" (Martin et al. "The affinity-selection of a minibody polypeptide inhibitor of human interleukin-6" EMBO J 13:5303-9 (1994)), a "diabody" (Holliger et al. "Diabodies': small bivalent and bispecific antibody fragments" PNAS USA 90:6444-6448 (1993)), a "janusin" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, or an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat Biotech. 2005 Nov. 20 edition).

When combined with one or more additional agents of the disclosure, the fusion polypeptide of the disclosure may be administered prior to, simultaneous with (e.g., in the same formulation or in separate formulations), or subsequent to the administration of the other agent(s). The fusion polypeptide and the anti-angiogenic agent may be administered in combination, including concurrently, concomitantly or in series. In some embodiments, the combinations of the disclosure, the fusion polypeptide of the disclosure and the anti-angiogenic agents, may be included in a single composition that may be administered. The composition may include an effective amount of the fusion polypeptide of the disclosure and the anti-angiogenic agent as active ingredients, in association with at least one pharmaceutically acceptable adjuvant, diluent or carrier. In this regard, the combinations of the disclosure can be formulated into compositions using pharmaceutically acceptable ingredients as well as established methods of preparation (Gennaro and Gennaro (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used.

The fusion polypeptide of the disclosure and the anti-angiogenic agent may also be administered independent from each other, including at individual intervals at independent points of time. The combinations of the fusion polypeptide of the disclosure and the anti-angiogenic agent may be provided in various forms and in any orientation.

The fusion polypeptide of the disclosure and combinations thereof may also be administered as part of a treatment regimen that also includes radiation treatment and/or conventional chemotherapy.

In some particular embodiments, the anti-angiogenic agent is an antagonist of any component of the VEGF/VEGF receptor systems and Angiopoietin/Tie-2 receptor system; that is any one of Fltl, KDR, Flt4, VEGF-A, VEGF-B, VEGF-C, VEGF-D, VEGF-E, PlGF, EG-VEGF, Ang-1, Ang-2, Ang-3, Ang-4 or Tie-2. The VEGF-VEGFR pathway and the Tie-2 pathway should be considered as two independent mediators essential for the process of in vivo angiogenesis (Siemeister, G., et al., Cancer Res. 59:3 (1999) 3185-91; Jendreyko, N., et al., Journal of Biological Chemistry, 278:47812-47819 (2003); Jendreyko, N., et al., PNAS, 102:8293-8298 (2005)).

In some embodiments, the present disclosure encompasses the use of (i) a fusion polypeptide of the disclosure and (ii) one or more anti-angiogenic agents, for inhibiting deregulated angiogenesis in a subject. Such use includes a step of administering to a subject an effective amount of (i) a fusion polypeptide of the disclosure and (ii) one or more anti-angiogenic agents.

Similarly, the present disclosure discloses the use of (i) fusion polypeptide of the disclosure and (ii) one or more anti-angiogenic agents for the treatment, prevention or alleviation of diseases or disorders associated with deregulated angiogenesis in a subject. In some further embodiments, the diseases or disorders associated with deregulated angiogenesis include cancer, ocular neovascular diseases (such as retinopathies), arthritis, and psoriasis. In some embodiments, one anti-angiogenic agent is a VEGF-A antagonist mentioned herein and the second anti-angiogenic agent is a VEGF-C antagonist mentioned herein.

Further details on fusion polypeptides of the disclosure comprising a subunit with a detectable affinity for Ang-2 can be found in Section B of the current disclosure.

In a particularly preferred embodiment, a fusion polypeptide that comprises a subunit specific for Ang-2 is selected from the group consisting of SEQ ID NOs: 2, 3, 86, 87, 88, 89, 90, 91, 92, 93, 94, 95, 96 or 97 or functional fragments or variants thereof. In some embodiments, such fragments or variants are structural homologues of a mutein defined in any one of SEQ ID NO: 1.

The present disclosure also relates to a pharmaceutical composition comprising at least one of the following: (i) a fusion polypeptide of the disclosure and (ii) one or more anti-angiogenic agents, which composition can be used in for inhibiting deregulated angiogenesis. In some embodiments, one anti-angiogenic agent is a VEGF-A antagonist mentioned herein and the second anti-angiogenic agent is a VEGF-C antagonist mentioned herein.

In this regard, the combinations of the disclosure can be formulated into compositions using pharmaceutically acceptable ingredients as well as established methods of preparation (Gennaro and Gennaro (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used.

In still another aspect, the present disclosure features a method of treating, preventing or ameliorating diseases or disorders associated with deregulated angiogenesis in a subject, comprising administering to said subject an effective amount of a composition that comprises at least the following: (i) a fusion polypeptide of the disclosure and (ii) one or more anti-angiogenic agents. In some further embodiments, the diseases or disorders associated with deregulated angiogenesis include cancer, ocular neovascular diseases (such as retinopathies), arthritis, and psoriasis. In some embodiments, one anti-angiogenic agent is a VEGF-A antagonist mentioned herein and the second anti-angiogenic agent is a VEGF-C antagonist mentioned herein.

In still another aspect, the present disclosure involves a method of inhibiting or reducing deregulated angiogenesis in a subject comprising administering to said subject an effective amount of a composition that comprises at least the following: (i) a fusion polypeptide of the disclosure and (ii) one or more anti-angiogenic agents.

The invention is further characterized by following items:

Item 1. A fusion polypeptide comprising a first subunit and a second subunit, wherein the first subunit is comprised of an immunoglobulin or an antigen-binding domain thereof specific for VEGF-A, wherein the second subunit is comprised of a human neutrophil gelatinase associated lipocalin (hNGAL) mutein specific for Ang-2.

Item 2. The fusion polypeptide of item 1, wherein the fusion polypeptide is capable of binding VEGF-A with an EC50 value of about 1 nM or lower.

Item 3. The fusion polypeptide of item 1, wherein the fusion polypeptide is capable of binding VEGF-A with an EC50 value of about 1 nM or lower, when measured in an ELISA assay essentially described in Example 2.

Item 4. The fusion polypeptide of item 1, wherein the fusion polypeptide is capable of binding VEGF-A with an EC50 value of about 200 pM or lower.

Item 5. The fusion polypeptide of item 1, wherein the fusion polypeptide is capable of binding VEGF-A with an EC50 value of about 200 pM or lower, when measured in an ELISA assay as essentially described in Example 2.

Item 6. The fusion polypeptide of item 1, wherein the fusion polypeptide is capable of binding Ang-2 with an EC50 value of about 1 nM or lower.

Item 7. The fusion polypeptide of item 1, wherein the fusion polypeptide is capable of binding Ang-2 with an EC50 value of about 1 nM or lower, when measured in an ELISA assay as essentially described in Example 3.

Item 8. The fusion polypeptide of item 1, wherein the fusion polypeptide is capable of binding Ang-2 with an EC50 value of about 250 pM or lower.

Item 9. The fusion polypeptide of item 1, wherein the fusion polypeptide is capable of binding Ang-2 with an EC50 value of about 250 pM or lower, when measured in an ELISA assay as essentially described in Example 3.

Item 10. The fusion polypeptide of item 1, wherein the fusion polypeptide is capable of simultaneously binding VEGF-A and Ang-2, wherein the subunit binding VEGF-A can bind its target with an EC50 value of about 1 nM or lower.

Item 11. The fusion polypeptide of item 1, wherein the fusion polypeptide is capable of simultaneously binding VEGF-A and Ang-2, wherein the subunit binding VEGF-A can bind its target with an EC50 value of about 1 nM or lower, when measured in an ELISA assay as essentially described in Example 4.

Item 12. The fusion polypeptide of item 1, wherein the fusion polypeptide is capable of simultaneously binding VEGF-A and Ang-2, wherein the subunit binding VEGF-A can bind its target with an EC50 value of about 500 pM or lower.

Item 13. The fusion polypeptide of item 1, wherein the fusion polypeptide is capable of simultaneously binding VEGF-A and Ang-2, wherein the subunit binding VEGF-A can bind its target with an EC50 value of about 500 pM or lower, when measured in an ELISA assay as essentially described in Example 4.

Item 14. The fusion polypeptide of item 1, wherein the fusion polypeptide is capable of simultaneously binding VEGF-A and Ang-2, wherein the subunit binding Ang-2 can bind its target with an EC50 value of about 1.5 nM or lower.

Item 15. The fusion polypeptide of item 1, wherein the fusion polypeptide is capable of simultaneously binding VEGF-A and Ang-2, wherein the subunit binding Ang-2 can bind its target with an EC50 value of about 1.5 nM or lower, when measured in an ELISA assay as essentially described in Example 4.

Item 16. The fusion polypeptide of item 1, wherein the fusion polypeptide is capable of simultaneously binding VEGF-A and Ang-2, wherein the subunit binding Ang-2 can bind its target with an EC50 value of about 600 pM or lower.

Item 17. The fusion polypeptide of item 1, wherein the fusion polypeptide is capable of simultaneously binding VEGF-A and Ang-2, wherein the subunit binding Ang-2 can bind its target with an EC50 value of about 600 pM or lower, when measured in an ELISA assay as essentially described in Example 4.

Item 18. The fusion polypeptide of item 1, wherein the fusion polypeptide is capable of blocking the binding of human Ang-2 to human Tie-2 with an EC50 value of about 1 nM or lower.

Item 19. The fusion polypeptide of item 1, wherein the fusion polypeptide is capable of blocking the binding of human Ang-2 to human Tie-2 with an EC50 value of about 1 nM or lower in a competition cell ECL format as essentially described in Example 5.

Item 20. The fusion polypeptide of item 1, wherein the fusion polypeptide is capable of reducing or blocking at least one of the biological functions of VEGF-A.

Item 21. The fusion polypeptide of item 1, wherein the fusion polypeptide is capable of reducing or blocking at least one of the biological functions of VEGF-A, in particular VEGF-A-dependent cell-proliferation such as measured in a functional cell-based proliferation assay essentially described in Example 6.

Item 22. The fusion polypeptide of item 1, wherein the fusion polypeptide has a half-life in a rabbit of about 3 to 5 days.

Item 23. The fusion polypeptide of item 1, wherein the fusion polypeptide has a half-life in a rabbit of about 3 to 5 days, such as measured in a pharmacokinetics assay essentially described in Example 7.

Item 24. The fusion polypeptide of item 1, wherein the fusion polypeptide has a half-life in a human subject of about 3 to 5 days.

Item 25. The fusion polypeptide of any one of the preceding items, wherein said mutein comprises one or more mutated amino acid residues at positions corresponding to positions 28, 36, 40, 41, 49, 52, 65, 68, 70, 72-74, 77, 79, 81, 87, 96, 100, 103, 106, 116, 125, 126, 127, 129, 132 and 134 of the linear polypeptide sequence of the mature hNGAL (SEQ ID NO: 1).

Item 26. The fusion polypeptide of any one of the preceding items, wherein said mutein comprises one or more mutated amino acid residues at positions 36, 40, 41, 49, 52, 68, 70, 72-73, 77, 79, 81, 96, 100, 103, 106, 125, 127, 132 and 134 of the linear polypeptide sequence of the mature hNGAL.

Item 27. The fusion polypeptide of any one of the preceding items, wherein said mutein comprises one of the following sets of amino acid substitutions in comparison with the linear polypeptide sequence of the mature hNGAL: Leu 36→Gln, Glu, His, Val, Met or Phe; Ala 40→Val, Tyr, His or Trp; Ile 41→His, Tyr, Trp or Val; Gln 49→Gly, Ile, Val, Glu or Val; Tyr 52→Trp, His, Thr or Ser; Ser 68→Gly, Asp, Gln, Glu or Ile; Leu 70→Ser, Thr, Gly, Arg, Tyr or Ala; Arg 72→Gly, Ala, Trp, Thr or Glu; Lys 73→Pro, Phe, Leu, Arg, Ala or Gln; Asp 77→Asn, Lys, Ser or Val; Trp 79→Thr, Arg, Ser or Asn; Arg 81→Trp, His or Tyr; Asn 96→Gly, Ala, Pro, Gln or Asp; Tyr 100→Pro, Trp, Gly, Ser, Leu or Asp; Leu 103→Gly, Glu, Asp, Met or Gln; Tyr 106→Thr, Leu or Phe; Lys 125→His, Thr or Gly; Ser 127→Leu or Met; Tyr 132→Phe, Trp or Val; and Lys 134→Ala, Glu or Trp.

Item 28. The fusion polypeptide any one of the preceding items, wherein said mutein comprises one of the following sets of mutated amino acid substitutions in comparison with the linear polypeptide sequence of the mature hNGAL: Gln 28→His; Asn 65→Asp; Lys 74→Glu; Cys 87→Ser; Asn 116→Asp; Val 126→Met and Asn 129→Asp.

Item 29. The fusion polypeptide any one of the preceding items, wherein said mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 40, 41, 49, 52, 65, 68, 70, 72-74, 77, 79, 81, 87, 96, 100, 103, 106, 116, 125, 126, 127, 129, 132 and 134 of the linear polypeptide sequence of the mature hNGAL (SEQ ID NO: 1).

Item 30. The fusion polypeptide any one of the preceding items, wherein said mutein comprises one of the following sets of amino acid substitutions in comparison with the linear polypeptide sequence of the mature hNGAL:
- (a) Leu 36→Gln; Ala 40→Tyr; Gln 49→Gly; Tyr 52→Trp; Ser 68→Gly; Leu 70→Ser; Arg 72→Gly; Lys 73→Pro; Asp 77→Asn; Trp 79→Thr; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;
- (b) Leu 36→Phe; Ala 40→His; Ile 41→Arg; Gln 49→Gly; Tyr 52→His; Ser 68→Asp; Leu 70→Thr; Arg 72→Ala; Lys 73→Phe; Asp 77→Asn; Trp 79→Arg; Arg 81→His; Tyr 100→Trp; Leu 103→Glu; Tyr 106→Thr; Lys 125→Thr; Ser 127→Met; Tyr 132→Trp; Lys 134→Trp;
- (c) Leu 36→Val; Ala 40→Trp; Ile 41→Tyr; Gln 49→Ile; Tyr 52→Thr; Ser 68→Gln; Leu 70→Gly; Arg 72→Glu; Lys 73→Gln; Asp 77→Lys; Trp 79→Ser; Arg 81→His; Tyr 100→Trp; Leu 103→Asp; Tyr 106→Leu; Lys 125→Gly; Ser 127→Met; Tyr 132→Val; Lys 134→Ala;
- (d) Leu 36→Glu, Ala 40 Val; Ile 41→Glu; Gln 49→Val; Tyr 52→ThrSer68→Glu; Leu70→Arg; Arg72→Trp; Lys73→Leu; Asp77→Lys; Trp 79→Asn; Arg 81→His; Asn 96→Ala; Tyr 100→Gly; Leu 103→Met; Tyr 106→Thr; Lys 125→Thr; Ser 127→Met; Tyr 132→Trp; Lys 134→Trp;
- (e) Leu 36→Gln; Ala 40→Tyr; Ile 41→Trp; Gln 49→Ile; Tyr 52→Ser; Ser 68→Ile; Leu 70→Tyr; Arg 72→Thr; Lys 73→Arg; Asp 77→Ser; Trp 79→Arg; Arg 81→Tyr; Asn 96→Pro; Leu 103→Asp; Tyr 106→Thr; Lys 125→His; Ser 127→Tyr; Tyr 132→Trp; Lys 134→Glu;
- (f) Leu 36→Gln; Ala 40→Tyr; Gln 49→Glu; Tyr 52→Trp; Asn 65→Asp; Ser 68→Gly; Leu 70→Ser; Arg 72→Gly; Lys 73→Pro; Asp 77→Asn; Trp 79→Arg; Arg 81→Trp; Asn 96→Gly; Tyr 100→Ser;

Leu 103→Gln; Tyr 106→Thr; Lys 125→His; Ser 127→Leu; Tyr 132→Phe; Lys 134→Glu;
(g) Leu 36→His; Ala 40 Tyr; Gln 49→Glu; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Pro; Leu 103→Asp; Tyr 106→Thr; Lys 125→His; Ser 127→Leu; Tyr 132→Phe; Lys 134→Glu;
(h) Leu 36→Gln; Ala 40 Tyr; Gln 49→Gly; Tyr 52→Trp; Asn 65→Asp; Ser 68→Glu; Leu 70→Ser; Arg 72→Gly; Lys 73→Ala; Asp 77→Asn; Trp 79→Arg; Arg 81→Trp; Asn 96→Gly; Tyr 100→Asp; Leu 103→Gly; Tyr 106→Thr; Lys 125→His; Ser 127→Leu; Tyr 132→Phe; Lys 134→Glu;
(i) Leu 36→His; Ala 40 Tyr; Gln 49→Gly; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;
(j) Leu 36→Gln; Ala 40 Tyr; Gln 49→Gly; Tyr 52→Trp; Asn 65→Asp; Ser 68→Gly; Leu 70→Ser; Arg 72→Gly; Lys 73→Ala; Asp 77→Val; Trp 79→Arg; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;
(k) Leu 36→Gln; Ala 40 Tyr; Gln 49→Val; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Leu; Leu 103→Gly; Tyr 106→Thr; Lys 125→His; Ser 127→Leu; Tyr 132→Phe; Lys 134→Glu;
(l) Leu 36→Val; Ala 40 Tyr; Ile 41→Tyr; Gln 49→Ile; Tyr 52→Thr; Asn 65→Asp; Ser 68→Gln; Leu 70→Gly; Arg 72→Glu; Lys 73-Gln; Lys 74→Glu; Asp 77→Lys; Trp 79→Ser; Arg 81→His; Tyr 100→Trp; Leu 103→Asp; Tyr 106→Pro; Asn 116→Asp; Lys 125→Gly; Ser 127→Met; Asn 129→Asp; Tyr 132→Val; Lys 134→Ala;
(m) Leu 36→Val; Ala 40 Tyr; Ile 41→Tyr; Gln 49→Ile; Tyr 52→Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Asn 96→Asp; Tyr 100→Trp; Leu 103→Asp; Tyr 106→Pro; Lys 125→Gly; Val 126→Met; Ser 127→Met; Asn 129→Asp; Tyr 132→Val; Lys→134→Ala; or
(n) Leu 36→Met; Ala 40 Tyr; Ile 41→Asp; Gln 49→Ile; Tyr 52→Thr; Asn 65→Asp; Ser 68→Gln; Leu 70→Gly; Arg 72→Glu; Lys 73→Gln; Asp 77→Lys; Trp 79→Ser; Arg 81→His; Asn 96→Gln; Tyr 100→Trp; Leu 103→Asp; Tyr 106→Pro; Lys 125→Gly; Ser 127→Met; Tyr 132→Val; Lys 134→Ala;

wherein each of the sets of amino acid substitutions optionally further includes the substitutions Gln 28→His and Cys 87→Ser.

Item 31. The fusion polypeptide any one of the preceding items, wherein the second subunit comprises a mutein with an amino acid sequence selected from the group consisting of SEQ ID NOs: 2 and 3 and functional fragments or variants thereof.

Item 32. The fusion polypeptide any one of the preceding items, wherein the amino acid sequence of the mutein has at least 85%, at least 90%, at least 95%, at least 97%, or at least 98% sequence identity to an amino acid sequence selected from the group consisting of SEQ ID NOs: 2 and 3.

Item 33. The fusion polypeptide any one of the preceding items, wherein one or more subunits have one or more elements which are conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

Item 34. The fusion polypeptide of item 33, wherein the second subunit comprises a mutein which is cross-reactive with both human Ang-2 and mouse Ang-2.

Item 35. The fusion polypeptide of item 34, wherein the second subunit comprises a mutein capable of binding mouse Ang-2 with an affinity measured by an EC50 value of about 5 nM or lower.

Item 36. The fusion polypeptide of item 34, wherein the second subunit comprises a mutein capable of binding mouse Ang-2 with an affinity measured by an EC50 value of about 5 nM or lower, when measured in a standard ELISA assay.

Item 37. The fusion polypeptide of any one of the preceding items, wherein the mutein from the second subunit can be conjugated to a compound that extends the serum half-life of the polypeptide.

Item 38. The fusion polypeptide of item 37, wherein the compound that extends the serum half-life is selected from the group consisting of a polyalkylene glycol molecule, hydroethylstarch, a Fc part of an immunoglobulin, a CH3 domain of an immunoglobulin, a CH4 domain of an immunoglobulin, an albumin binding peptide, and an albumin binding protein.

Item 39. The fusion polypeptide of item 38, wherein the polyalkylene glycol is polyethylene (PEG) or an activated derivative thereof.

Item 40. The fusion polypeptide of any one of the preceding items, wherein said first and second subunits are linked via a peptide bond.

Item 41. The fusion polypeptide of any one of the preceding items, wherein the first subunit and the second subunit are linked via a peptide bond between the N-terminus of the lipocalin mutein of the second subunit and the C-terminus of a heavy chain constant region (CH) of the immunoglobulin of the first subunit.

Item 42. The fusion polypeptide of any one of the preceding items, wherein the first subunit is linked to the second subunit via a peptide bond between the N-terminus of the lipocalin mutein of the second subunit and the C-terminus of a light chain constant region (CL) of the immunoglobulin of the first subunit.

Item 43. The fusion polypeptide of any one of the preceding items, wherein the first subunit is linked to the second subunit via a peptide bond between the C-terminus of the lipocalin mutein of the second subunit and the N-terminus of a light chain constant region (CH) of the immunoglobulin of the first subunit.

Item 44. The fusion polypeptide of any one of the preceding items, wherein the first subunit is linked to the second subunit via a peptide bond between the C-terminus of the lipocalin mutein of the second subunit and the N-terminus of a light chain constant region (CL) of the immunoglobulin of the first subunit.

Item 45. The fusion polypeptide of any one of the preceding items, wherein the peptide bond is provided by an (G4S)3 peptide linker.

Item 46. The fusion polypeptide of any one of the preceding items, wherein the peptide bond comprises at least 4 glycine residues and at least one serine residue.

Item 47. The fusion polypeptide of any one of the preceding items, wherein the peptide bond comprises at least one (G4S) unit.

Item 48. The fusion polypeptide of item 48, wherein said (G4S) unit can be repeated n times, where n=1-10.

Item 49. The fusion polypeptide of any one of the preceding items, wherein the immunoglobulin is a monoclonal antibody.

Item 50. The fusion polypeptide of item 51, wherein the monoclonal antibody has the heavy chain complementarity-determining regions (CDRs) contained in the heavy chain of SEQ ID NO: 8 and the light chain CDRs contained in the light chain of SEQ ID NO 9.

Item 51. The fusion polypeptide of any one of the preceding items, wherein the monoclonal antibody has a heavy chain determined by SEQ ID NO: 8 and a light chain determined by SEQ ID NO 9.

Item 52. The fusion polypeptide of any one of the preceding items, wherein the monoclonal antibody has an IgG1 backbone.

Item 53. The fusion polypeptide of any one of the preceding items, wherein the monoclonal antibody is bevacizumab.

Item 54. The fusion polypeptide of any one of the preceding items, wherein said polypeptide comprises the amino acids shown in SEQ ID NO: 9 and 10, or the amino acids shown in SEQ ID NO: 8 and 11, or the amino acids shown in SEQ ID NO: 9 and 12, or the amino acids shown in SEQ ID NO: 8 and 13, or the amino acids shown in SEQ ID NO: 9 and 14, or the amino acids shown in SEQ ID NO: 8 and 15, or the amino acids shown in SEQ ID NO: 9 and 16, or the amino acids shown in SEQ ID NO: 8 and 17.

Item 55. A nucleic acid molecule comprising a nucleotide sequence encoding the polypeptide of any one of items 1 to 54.

Item 56. The nucleic acid molecule of item 55, wherein the nucleic acid molecule is operably linked to a regulatory sequence to allow expression of said nucleic acid molecule.

Item 57. The nucleic acid molecule of any one of items 55-56, wherein the nucleic acid molecule is comprised in a vector or in a phagemid vector.

Item 58. A host cell containing a nucleic acid molecule of any one of items 56-57.

Item 59. A method of producing the fusion polypeptide of any one of the preceding items, comprising the step of expressing the nucleic acid sequence coding for the mutein.

Item 60. The method of item 59, wherein the fusion polypeptide is produced in a bacterial or eukaryotic host organism and is isolated from this host organism or its culture.

Item 61. A pharmaceutical composition comprising the fusion polypeptide of any one of items 1-54.

Item 62. A use of the fusion polypeptide of any one of items 1-54 for the manufacture of a pharmaceutical composition suited for the treatment, prevention and/or amelioration of a disease or disorder associated with deregulated angiogenesis.

Item 63. A use of the fusion polypeptide of any one of items 1-54 for the simultaneous binding of Ang-2 and VEGF-A in a subject.

Item 64. A use of the fusion polypeptide of any one of items 1-54 or a composition comprising such fusion polypeptide for the simultaneous binding of Ang-2 and VEGF-A in a subject.

Item 65. A use of the fusion polypeptide of any one of items 1-54 or a composition comprising such fusion polypeptide for inhibiting angiogenesis in a subject.

Item 66. A use of the polypeptide of any one of items 1-54 or a composition comprising such fusion polypeptide for treating a patient suffering from "wet" type of age-related macular degeneration (ARMD).

Item 67. A use of the polypeptide of any one of items 1-54 or a composition comprising such fusion polypeptide in the detection of angiogenesis factors for diagnostic purposes.

Item 69. A method of simultaneously binding Ang-2 and VEGF-A in a subject comprising administering to said subject the fusion polypeptides of any one of items 1-54 or a composition comprising such fusion polypeptide.

Item 70. A method of inhibiting or reducing angiogenesis in a subject, comprising administering to said subject an effective amount of the fusion polypeptide of any one of items 1-54 or a composition comprising such fusion polypeptide.

Item 71. A method of treating, preventing or ameliorating a disease or disorder associated with deregulated angiogenesis in a subject, comprising administering to said subject an effective amount of the fusion polypeptide of any one of items 1-54 or a composition comprising such fusion polypeptide.

Item 72. The method of item 71 or the use item 62, wherein the disease or disorder is selected from the group consisting of: tumor growth, eye disorders, vascular diseases, inflammatory or infectious diseases, cancer, ocular neovascular diseases, arthritis, and psoriasis.

Item 73. A diagnostic or analytical kit comprising a fusion polypeptide according to any one of items 1-54 or a composition comprising such fusion polypeptide.

V. EXAMPLES

Example 1: Expression and Analysis of Fusion Polypeptides

To engage VEGF-A and Ang-2 at the same time, we generated several representative antibody-lipocalin mutein fusion polypeptides, fusing together the antibody having the heavy and light chains provided by SEQ ID NOs: 8 and 9, and one of the lipocalin muteins of SEQ ID NO: 2 or SEQ ID NO: 3 via an unstructured (G4S)3 linker (SEQ ID NO: 19). The different formats that were designed are depicted in FIG. 1. Such fusion polypeptides (SEQ ID NOs: 9 and 10, SEQ ID NOs: 8 and 11, SEQ ID NOs: 9 and 14, SEQ ID NOs: 8 and 15) were generated via fusion of the one of the lipocalin muteins of SEQ ID NO: 2 or SEQ ID NO: 3 to either one of the two C-termini of the antibody.

The constructs were generated by gene synthesis and cloned into a mammalian expression vector. They were then transiently expressed in CHO cells. The concentration of fusion polypeptides in the cell culture medium was measured using a ForteBio Protein A sensor (Pall Corp.) and quantified using a human IgG1 standard.

The fusion polypeptides were purified using Protein A chromatography followed by size-exclusion chromatography (SEC) in phosphate-buffered saline (PBS). After SEC purification the fractions containing monomeric protein were pooled and analyzed again using analytical SEC. According to this analysis, the fusion polypeptides were fully monomeric without detectable multimeric species or aggregates.

Example 2: Specificity of Fusion Polypeptides Towards VEGF-A

We employed an ELISA assay to determine the affinity of the fusion proteins to recombinant VEGF-A. The target was dissolved in PBS (5 μg/mL) and coated overnight on microtiter plates at 4° C. The plate was washed after each incubation step with 80 μL PBS supplemented with 0.05% (v/v) Tween 20 (PBS-T) five times. The plates were blocked with 2% BSA (w/v) in PBS for 1 h at room temperature and subsequently washed. Different concentrations of the benchmark bispecific antibody (SEQ ID NOs: 20, 21, 22 and 23) and positive control antibody (SEQ ID NOs: 8 and 9) or the fusion polypeptides (SEQ ID NOs: 9 and 10, SEQ ID NOs: 8 and 11, SEQ ID NOs: 9 and 14, SEQ ID NOs: 8 and 15) were added to the wells and incubated for 1 h at room temperature, followed by a wash step. Bound agents under study were detected after incubation with 1:5000 diluted anti-human IgG Fc-HRP (#109-035-098, Jackson Laboratory) in PBS-T. After an additional wash step, fluorogenic HRP substrate (QuantaBlu, Thermo) was added to each well and the fluorescence intensity was detected using a fluorescence microplate reader.

The result of the experiment was plotted in FIG. 2, together with the fit curves resulting from a 1:1 binding sigmoidal fit, where the EC50 value and the maximum signal were free parameters, and the slope was fixed to unity. The observed EC50 values were in a similar range for all tested fusion polypeptides and benchmark antibodies (0.8-0.15 nM).

Example 3: Specificity of Fusion Polypeptides Towards Ang-2

We employed an ELISA assay to determine the affinity of the fusion polypeptides and the positive control lipocalin muteins of SEQ ID NO: 2 or SEQ ID NO: 3 to recombinant human Ang-2 (Creative BioMart). The target was dissolved in PBS (5 μg/mL) and coated overnight on microtiter plates at 4° C. The plate was washed after each incubation step with 80 μL PBS-T five times. The plates were blocked with 2% BSA (w/v) in PBS for 1 h at room temperature and subsequently washed. Different concentrations of the Ang-2-specific lipocalin mutein in monomeric form (SEQ ID NO: 2 or SEQ ID NO: 3) or the fusion polypeptides (SEQ ID NOs: 9 and 10, SEQ ID NOs: 8 and 11, SEQ ID NOs: 9 and 14, SEQ ID NOs: 8 and 15) or bispecific benchmark control (SEQ ID NOs: 20, 21, 22 and 23) were added to the wells and incubated for 1 h at room temperature, followed by a wash step. Bound agents under study were detected after incubation for 1 h at room temperature with 1:1000 diluted anti-lipocalin antibody conjugated to HRP in PBS-T or 1:5000 diluted anti-human IgG Fc-HRP (#109-035-098, Jackson Laboratory) in PBS-T. After an additional wash step, fluorogenic HRP substrate (QuantaBlu, Thermo) was added to each well and the fluorescence intensity was detected using a fluorescence microplate reader.

The result of the experiment was plotted in FIG. 3, together with the fit curves resulting from a 1:1 binding sigmoidal fit, where the EC50 value and the maximum signal were free parameters, and the slope was fixed to unity. The observed EC50 values for all tested fusion polypeptides (SEQ ID NOs: 9 and 10, SEQ ID NOs: 8 and 11, SEQ ID NOs: 9 and 14, SEQ ID NOs: 8 and 15) were similar and ranged from 0.21 nM to 0.23 nM. The value obtained for the positive control lipocalin muteins of SEQ ID NO: 2 or SEQ ID NO: 3, was 0.35-0.5 nM while the bispecific benchmark antibody had an EC50 of 0.83 nM.

Example 4: Demonstration of Simultaneous Target Binding in an ELISA-Based Setting In order to demonstrate the simultaneous binding of the fusion polypeptides to VEGF-A and Ang-2, a dual-binding ELISA format was used. Recombinant VEGF-A (R&D Systems) in PBS (5 μg/mL) was coated overnight on microtiter plates at 4° C. The plate was washed five times after each incubation step with 80 μL PBS supplemented with 0.05% (v/v) Tween 20 (PBS-T) using a Biotek ELx405 select CW washer. The plates were blocked with 2% BSA (w/v) in PBS for 1 h at room temperature and subsequently washed again. Different concentrations of the fusion polypeptides were added to the wells and incubated for 1 h at room temperature, followed by a wash step. Subsequently, biotinylated human Ang-2 was added at a constant concentration of 1 μg/mL in PBS-T for 1 h. After washing, Extravidin-HRP (Sigma-Adrich, 1:5000 in PBS-T) was added to the wells for 1 h. After an additional wash step, fluorogenic HRP substrate (QuantaBlu, Thermo) was added to each well and the fluorescence intensity was detected using a fluorescence microplate reader.

Alternatively, recombinant Ang-2 (Creative Bio Mart) in PBS (5 μg/mL) was coated overnight on microtiter plates at 4° C. The plate was washed five times after each incubation step with 80 μL PBS supplemented with 0.05% (v/v) Tween 20 (PBS-T) using a Biotek ELx405 select CW washer. The plates were blocked with 2% BSA (w/v) in PBS for 1 h at room temperature and subsequently washed again. Different concentrations of the fusion polypeptides (SEQ ID NOs: 9 and 10, SEQ ID NOs: 8 and 11, SEQ ID NOs: 9 and 14, SEQ ID NOs: 8 and 15) were added to the wells and incubated for 1 h at room temperature, followed by a wash step. Subsequently, biotinylated human VEGF-A was added at a constant concentration of 1 μg/mL in PBS-T for 1 h. After washing, Extravidin-HRP (Sigma-Adrich, 1:5000 in PBS-T) was added to the wells for 1 h. After an additional wash step, fluorogenic HRP substrate (QuantaBlu, Thermo) was added to each well and the fluorescence intensity was detected using a fluorescence microplate reader.

The respective experimental data was plotted in FIG. 4. All tested fusion polypeptides showed clear binding signals with EC50 values ranging from 0.36-0.55 nM when VEGF-A was coated on the plate, demonstrating that these fusion polypeptides are able to engage VEGF-A and Ang-2 simultaneously. The bispecific benchmark molecule (SEQ ID NOs: 20, 21, 22 and 23) showed a lower binding signal with EC50 value of 1.8 nM (FIG. 4A). Using the alternative assay set up, where Ang-2 was coated on the plate and biotinylated VEGF-A was used for detection, all tested fusion polypeptides showed clear binding signals with EC50 values ranging from 0.95-1.3 nM, while the bispecific benchmark molecule again showed a lower binding signal with EC50 value of 14 nM (FIG. 4B). This inferior binding of the bispecific benchmark antibody may be due to its monovalent target engagement.

Example 5: Fusion Polypeptides Block the Binding of Human Ang-2 to hTie-2 Expressing Cells Binding of fusion polypeptides to human Ang-2 in a competitive mode was tested on hTie-2 overexpressing HEK cells using a competition cell electrochemoluminescence (ECL) assay format (FIG. 5). In this experiment, a constant concentration of human Ang-2 was incubated with variable concentrations of fusion polypeptides (SEQ ID NOs: 9 and 10, SEQ ID NOs: 8 and 11, SEQ ID NOs: 9 and 14, SEQ ID NOs: 8 and 15), positive control lipocalin muteins (SEQ ID NO: 2 or SEQ ID NO: 3), benchmark antibody (SEQ ID NOs: 6 and 7) and negative controls (SEQ ID NO: 1 & hIgG1) for 1 h. After this pre-incubation in solution, an aliquot of the binding moiety/Ang-2 mixture was transferred to an MSD plate coated with hTie-2 overexpressing HEK cells to measure the concentration of hAng-2 that was not blocked to bind to hTie-2 respectively.

All incubation steps were performed at room temperature, and the plate was washed after each incubation step with 80 μl PBS buffer for two times using a Biotek EL405 select CW washer (Biotek). In the first step, a 384 well plate was precoated for 5 minutes with poly D lysine and washed twice with PBS. $10^4$ HEK:hTie-2 cells per well were seeded and allowed to adhere to the surface of the wells overnight at 37° C. After washing, cell coated wells were blocked with 60 μl PBS/Casein (2% Casein in PBS) for 1 h at room temperature.

A fixed concentration of human Ang-2 was incubated in solution with varying concentrations of fusion polypeptides, positive control lipocalin muteins, benchmark antibody and negative controls using a suitable starting concentration which was serially diluted at a 1:3 ratio down to the picomolar range in PBS-/Casein buffer. After 1 h incubation at room temperature, 20 μl of the reaction mixture was transferred to the HEK:hTie2-coated plate to capture competitively unbound hAng-2 for 1 hour min at RT. A standard curve containing varying concentrations of hAng-2 was prepared in PBS/Casein and incubated for 1 hour the same plate as well.

To allow for detection and quantitation of bound hAng-2, the residual supernatants were discarded and 20 μl of a mixture anti-HIS-tag antibody (Abcam) and Sulfotag labelled anti-goat antibody (Mesoscale Discovery) was added at a concentration of 1 μg/ml in PBS/casein and incubated for 1 h at RT. After washing, 35 μl surfactant-free reading buffer was added to each well and the ECL signal of every well was read using a Mesoscale Discovery reader.

The respective experimental data was plotted in FIG. 5. All tested fusion polypeptides showed clear inhibition of hAng-2 binding to hTie2 with EC50 values ranging from 0.3-0.4 nM, while the benchmark molecule and lipocalin muteins also showed similar values of between 0.3-0.6 nM.

Example 6: Fusion Polypeptide-Mediated Blockade of VEGF-A in Cell-Based Proliferation Assay The ability of fusion polypeptides (SEQ ID NOs: 9 and 10, SEQ ID NOs: 8 and 11, SEQ ID NOs: 9 and 14, SEQ ID NOs: 8 and 15), positive control lipocalin muteins (SEQ ID NO: 2 or SEQ ID NO: 3), benchmark antibodies (SEQ ID NOs: 6 and 7; SEQ ID NO: 8 and 9) and negative controls (SEQ ID NO: 1 & hIgG1) to neutralize the biological activity of VEGF-A was assessed by the application of a short-term proliferation bioassay employing lymphatic microvascular endothelial cells (LEC). The LEC proliferation can be inhibited by agents having either a hVEGF-A or hAng-2-neutralizing effect. While hAng-2 is not directly added to the assay endogenous hAng-2 is released by the LEC cells.

LEC were maintained in EBM, 5% fetal calf serum and MV2 supplemental kit under standard conditions according to manufacturer's instructions (PAA Laboratories), 37° C., 5% $CO_2$ atmosphere). On day 1 of the experiment, the adherent cells were dissociated from their substrate with trypsin/EDTA according to the manufacturer's instructions. Subsequently, cells were centrifuged down for 5 minutes at 1000 rpm, resuspended in EBM and filtered through a 100 μm cell strainer (Falcon) to remove cell aggregates. Cells were then seeded in 96-well flat bottom tissue culture plates (Greiner) at a density of 3200 cells per well using an end volume of 100 μl. They were incubated 1 hour under standard conditions. After 1 h dilution series of all test agents (pre-incubated with hVEGF-A (R&D systems) at 50 ng/ml for 30 minutes) were added to LEC cells in culture. After three days in culture, the extent of proliferation was assessed by quantifying the number of viable cells. This was performed using the CellTiter-Glo Luminescent Cell Viability Assay (Promega) to measure ATP levels, which correlate with the number of metabolically active cells. The ability of fusion polypeptides (SEQ ID NOs: 9 and 10, SEQ ID NOs: 8 and 11, SEQ ID NOs: 9 and 14, SEQ ID NOs: 8 and 15) and VEGF-A specific benchmark (SEQ ID NO: 8 and 9) to neutralize VEGF-A induced proliferation was assessed. The ability of Ang-2 specific lipocalin muteins (SEQ ID NO: 2 or SEQ ID NO: 3) and benchmark antibody (SEQ ID NOs: 6 and 7) to neutralize hAng-2 was also assessed by their 1050 value, i.e. the concentration of the lipocalin muteins that lead to half-maximal inhibition of hAng-2 mediated proliferation.

IC50 values were determined using GraphPad Prism software (GraphPad Software Inc.) by plotting standardized signal against samples concentration and non-linear regression of the data with a sigmoidal dose-response model.

The respective experimental data was plotted in FIG. 6. All tested fusion polypeptides showed clear inhibition of proliferation with EC50 values ranging from 1.2-0.5 nM, while the VEGF-A benchmark molecule had an EC50 of 1.2. The hAng-2 specific lipocalin muteins and hAng-2 benchmark control (SEQ ID NOs: 6 and 7) partially inhibited proliferation with IC50 values between 1.2-4.2 nM. The negative controls had no effect on proliferation.

Example 7: In Vivo Pharmacokinetic Assessment of Fusion Polypeptides

The in vivo assessment of fusion polypeptides involved intravitreal injection of test agent in rabbits (HY79b; pigmented) followed by sampling of blood, vitreous humor and retinal tissue over a 336-hour period. In brief, rabbits (n=16 per treatment) were injected of 100 ug fusion polypeptide (SEQ ID NOs: 9 and 14, SEQ ID NOs: 8 and 15) into one eye (right) while the other eye (left) was used a control (i.e., untreated). Ophthalmic examinations were performed periodically to assess the overall health of the rabbits' eyes.

Pharmacokinetics of test agents was determined based on plasma and vitreous humor collected from rabbits over a 336-hour period following injection. In particular, blood and vitreous humor was collected from rabbits at 2 h, 8 h, 24 h, 72 h, 96 h, 168 h, 216 h and 336 h post-dose (n=2 rabbits per treatment sacrificed at each time point).

Drug levels were detected using a Sandwich ELISA detecting the full bispecific construct via the targets VEGF-A and Ang-2, as described in example 4. The data were fitted using a non-compartmental model using Prism GraphPad 5 software. FIG. 7 shows linear plots of the vitreal concentration over time for the constructs SEQ ID NOs: 9 and 14, SEQ ID NOs: 8 and 15. The data show that the bispecific fusions have terminal half-lives in rabbit vitreous ranging from approximately 3.7-4.5 days.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and sub-generic groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

Equivalents: Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A fusion protein comprising a first subunit and a second subunit, wherein the first subunit is comprised of an immunoglobulin or an antigen-binding domain thereof specific for vascular endothelial growth factor A (VEGF-A), wherein the second subunit is comprised of a human neutrophil gelatinase-associated lipocalin (hNGAL) mutein specific for angiopoietin-2 (Ang-2); wherein said mutein comprises one or more of the following mutated amino acid residues in comparison with the linear polypeptide sequence of mature hNGAL (SEQ ID NO: 1): Leu 36→Gln, Glu, His, Val, Met or Phe; Ala 40→Val, Tyr, His or Trp; Ile 41→His, Tyr, Trp, Val, Arg, Glu, or Asp; Gln 49→Gly, Ile, Glu or Val; Tyr 52→Trp, His, Thr or Ser; Ser 68→Gly, Asp, Gln, Glu or Ile; Leu 70→Ser, Thr, Gly, Arg, Tyr or Ala; Arg 72→Gly, Ala, Trp, Thr or Glu; Lys 73→Pro, Phe, Leu, Arg, Ala or Gln; Asp 77→Asn, Lys, Ser or Val; Trp 79→Thr, Arg, Ser or Asn; Arg 81→Trp, His or Tyr; Asn 96→Gly, Ala, Pro, Gln or Asp; Tyr 100→Pro, Trp, Gly, Ser, Leu or Asp; Leu 103→Gly, Glu, Asp, Met or Gln; Tyr 106→Thr, Leu, Phe, or Pro; Lys 125→His, Thr or Gly; Ser 127→Leu, Met, or Tyr; Tyr 132→Phe, Trp or Val; and Lys 134→Ala, Glu or Trp; and
wherein the second subunit is fused to the C-terminus of the immunoglobulin heavy chain constant region (CH) or light chain constant region (CL) of the first subunit via a peptide linker.

2. The fusion protein of claim 1, wherein the fusion protein is capable of binding VEGF-A with an EC50 value of about 1 nM or lower.

3. The fusion protein of claim 1, wherein the fusion protein is capable of binding Ang-2 with an EC50 value of about 1 nM or lower.

4. The fusion protein of claim 1, wherein the fusion protein is capable of simultaneously binding VEGF-A and Ang-2.

5. The fusion protein of claim 1, wherein the fusion protein is capable of simultaneously binding VEGF-A and Ang-2, wherein the subunit binding VEGF-A can bind its target with an EC50 value of about 1 nM or lower, wherein the subunit binding Ang-2 can bind its target with an EC50 value of about 1.5 nM or lower.

6. The fusion protein of claim 1, wherein said mutein comprises one or more of the following mutated amino acid residues in comparison with the linear polypeptide sequence of mature hNGAL (SEQ ID NO: 1): Gln28→His; Asn 65→Asp; Lys 74→Glu; Cys 87→Ser; Asn 116→Asp; Val 126→Met; and Asn 129→Asp.

7. The fusion protein of claim 1, wherein said mutein comprises one of the following sets of mutated amino acid residues in comparison with the linear polypeptide sequence of mature hNGAL (SEQ ID NO: 1):

(a) Leu 36→Gln; Ala 40→Tyr; Gln 49→Gly; Tyr 52→Trp; Ser 68→Gly; Leu 70→Ser; Arg 72→Gly; Lys 73→Pro; Asp 77→Asn; Trp 79→Thr; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;

(b) Leu 36→Phe; Ala 40→His; Ile 41→Arg; Gln 49→Gly; Tyr 52→His; Ser 68→Asp; Leu 70→Thr; Arg 72→Ala; Lys 73→Phe; Asp 77→Asn; Trp 79→Arg; Arg 81→His; Tyr 100→Trp; Leu 103→Glu; Tyr 106→Thr; Lys 125 Thr; Ser 127→Met; Tyr 132→Trp; Lys 134→Trp;

(c) Leu 36→Val; Ala 40→Trp; Ile 41→Tyr; Gln 49→Ile; Tyr 52 Thr; Ser 68→Gln; Leu 70→Gly; Arg 72→Glu; Lys 73→Gln; Asp 77→Lys; Trp 79→Ser; Arg 81→His; Tyr 100→Trp; Leu 103→Asp; Tyr 106→Leu; Lys 125→Gly; Ser 127→Met; Tyr 132→Val; Lys 134→Ala;

(d) Leu 36→Glu, Ala 40→Val; Ile 41→Glu; Gln 49→Val; Tyr 52→Thr; Ser 68→Glu; Leu 70→Arg; Arg 72→Trp; Lys 73→Leu; Asp77→Lys; Trp 79→Asn; Arg 81→His; Asn 96→Ala; Tyr 100→Gly; Leu 103→Met; Tyr 106→Thr; Lys 125→Thr; Ser 127→Met; Tyr 132→Trp; Lys 134→Trp;

(e) Leu 36→Gln; Ala 40→Tyr; Ile 41→Trp; Gln 49→Ile; Tyr 52→Ser; Ser 68→Ile; Leu 70→Tyr; Arg 72→Thr; Lys 73→Arg; Asp 77→Ser; Trp 79→Arg; Arg 81→Tyr; Asn 96→Pro; Leu 103→Asp; Tyr 106→Thr; Lys 125→His; Ser 127→Tyr; Tyr 132→Trp; Lys 134→Glu;

(f) Leu 36→Gln; Ala 40→Tyr; Gln 49→Glu; Tyr 52 Trp; Asn 65→Asp; Ser 68→Gly; Leu 70→Ser; Arg 72→Gly; Lys 73→Pro; Asp 77→Asn; Trp 79→Arg; Arg 81→Trp; Asn 96→Gly; Tyr 100→Ser; Leu 103→Gln; Tyr 106→Thr; Lys 125→His; Ser 127→Leu; Tyr 132→Phe; Lys 134→Glu;

(g) Leu 36→His; Ala 40→Tyr; Gln 49→Glu; Tyr 52 Trp; Asn 65→Asp; Ser 68→Glu; Leu 70→Ser; Arg 72→Gly; Lys 73→Pro; Asp 77→Asn; Trp 79→Arg;

Arg 81→Trp; Asn 96→Gly; Tyr 100→Pro; Leu 103→Asp; Tyr 106→Thr; Lys 125→His; Ser 127→Leu; Tyr 132→Phe; Lys 134→Glu;
(h) Leu 36→Gln; Ala 40→Tyr; Gln 49→Gly; Tyr 52 Trp; Asn 65→Asp; Ser 68→Glu; Leu 70→Ser; Arg 72→Gly; Lys 73→Ala; Asp 77→Asn; Trp 79→Arg; Arg 81→Trp; Asn 96→Gly; Tyr 100→Asp; Leu 103→Gly; Tyr 106→Thr; Lys 125→His; Ser 127→Leu; Tyr 132→Phe; Lys 134→Glu;
(i) Leu 36→His; Ala 40→Tyr; Gln 49→Gly; Tyr 52 Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;
(j) Leu 36→Gln; Ala 40→Tyr; Gln 49→Gly; Tyr 52 Trp; Asn 65→Asp; Ser 68→Gly; Leu 70→Ser; Arg 72→Gly; Lys 73→Ala; Asp 77→Val; Trp 79→Arg; Arg 81→Trp; Asn 96→Gly; Tyr 100→Pro; Leu 103→Gly; Tyr 106→Thr; Lys 125→His; Ser 127→Leu; Tyr 132→Phe; Lys 134→Glu;
(k) Leu 36→Gln; Ala 40→Tyr; Gln 49→Val; Tyr 52 Trp; Asn 65→Asp; Ser 68→Glu; Leu 70→Ser; Arg 72→Gly; Lys 73→Pro; Asp 77→Asn; Trp 79→Arg; Arg 81→Trp; Asn 96→Gly; Tyr 100→Leu; Leu 103→Gly; Tyr 106→Thr; Lys 125→His; Ser 127→Leu; Tyr 132→Phe; Lys 134→Glu;
(l) Leu 36→Val; Ala 40→Tyr; Ile 41→Tyr; Gln 49→Ile; Tyr 52 Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Tyr 100→Trp; Leu 103→Asp; Tyr 106→Pro; Asn 116→Asp; Lys 125→Gly; Ser 127→Met; Asn 129→Asp; Tyr 132→Val; Lys 134→Ala;
(m) Leu 36→Val; Ala 40→Tyr; Ile 41→Tyr; Gln 49→Ile; Tyr 52 Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Asn 96→Asp; Tyr 100→Trp; Leu 103→Asp; Tyr 106→Pro; Lys 125→Gly; Val 126→Met; Ser 127→Met; Asn 129→Asp; Tyr 132→Val; Lys 134→Ala; and
(n) Leu 36→Met; Ala 40→Tyr; Ile 41→Asp; Gln 49→Ile; Tyr 52→Thr; Asn 65→Asp; Ser 68→Gln; Leu 70→Gly; Arg 72→Glu; Lys 73→Gln; Asp 77→Lys; Trp 79→Ser; Arg 81→His; Asn 96→Gln; Tyr 100→Trp; Leu 103→Asp; Tyr 106→Pro; Lys 125→Gly; Ser 127→Met; Tyr 132→Val; Lys 134→Ala;

wherein each of the sets of mutated amino acid residues optionally further includes the mutations Gln 28→His and Cys 87→Ser.

8. The fusion protein of claim 1, wherein said mutein comprises an amino acid sequence selected from the group consisting of SEQ ID NOs: 2, 3, and 86-97 and functional fragments thereof.

9. The fusion protein of claim 1, wherein the amino acid sequence of said mutein has at least 85% sequence identity to an amino acid sequence selected from the group consisting of SEQ ID NOs: 2, 3, and 86-97.

10. The fusion protein of claim 1, wherein the immunoglobulin is monoclonal antibody.

11. The fusion protein of claim 10, wherein the monoclonal antibody has the heavy chain complementarity-determining regions (CDRs) contained in the heavy chain of SEQ ID NO: 8 and the light chain CDRs contained in the light chain of SEQ ID NO 9.

12. The fusion protein of claim 10, wherein the monoclonal antibody is bevacizumab.

13. The fusion protein of claim 10, wherein said fusion protein comprises the amino acid sequences of SEQ ID NOs: 9 and 10, or the amino acid sequences of SEQ ID NOs: 8 and 11, or the amino acid sequences of SEQ ID NOs: 9 and 12, or the amino acid sequences of SEQ ID NOs: 8 and 13, or the amino acid sequences of SEQ ID NOs: 9 and 14, or the amino acid sequences of SEQ ID NOs: 8 and 15, or the amino acid sequences of SEQ ID NOs: 9 and 16, or the amino acid sequences of SEQ ID NOs: 8 and 17.

14. The fusion protein of claim 1, wherein the amino acid sequence of said mutein has at least 95%, at least 97%, or at least 98% sequence identity to an amino acid sequence selected from the group consisting of SEQ ID NOs: 2, 3, and 86-97.

15. The fusion protein of claim 1, wherein the amino acid sequence of said fusion protein has at least 95% sequence identity to an amino acid sequence selected from SEQ ID NOs: 9 and 10, SEQ ID NOs: 8 and 11, SEQ ID NOs: 9 and 12, SEQ ID NOs: 8 and 13, SEQ ID NOs: 9 and 14, SEQ ID NOs: 8 and 15, SEQ ID NOs: 9 and 16, and SEQ ID NOs: 8 and 17.

16. A pharmaceutical composition comprising the fusion protein of claim 1.

17. A nucleic acid molecule comprising a nucleotide sequence encoding the fusion protein of claim 1.

18. A method of inhibiting or reducing angiogenesis in a subject, comprising administering to said subject an effective amount of a fusion protein of claim 1 or a composition comprising such fusion protein.

19. A method of treating or ameliorating a disease or disorder associated with deregulated angiogenesis in a subject, comprising administering to said subject an effective amount of the fusion protein of claim 1 or a composition comprising such fusion protein, wherein the disease or disorder is selected from the group consisting of: tumor growth, eye disorders, vascular diseases, inflammatory diseases, cancer, ocular neovascular diseases, arthritis, and psoriasis.

* * * * *

SEQUENCE LISTING

```
<160> NUMBER OF SEQ ID NOS: 97

<210> SEQ ID NO 1
<211> LENGTH: 178
<212> TYPE: PRT
<213> ORGANISM: Homo sapiens
<220> FEATURE:
<223> OTHER INFORMATION: hNGAL

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial Sequence
<220> FEATURE:
<223> OTHER INFORMATION: hNGAL mutein
```

<400> SEQUENCE: 2

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Gln Ala Gly Asn Tyr Ile Leu Arg Glu Asp Lys Asp Pro
         35                  40                  45

Gly Lys Met Trp Ala Thr Ile Tyr Glu Leu Lys Glu Asp Lys Ser Tyr
 50                  55                  60

Asp Val Thr Glu Val Ser Phe Gly Ala Lys Lys Cys Asn Tyr Arg Ile
 65                  70                  75                  80

Trp Thr Phe Val Pro Gly Ser Gln Pro Gly Glu Phe Thr Leu Gly Gly
                 85                  90                  95

Ile Lys Ser Asp Pro Gly Gly Thr Ser Thr Leu Val Arg Val Val Ser
                100                 105                 110

Thr Asn Tyr Asn Gln His Ala Met Val Phe Phe Lys His Val Leu Gln
             115                 120                 125

Asn Arg Glu Phe Phe Glu Ile Thr Leu Tyr Gly Arg Thr Lys Glu Leu
         130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 3
<211> LENGTH: 178
<212> TYPE: PRT
<213> ORGANISM: Artificial Sequence
<220> FEATURE:
<223> OTHER INFORMATION: hNGAL mutein

<400> SEQUENCE: 3

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly His Ala Gly Asn Tyr Ile Leu Arg Glu Asp Lys Asp Pro
         35                  40                  45

Gly Lys Met Trp Ala Thr Ile Tyr Glu Leu Lys Glu Asp Lys Ser Tyr
 50                  55                  60

Asp Val Thr Glu Val Ser Phe Gly Pro Lys Lys Cys Asn Tyr Arg Ile
 65                  70                  75                  80

Trp Thr Phe Val Pro Gly Ser Gln Pro Gly Glu Phe Thr Leu Gly Gly
                 85                  90                  95

Ile Lys Ser Pro Pro Gly Gly Thr Ser Thr Leu Val Arg Val Val Ser
                100                 105                 110

Thr Asn Tyr Asn Gln His Ala Met Val Phe Phe Lys His Val Leu Gln
             115                 120                 125

Asn Arg Glu Phe Phe Glu Ile Thr Leu Tyr Gly Arg Thr Lys Glu Leu
         130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

165                 170                 175

Asp Gly

<210> SEQ ID NO 4
<211> LENGTH: 459
<212> TYPE: PRT
<213> ORGANISM: Artificial Sequence
<220> FEATURE:
<223> OTHER INFORMATION: benchmark antibody 1 HC

<400> SEQUENCE: 4

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 5
<211> LENGTH: 214
<212> TYPE: PRT
<213> ORGANISM: Artificial Sequence
<220> FEATURE:
<223> OTHER INFORMATION: benchmark antibody 1 LC

<400> SEQUENCE: 5

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 6
<211> LENGTH: 452
<212> TYPE: PRT
<213> ORGANISM: Artificial Sequence
<220> FEATURE:
<223> OTHER INFORMATION: benchmark antibody 2 HC

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 7
<211> LENGTH: 214
<212> TYPE: PRT
<213> ORGANISM: Artificial Sequence
<220> FEATURE:
<223> OTHER INFORMATION: benchmark antibody 2 LC

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 453
<212> TYPE: PRT
<213> ORGANISM: Artificial Sequence
<220> FEATURE:
<223> OTHER INFORMATION: benchmark antibody 4 HC

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
```

```
            20                  25                  30
Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445
```

Leu Ser Pro Gly Lys
    450

<210> SEQ ID NO 9
<211> LENGTH: 214
<212> TYPE: PRT
<213> ORGANISM: Artificial Sequence
<220> FEATURE:
<223> OTHER INFORMATION: benchmark antibody 4 LC

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr

```
                65                  70                  75                  80
Leu Gln Met Asn Ser Leu Arg Ala Glu Asp Thr Ala Val Tyr Tyr Cys
                        85                  90                  95
Ala Lys Tyr Pro His Tyr Tyr Gly Ser Ser His Trp Tyr Phe Asp Val
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                    165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
                210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                    245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                    325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                    405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
                435                 440                 445
Leu Ser Pro Gly Lys Gly Gly Gly Ser Gly Gly Gly Gly Ser Gly
                450                 455                 460
Gly Gly Gly Ser Gln Asp Ser Thr Ser Asp Leu Ile Pro Ala Pro Pro
465                 470                 475                 480
Leu Ser Lys Val Pro Leu Gln Gln Asn Phe Gln Asp Asn Gln Phe His
                    485                 490                 495
```

Gly Lys Trp Tyr Val Gly His Ala Gly Asn Tyr Ile Leu Arg Glu
            500                 505                 510

Asp Lys Asp Pro Gly Lys Met Trp Ala Thr Ile Tyr Glu Leu Lys Glu
        515                 520                 525

Asp Lys Ser Tyr Asp Val Thr Glu Val Ser Phe Gly Pro Lys Lys Cys
    530                 535                 540

Asn Tyr Arg Ile Trp Thr Phe Val Pro Gly Ser Gln Pro Gly Glu Phe
545                 550                 555                 560

Thr Leu Gly Gly Ile Lys Ser Pro Pro Gly Gly Thr Ser Thr Leu Val
                565                 570                 575

Arg Val Val Ser Thr Asn Tyr Asn Gln His Ala Met Val Phe Phe Lys
            580                 585                 590

His Val Leu Gln Asn Arg Glu Phe Phe Glu Ile Thr Leu Tyr Gly Arg
        595                 600                 605

Thr Lys Glu Leu Thr Ser Glu Leu Lys Glu Asn Phe Ile Arg Phe Ser
    610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 11
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly His Ala Gly Asn Tyr Ile Leu Arg
            260                 265                 270

Glu Asp Lys Asp Pro Gly Lys Met Trp Ala Thr Ile Tyr Glu Leu Lys
        275                 280                 285

Glu Asp Lys Ser Tyr Asp Val Thr Glu Val Ser Phe Gly Pro Lys Lys
    290                 295                 300

Cys Asn Tyr Arg Ile Trp Thr Phe Val Pro Gly Ser Gln Pro Gly Glu
305                 310                 315                 320

Phe Thr Leu Gly Gly Ile Lys Ser Pro Pro Gly Gly Thr Ser Thr Leu
                325                 330                 335

Val Arg Val Val Ser Thr Asn Tyr Asn Gln His Ala Met Val Phe Phe
            340                 345                 350

Lys His Val Leu Gln Asn Arg Glu Phe Phe Glu Ile Thr Leu Tyr Gly
        355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405
```

```
<210> SEQ ID NO 12
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly His Ala Gly Asn Tyr Ile Leu Arg Glu Asp Lys Asp Pro
            35                  40                  45

Gly Lys Met Trp Ala Thr Ile Tyr Glu Leu Lys Glu Asp Lys Ser Tyr
        50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

-continued

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
        180                 185                 190

Ser Glu Val Gln Leu Val Glu Ser Gly Gly Leu Val Gln Pro Gly
    195                 200                 205

Gly Ser Leu Arg Leu Ser Cys Ala Ala Ser Gly Tyr Thr Phe Thr Asn
    210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
                260                 265                 270

Tyr Leu Gln Met Asn Ser Leu Arg Ala Glu Asp Thr Ala Val Tyr Tyr
                275                 280                 285

Cys Ala Lys Tyr Pro His Tyr Tyr Gly Ser Ser His Trp Tyr Phe Asp
                290                 295                 300

Val Trp Gly Gln Gly Thr Leu Val Thr Val Ser Ser Ala Ser Thr Lys
305                 310                 315                 320

Gly Pro Ser Val Phe Pro Leu Ala Pro Ser Ser Lys Ser Thr Ser Gly
                325                 330                 335

Gly Thr Ala Ala Leu Gly Cys Leu Val Lys Asp Tyr Phe Pro Glu Pro
                340                 345                 350

Val Thr Val Ser Trp Asn Ser Gly Ala Leu Thr Ser Gly Val His Thr
                355                 360                 365

Phe Pro Ala Val Leu Gln Ser Ser Gly Leu Tyr Ser Leu Ser Ser Val
                370                 375                 380

Val Thr Val Pro Ser Ser Ser Leu Gly Thr Gln Thr Tyr Ile Cys Asn
385                 390                 395                 400

Val Asn His Lys Pro Ser Asn Thr Lys Val Asp Lys Lys Val Glu Pro
                405                 410                 415

Lys Ser Cys Asp Lys Thr His Thr Cys Pro Pro Cys Pro Ala Pro Glu
                420                 425                 430

Leu Leu Gly Gly Pro Ser Val Phe Leu Phe Pro Pro Lys Pro Lys Asp
                435                 440                 445

Thr Leu Met Ile Ser Arg Thr Pro Glu Val Thr Cys Val Val Val Asp
450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
                500                 505                 510

Leu Asn Gly Lys Glu Tyr Lys Cys Lys Val Ser Asn Lys Ala Leu Pro
                515                 520                 525

Ala Pro Ile Glu Lys Thr Ile Ser Lys Ala Lys Gly Gln Pro Arg Glu
                530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                565                 570                 575

```
Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
        595                 600                 605

Leu Thr Val Asp Lys Ser Arg Trp Gln Gln Gly Asn Val Phe Ser Cys
        610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 13
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Tyr Ile Leu Arg Glu Asp Lys Asp Pro
        35                  40                  45

Gly Lys Met Trp Ala Thr Ile Tyr Glu Leu Lys Glu Asp Lys Ser Tyr
    50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gly Gly Gly Gly
            180                 185                 190

Ser Asp Ile Gln Met Thr Gln Ser Pro Ser Ser Leu Ser Ala Ser Val
        195                 200                 205

Gly Asp Arg Val Thr Ile Thr Cys Ser Ala Ser Gln Asp Ile Ser Asn
    210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285
```

```
Trp Thr Phe Gly Gln Gly Thr Lys Val Glu Ile Lys Arg Thr Val Ala
            290                 295                 300
Ala Pro Ser Val Phe Ile Phe Pro Pro Ser Asp Glu Gln Leu Lys Ser
305                 310                 315                 320
Gly Thr Ala Ser Val Val Cys Leu Leu Asn Asn Phe Tyr Pro Arg Glu
                325                 330                 335
Ala Lys Val Gln Trp Lys Val Asp Asn Ala Leu Gln Ser Gly Asn Ser
            340                 345                 350
Gln Glu Ser Val Thr Glu Gln Asp Ser Lys Asp Ser Thr Tyr Ser Leu
            355                 360                 365
Ser Ser Thr Leu Thr Leu Ser Lys Ala Asp Tyr Glu Lys His Lys Val
370                 375                 380
Tyr Ala Cys Glu Val Thr His Gln Gly Leu Ser Ser Pro Val Thr Lys
385                 390                 395                 400
Ser Phe Asn Arg Gly Glu Cys
                405

<210> SEQ ID NO 14
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 14

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
```

-continued

```
Leu Gly Gly Pro Ser Val Phe Leu Phe Pro Lys Pro Lys Asp Thr
                245                 250                 255
Leu Met Ile Ser Arg Thr Pro Glu Val Thr Cys Val Val Asp Val
        260                 265                 270
Ser His Glu Asp Pro Glu Val Lys Phe Asn Trp Tyr Val Asp Gly
    275                 280                 285
Glu Val His Asn Ala Lys Thr Lys Pro Arg Glu Gln Tyr Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys Gly Gly Gly Ser Gly Gly Gly Ser Gly
    450                 455                 460
Gly Gly Ser Gln Asp Ser Thr Ser Asp Leu Ile Pro Ala Pro Pro
465                 470                 475                 480
Leu Ser Lys Val Pro Leu Gln Gln Asn Phe Gln Asp Asn Gln Phe His
                485                 490                 495
Gly Lys Trp Tyr Val Val Gly Gln Ala Gly Asn Tyr Ile Leu Arg Glu
            500                 505                 510
Asp Lys Asp Pro Gly Lys Met Trp Ala Thr Ile Tyr Glu Leu Lys Glu
        515                 520                 525
Asp Lys Ser Tyr Asp Val Thr Glu Val Ser Phe Gly Ala Lys Lys Cys
    530                 535                 540
Asn Tyr Arg Ile Trp Thr Phe Val Pro Gly Ser Gln Pro Gly Glu Phe
545                 550                 555                 560
Thr Leu Gly Gly Ile Lys Ser Asp Pro Gly Gly Thr Ser Thr Leu Val
                565                 570                 575
Arg Val Val Ser Thr Asn Tyr Asn Gln His Ala Met Val Phe Phe Lys
            580                 585                 590
His Val Leu Gln Asn Arg Glu Phe Phe Glu Ile Thr Leu Tyr Gly Arg
        595                 600                 605
Thr Lys Glu Leu Thr Ser Glu Leu Lys Glu Asn Phe Ile Arg Phe Ser
    610                 615                 620
Lys Ser Leu Gly Leu Pro Glu Asn His Ile Val Phe Pro Val Pro Ile
625                 630                 635                 640
Asp Gln Cys Ile Asp Gly
                645
```

-continued

```
<210> SEQ ID NO 15
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
        210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Gln Ala Gly Asn Tyr Ile Leu Arg
            260                 265                 270

Glu Asp Lys Asp Pro Gly Lys Met Trp Ala Thr Ile Tyr Glu Leu Lys
        275                 280                 285

Glu Asp Lys Ser Tyr Asp Val Thr Glu Val Ser Phe Gly Ala Lys Lys
    290                 295                 300

Cys Asn Tyr Arg Ile Trp Thr Phe Val Pro Gly Ser Gln Pro Gly Glu
305                 310                 315                 320

Phe Thr Leu Gly Gly Ile Lys Ser Asp Pro Gly Gly Thr Ser Thr Leu
                325                 330                 335

Val Arg Val Val Ser Thr Asn Tyr Asn Gln His Ala Met Val Phe Phe
            340                 345                 350

Lys His Val Leu Gln Asn Arg Glu Phe Phe Glu Ile Thr Leu Tyr Gly
        355                 360                 365

Arg Thr Lys Glu Leu Thr Ser Glu Leu Lys Glu Asn Phe Ile Arg Phe
```

```
                    370                 375                 380
Ser Lys Ser Leu Gly Leu Pro Glu Asn His Ile Val Phe Pro Val Pro
385                 390                 395                 400

Ile Asp Gln Cys Ile Asp Gly
                405
```

<210> SEQ ID NO 16
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 16

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Tyr Ile Leu Arg Glu Asp Lys Asp Pro
            35                  40                  45

Gly Lys Met Trp Ala Thr Ile Tyr Glu Leu Lys Glu Asp Lys Ser Tyr
        50                  55                  60

Asp Val Thr Glu Val Ser Phe Gly Ala Lys Lys Cys Asn Tyr Arg Ile
65              70                  75                  80

Trp Thr Phe Val Pro Gly Ser Gln Pro Gly Glu Phe Thr Leu Gly Gly
                85                  90                  95

Ile Lys Ser Asp Pro Gly Thr Ser Thr Leu Val Arg Val Val Ser
                100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145             150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gly Gly Gly Gly
                180                 185                 190

Ser Glu Val Gln Leu Val Glu Ser Gly Gly Gly Leu Val Gln Pro Gly
            195                 200                 205

Gly Ser Leu Arg Leu Ser Cys Ala Ala Ser Gly Tyr Thr Phe Thr Asn
        210                 215                 220

Tyr Gly Met Asn Trp Val Arg Gln Ala Pro Gly Lys Gly Leu Glu Trp
225             230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
            260                 265                 270

Tyr Leu Gln Met Asn Ser Leu Arg Ala Glu Asp Thr Ala Val Tyr Tyr
        275                 280                 285

Cys Ala Lys Tyr Pro His Tyr Tyr Gly Ser Ser His Trp Tyr Phe Asp
        290                 295                 300

Val Trp Gly Gln Gly Thr Leu Val Thr Val Ser Ser Ala Ser Thr Lys
305             310                 315                 320

Gly Pro Ser Val Phe Pro Leu Ala Pro Ser Ser Lys Ser Thr Ser Gly
```

```
            325                 330                 335
Gly Thr Ala Ala Leu Gly Cys Leu Val Lys Asp Tyr Phe Pro Glu Pro
            340                 345                 350

Val Thr Val Ser Trp Asn Ser Gly Ala Leu Thr Ser Gly Val His Thr
            355                 360                 365

Phe Pro Ala Val Leu Gln Ser Ser Gly Leu Tyr Ser Leu Ser Ser Val
            370                 375                 380

Val Thr Val Pro Ser Ser Leu Gly Thr Gln Thr Tyr Ile Cys Asn
385                 390                 395                 400

Val Asn His Lys Pro Ser Asn Thr Lys Val Asp Lys Val Glu Pro
            405                 410                 415

Lys Ser Cys Asp Lys Thr His Thr Cys Pro Pro Cys Pro Ala Pro Glu
            420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
            450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
            485                 490                 495

Ser Thr Tyr Arg Val Val Ser Val Leu Thr Val Leu His Gln Asp Trp
            500                 505                 510

Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
            530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
            565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
            595                 600                 605

Leu Thr Val Asp Lys Ser Arg Trp Gln Gln Gly Asn Val Phe Ser Cys
            610                 615                 620

Ser Val Met His Glu Ala Leu His Asn His Tyr Thr Gln Lys Ser Leu
625                 630                 635                 640

Ser Leu Ser Pro Gly Lys
            645

<210> SEQ ID NO 17
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
```

```
                35                  40                  45
Gly Lys Met Trp Ala Thr Ile Tyr Glu Leu Lys Glu Asp Lys Ser Tyr
 50                  55                  60

Asp Val Thr Glu Val Ser Phe Gly Ala Lys Lys Cys Asn Tyr Arg Ile
 65                  70                  75                  80

Trp Thr Phe Val Pro Gly Ser Gln Pro Gly Glu Phe Thr Leu Gly Gly
                 85                  90                  95

Ile Lys Ser Asp Pro Gly Gly Thr Ser Thr Leu Val Arg Val Val Ser
                100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Asp Ile Gln Met Thr Gln Ser Pro Ser Ser Leu Ser Ala Ser Val
            195                 200                 205

Gly Asp Arg Val Thr Ile Thr Cys Ser Ala Ser Gln Asp Ile Ser Asn
210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
            275                 280                 285

Trp Thr Phe Gly Gln Gly Thr Lys Val Glu Ile Lys Arg Thr Val Ala
290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
            355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 18
<211> LENGTH: 154
<212> TYPE: PRT
<213> ORGANISM: Homo sapiens
<220> FEATURE:
<223> OTHER INFORMATION: Tlc
```

```
<400> SEQUENCE: 18

Ala Ser Asp Glu Glu Ile Gln Asp Val Ser Gly Thr Trp Tyr Leu Lys
1               5                   10                  15

Ala Met Thr Val Asp Arg Glu Phe Pro Glu Met Asn Leu Glu Ser Val
                20                  25                  30

Thr Pro Met Thr Leu Thr Thr Leu Glu Gly Gly Asn Leu Glu Ala Lys
            35                  40                  45

Val Thr Met Leu Ile Ser Gly Arg Cys Gln Glu Val Lys Ala Val Leu
50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Cys Glu Gly Glu Leu His Gly Lys Pro Val Arg Gly Val Lys Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Cys Ser Pro Gly Ser Asp
145                 150

<210> SEQ ID NO 19
<211> LENGTH: 15
<212> TYPE: PRT
<213> ORGANISM: Artificial Sequence
<220> FEATURE:
<223> OTHER INFORMATION: Linker (G4S)3

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 453
<212> TYPE: PRT
<213> ORGANISM: Artificial Sequence
<220> FEATURE:
<223> OTHER INFORMATION: benchmark antibody 3 HC-A

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125
```

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450

<210> SEQ ID NO 21
<211> LENGTH: 214
<212> TYPE: PRT
<213> ORGANISM: Artificial Sequence
<220> FEATURE:
<223> OTHER INFORMATION: benchmark antibody 3 LC-A

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

-continued

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
             85                  90                  95

Thr Phe Gly Gln Gly Thr Lys Val Glu Ile Lys Arg Thr Val Ala Ala
         100                 105                 110

Pro Ser Val Phe Ile Phe Pro Pro Ser Asp Glu Gln Leu Lys Ser Gly
     115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr
         180                 185                 190

Ala Cys Glu Val Thr His Gln Gly Leu Ser Ser Pro Val Thr Lys Ser
     195                 200                 205

Phe Asn Arg Gly Glu Cys
     210

<210> SEQ ID NO 22
<211> LENGTH: 463
<212> TYPE: PRT
<213> ORGANISM: Artificial Sequence
<220> FEATURE:
<223> OTHER INFORMATION: benchmark antibody 3 HC-B

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Ser Pro Asn Pro Tyr Tyr Tyr Asp Ser Ser Gly Tyr Tyr Tyr
         100                 105                 110

Pro Gly Ala Phe Asp Ile Trp Gly Gln Gly Thr Met Val Thr Val Ser
     115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
             165                 170                 175

```
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460

<210> SEQ ID NO 23
<211> LENGTH: 213
<212> TYPE: PRT
<213> ORGANISM: Artificial Sequence
<220> FEATURE:
<223> OTHER INFORMATION: benchmark antibody 3 LC-B

<400> SEQUENCE: 23

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80
```

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 24
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

-continued

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys Gly Gly Gly Ser Gly Gly Gly Ser Gly
450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
            485                 490                 495

Gly Lys Trp Tyr Val Val Gly Gln Ala Gly Asn Tyr Ile Leu Arg Glu
        500                 505                 510

Asp Lys Asp Pro Gly Lys Met Trp Ala Thr Ile Tyr Glu Leu Lys Glu
    515                 520                 525

Asp Lys Ser Tyr Asn Val Thr Gly Val Ser Phe Gly Pro Lys Lys Cys
530                 535                 540

Asn Tyr Thr Ile Trp Thr Phe Val Pro Gly Ser Gln Pro Gly Glu Phe
545                 550                 555                 560

Thr Leu Gly Gly Ile Lys Ser Pro Pro Gly Gly Thr Ser Thr Leu Val
            565                 570                 575

Arg Val Val Ser Thr Asn Tyr Asn Gln His Ala Met Val Phe Phe Lys
        580                 585                 590

His Val Leu Gln Asn Arg Glu Phe Phe Glu Ile Thr Leu Tyr Gly Arg
    595                 600                 605

Thr Lys Glu Leu Thr Ser Glu Leu Lys Glu Asn Phe Ile Arg Phe Ser
610                 615                 620

Lys Ser Leu Gly Leu Pro Glu Asn His Ile Val Phe Pro Val Pro Ile
625                 630                 635                 640

Asp Gln Cys Ile Asp Gly

<210> SEQ ID NO 25
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Gln Ala Gly Asn Tyr Ile Leu Arg
            260                 265                 270

Glu Asp Lys Asp Pro Gly Lys Met Trp Ala Thr Ile Tyr Glu Leu Lys
        275                 280                 285

Glu Asp Lys Ser Tyr Asn Val Thr Gly Val Ser Phe Gly Pro Lys Lys
    290                 295                 300

Cys Asn Tyr Thr Ile Trp Thr Phe Val Pro Gly Ser Gln Pro Gly Glu
305                 310                 315                 320

Phe Thr Leu Gly Gly Ile Lys Ser Pro Pro Gly Gly Thr Ser Thr Leu
                325                 330                 335

Val Arg Val Val Ser Thr Asn Tyr Asn Gln His Ala Met Val Phe Phe
            340                 345                 350

Lys His Val Leu Gln Asn Arg Glu Phe Phe Glu Ile Thr Leu Tyr Gly
```

```
              355                 360                 365
Arg Thr Lys Glu Leu Thr Ser Glu Leu Lys Glu Asn Phe Ile Arg Phe
370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 26
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Tyr Ile Leu Arg Glu Asp Lys Asp Pro
            35                  40                  45

Gly Lys Met Trp Ala Thr Ile Tyr Glu Leu Lys Glu Asp Lys Ser Tyr
    50                  55                  60

Asn Val Thr Gly Val Ser Phe Gly Pro Lys Lys Cys Asn Tyr Thr Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
    115                 120                 125

Asn Arg Glu Phe Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Glu Val Gln Leu Val Glu Ser Gly Gly Gly Leu Val Gln Pro Gly
    195                 200                 205

Gly Ser Leu Arg Leu Ser Cys Ala Ala Ser Gly Tyr Thr Phe Thr Asn
210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
            260                 265                 270

Tyr Leu Gln Met Asn Ser Leu Arg Ala Glu Asp Thr Ala Val Tyr Tyr
    275                 280                 285

Cys Ala Lys Tyr Pro His Tyr Tyr Gly Ser Ser His Trp Tyr Phe Asp
290                 295                 300

Val Trp Gly Gln Gly Thr Leu Val Thr Val Ser Ser Ala Ser Thr Lys
```

```
            305                 310                 315                 320
Gly Pro Ser Val Phe Pro Leu Ala Pro Ser Ser Lys Ser Thr Ser Gly
                325                 330                 335

Gly Thr Ala Ala Leu Gly Cys Leu Val Lys Asp Tyr Phe Pro Glu Pro
                340                 345                 350

Val Thr Val Ser Trp Asn Ser Gly Ala Leu Thr Ser Gly Val His Thr
                355                 360                 365

Phe Pro Ala Val Leu Gln Ser Ser Gly Leu Tyr Ser Leu Ser Ser Val
                370                 375                 380

Val Thr Val Pro Ser Ser Leu Gly Thr Gln Thr Tyr Ile Cys Asn
385                 390                 395                 400

Val Asn His Lys Pro Ser Asn Thr Lys Val Asp Lys Val Glu Pro
                405                 410                 415

Lys Ser Cys Asp Lys Thr His Thr Cys Pro Pro Cys Pro Ala Pro Glu
                420                 425                 430

Leu Leu Gly Gly Pro Ser Val Phe Leu Phe Pro Pro Lys Pro Lys Asp
                435                 440                 445

Thr Leu Met Ile Ser Arg Thr Pro Glu Val Thr Cys Val Val Val Asp
                450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
                500                 505                 510

Leu Asn Gly Lys Glu Tyr Lys Cys Lys Val Ser Asn Lys Ala Leu Pro
                515                 520                 525

Ala Pro Ile Glu Lys Thr Ile Ser Lys Ala Lys Gly Gln Pro Arg Glu
                530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
                580                 585                 590

Thr Pro Pro Val Leu Asp Ser Asp Gly Ser Phe Phe Leu Tyr Ser Lys
                595                 600                 605

Leu Thr Val Asp Lys Ser Arg Trp Gln Gln Gly Asn Val Phe Ser Cys
                610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 27
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
```

-continued

```
            20                  25                  30
Val Val Gly Gln Ala Gly Asn Tyr Ile Leu Arg Glu Asp Lys Asp Pro
            35                  40                  45
Gly Lys Met Trp Ala Thr Ile Tyr Glu Leu Lys Glu Asp Lys Ser Tyr
 50                  55                  60
Asn Val Thr Gly Val Ser Phe Gly Pro Lys Lys Cys Asn Tyr Thr Ile
 65                  70                  75                  80
Trp Thr Phe Val Pro Gly Ser Gln Pro Gly Glu Phe Thr Leu Gly Gly
                    85                  90                  95
Ile Lys Ser Pro Pro Gly Gly Thr Ser Thr Leu Val Arg Val Val Ser
                100                 105                 110
Thr Asn Tyr Asn Gln His Ala Met Val Phe Phe Lys His Val Leu Gln
                115                 120                 125
Asn Arg Glu Phe Phe Glu Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Ser Gly Gly Gly Gly
                180                 185                 190
Ser Asp Ile Gln Met Thr Gln Ser Pro Ser Ser Leu Ser Ala Ser Val
            195                 200                 205
Gly Asp Arg Val Thr Ile Thr Cys Ser Ala Ser Gln Asp Ile Ser Asn
            210                 215                 220
Tyr Leu Asn Trp Tyr Gln Gln Lys Pro Gly Lys Ala Pro Lys Val Leu
225                 230                 235                 240
Ile Tyr Phe Thr Ser Ser Leu His Ser Gly Val Pro Ser Arg Phe Ser
                245                 250                 255
Gly Ser Gly Ser Gly Thr Asp Phe Thr Leu Thr Ile Ser Ser Leu Gln
                260                 265                 270
Pro Glu Asp Phe Ala Thr Tyr Tyr Cys Gln Gln Tyr Ser Thr Val Pro
            275                 280                 285
Trp Thr Phe Gly Gln Gly Thr Lys Val Glu Ile Lys Arg Thr Val Ala
            290                 295                 300
Ala Pro Ser Val Phe Ile Phe Pro Pro Ser Asp Glu Gln Leu Lys Ser
305                 310                 315                 320
Gly Thr Ala Ser Val Val Cys Leu Leu Asn Asn Phe Tyr Pro Arg Glu
                325                 330                 335
Ala Lys Val Gln Trp Lys Val Asp Asn Ala Leu Gln Ser Gly Asn Ser
            340                 345                 350
Gln Glu Ser Val Thr Glu Gln Asp Ser Lys Asp Ser Thr Tyr Ser Leu
            355                 360                 365
Ser Ser Thr Leu Thr Leu Ser Lys Ala Asp Tyr Glu Lys His Lys Val
370                 375                 380
Tyr Ala Cys Glu Val Thr His Gln Gly Leu Ser Ser Pro Val Thr Lys
385                 390                 395                 400
Ser Phe Asn Arg Gly Glu Cys
                405

<210> SEQ ID NO 28
<211> LENGTH: 646
<212> TYPE: PRT
<213> ORGANISM: Artificial Sequence
```

<220> FEATURE:
<223> OTHER INFORMATION: hNGAL fusion protein

<400> SEQUENCE: 28

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |

Ser Leu Arg Leu Ser Cys Ala Ala Ser Gly Tyr Thr Phe Thr Asn Tyr
              20                  25                  30

Gly Met Asn Trp Val Arg Gln Ala Pro Gly Lys Gly Leu Glu Trp Val
          35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
              100                 105                 110

Trp Gly Gln Gly Thr Leu Val Thr Val Ser Ser Ala Ser Thr Lys Gly
          115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
              180                 185                 190

Thr Val Pro Ser Ser Ser Leu Gly Thr Gln Thr Tyr Ile Cys Asn Val
          195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
              260                 265                 270

Ser His Glu Asp Pro Glu Val Lys Phe Asn Trp Tyr Val Asp Gly Val
          275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
              340                 345                 350

Gln Val Tyr Thr Leu Pro Pro Ser Arg Glu Glu Met Thr Lys Asn Gln
          355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Gly Gly Ser Gly Gly Gly Ser Gly
            450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
            485                 490                 495

Gly Lys Trp Tyr Val Val Gly Phe Ala Gly Asn His Arg Leu Arg Glu
            500                 505                 510

Asp Lys Asp Pro Gly Lys Met His Ala Thr Ile Tyr Glu Leu Lys Glu
            515                 520                 525

Asp Lys Ser Tyr Asn Val Thr Asp Val Thr Phe Ala Phe Lys Lys Cys
            530                 535                 540

Asn Tyr Arg Ile His Thr Phe Val Pro Gly Ser Gln Pro Gly Glu Phe
545                 550                 555                 560

Thr Leu Gly Asn Ile Lys Ser Trp Pro Gly Glu Thr Ser Thr Leu Val
            565                 570                 575

Arg Val Val Ser Thr Asn Tyr Asn Gln His Ala Met Val Phe Phe Lys
            580                 585                 590

Thr Val Met Gln Asn Arg Glu Trp Phe Trp Ile Thr Leu Tyr Gly Arg
            595                 600                 605

Thr Lys Glu Leu Thr Ser Glu Leu Lys Glu Asn Phe Ile Arg Phe Ser
            610                 615                 620

Lys Ser Leu Gly Leu Pro Glu Asn His Ile Val Phe Pro Val Pro Ile
625                 630                 635                 640

Asp Gln Cys Ile Asp Gly
            645

<210> SEQ ID NO 29
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Phe Ala Gly Asn His Arg Leu Arg
            260                 265                 270

Glu Asp Lys Asp Pro Gly Lys Met His Ala Thr Ile Tyr Glu Leu Lys
        275                 280                 285

Glu Asp Lys Ser Tyr Asn Val Thr Asp Val Thr Phe Ala Phe Lys Lys
    290                 295                 300

Cys Asn Tyr Arg Ile His Thr Phe Val Pro Gly Ser Gln Pro Gly Glu
305                 310                 315                 320

Phe Thr Leu Gly Asn Ile Lys Ser Trp Pro Gly Glu Thr Ser Thr Leu
                325                 330                 335

Val Arg Val Val Ser Thr Asn Tyr Asn Gln His Ala Met Val Phe Phe
            340                 345                 350

Lys Thr Val Met Gln Asn Arg Glu Trp Phe Trp Ile Thr Leu Tyr Gly
        355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 30
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 30

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn His Arg Leu Arg Glu Asp Lys Asp Pro
        35                  40                  45

Gly Lys Met His Ala Thr Ile Tyr Glu Leu Lys Glu Asp Lys Ser Tyr
    50                  55                  60

```
Asn Val Thr Asp Val Thr Phe Ala Phe Lys Lys Cys Asn Tyr Arg Ile
 65              70                  75                  80

His Thr Phe Val Pro Gly Ser Gln Pro Gly Glu Phe Thr Leu Gly Asn
                 85                  90                  95

Ile Lys Ser Trp Pro Gly Glu Thr Ser Thr Leu Val Arg Val Val Ser
                100                 105                 110

Thr Asn Tyr Asn Gln His Ala Met Val Phe Phe Lys Thr Val Met Gln
            115                 120                 125

Asn Arg Glu Trp Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gly Ser Gly Gly Gly Gly Ser Gly Gly Gly Gly
                180                 185                 190

Ser Glu Val Gln Leu Val Glu Ser Gly Gly Gly Leu Val Gln Pro Gly
        195                 200                 205

Gly Ser Leu Arg Leu Ser Cys Ala Ala Ser Gly Tyr Thr Phe Thr Asn
210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
                260                 265                 270

Tyr Leu Gln Met Asn Ser Leu Arg Ala Glu Asp Thr Ala Val Tyr Tyr
            275                 280                 285

Cys Ala Lys Tyr Pro His Tyr Tyr Gly Ser Ser His Trp Tyr Phe Asp
        290                 295                 300

Val Trp Gly Gln Gly Thr Leu Val Thr Val Ser Ser Ala Ser Thr Lys
305                 310                 315                 320

Gly Pro Ser Val Phe Pro Leu Ala Pro Ser Ser Lys Ser Thr Ser Gly
                325                 330                 335

Gly Thr Ala Ala Leu Gly Cys Leu Val Lys Asp Tyr Phe Pro Glu Pro
                340                 345                 350

Val Thr Val Ser Trp Asn Ser Gly Ala Leu Thr Ser Gly Val His Thr
            355                 360                 365

Phe Pro Ala Val Leu Gln Ser Ser Gly Leu Tyr Ser Leu Ser Ser Val
        370                 375                 380

Val Thr Val Pro Ser Ser Ser Leu Gly Thr Gln Thr Tyr Ile Cys Asn
385                 390                 395                 400

Val Asn His Lys Pro Ser Asn Thr Lys Val Asp Lys Lys Val Glu Pro
                405                 410                 415

Lys Ser Cys Asp Lys Thr His Thr Cys Pro Pro Cys Pro Ala Pro Glu
                420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
        450                 455                 460

Val Ser His Glu Asp Pro Glu Val Lys Phe Asn Trp Tyr Val Asp Gly
465                 470                 475                 480
```

```
Val Glu Val His Asn Ala Lys Thr Lys Pro Arg Glu Glu Gln Tyr Asn
            485                 490                 495

Ser Thr Tyr Arg Val Val Ser Val Leu Thr Val Leu His Gln Asp Trp
        500                 505                 510

Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
        530                 535                 540

Pro Gln Val Tyr Thr Leu Pro Pro Ser Arg Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
        595                 600                 605

Leu Thr Val Asp Lys Ser Arg Trp Gln Gln Gly Asn Val Phe Ser Cys
            610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 31
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 31

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn His Arg Leu Arg Glu Asp Lys Asp Pro
        35                  40                  45

Gly Lys Met His Ala Thr Ile Tyr Glu Leu Lys Glu Asp Lys Ser Tyr
    50                  55                  60

Asn Val Thr Asp Val Thr Phe Ala Phe Lys Lys Cys Asn Tyr Arg Ile
65                  70                  75                  80

His Thr Phe Val Pro Gly Ser Gln Pro Gly Glu Phe Thr Leu Gly Asn
                85                  90                  95

Ile Lys Ser Trp Pro Gly Glu Thr Ser Thr Leu Val Arg Val Val Ser
            100                 105                 110

Thr Asn Tyr Asn Gln His Ala Met Val Phe Phe Lys Thr Val Met Gln
        115                 120                 125

Asn Arg Glu Trp Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190
```

```
Ser Asp Ile Gln Met Thr Gln Ser Pro Ser Ser Leu Ser Ala Ser Val
            195                 200                 205

Gly Asp Arg Val Thr Ile Thr Cys Ser Ala Ser Gln Asp Ile Ser Asn
210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
            245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
            275                 280                 285

Trp Thr Phe Gly Gln Gly Thr Lys Val Glu Ile Lys Arg Thr Val Ala
            290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
            325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
            355                 360                 365

Ser Ser Thr Leu Thr Leu Ser Lys Ala Asp Tyr Glu Lys His Lys Val
            370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 32
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

-continued

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Ser Gly
    450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                485                 490                 495

Gly Lys Trp Tyr Val Val Gly Val Ala Gly Asn Trp Tyr Leu Arg Glu
            500                 505                 510

Asp Lys Asp Pro Ile Lys Met Thr Ala Thr Ile Tyr Glu Leu Lys Glu
        515                 520                 525

Asp Lys Ser Tyr Asn Val Thr Gln Val Gly Phe Glu Gln Lys Lys Cys
    530                 535                 540

Lys Tyr Ser Ile His Thr Phe Val Pro Gly Ser Gln Pro Gly Glu Phe
545                 550                 555                 560

Thr Leu Gly Asp Ile Lys Ser Trp Pro Gly Asp Thr Ser Leu Leu Val
```

```
                    565                 570                 575
Arg Val Val Ser Thr Asn Tyr Asn Gln His Ala Met Val Phe Phe Lys
            580                 585                 590

Gly Val Met Gln Asn Arg Glu Val Phe Ala Ile Thr Leu Tyr Gly Arg
            595                 600                 605

Thr Lys Glu Leu Thr Ser Glu Leu Lys Glu Asn Phe Ile Arg Phe Ser
            610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 33
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Val Ala Gly Asn Trp Tyr Leu Arg
            260                 265                 270

Glu Asp Lys Asp Pro Ile Lys Met Thr Ala Thr Ile Tyr Glu Leu Lys
```

```
            275                 280                 285
Glu Asp Lys Ser Tyr Asn Val Thr Gln Val Gly Phe Glu Gln Lys Lys
    290                 295                 300

Cys Lys Tyr Ser Ile His Thr Phe Val Pro Gly Ser Gln Pro Gly Glu
305                 310                 315                 320

Phe Thr Leu Gly Asp Ile Lys Ser Trp Pro Gly Asp Thr Ser Leu Leu
                325                 330                 335

Val Arg Val Val Ser Thr Asn Tyr Asn Gln His Ala Met Val Phe Phe
            340                 345                 350

Lys Gly Val Met Gln Asn Arg Glu Val Phe Ala Ile Thr Leu Tyr Gly
        355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405
```

<210> SEQ ID NO 34
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 34

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Trp Tyr Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asn Val Thr Gln Val Gly Phe Glu Gln Lys Lys Cys Lys Tyr Ser Ile
65                  70                  75                  80

His Thr Phe Val Pro Gly Ser Gln Pro Gly Glu Phe Thr Leu Gly Asp
                85                  90                  95

Ile Lys Ser Trp Pro Gly Asp Thr Ser Leu Leu Val Arg Val Val Ser
            100                 105                 110

Thr Asn Tyr Asn Gln His Ala Met Val Phe Phe Lys Gly Val Met Gln
        115                 120                 125

Asn Arg Glu Val Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gly Gly Gly Gly
            180                 185                 190

Ser Glu Val Gln Leu Val Glu Ser Gly Gly Gly Leu Val Gln Pro Gly
        195                 200                 205

Gly Ser Leu Arg Leu Ser Cys Ala Ala Ser Gly Tyr Thr Phe Thr Asn
    210                 215                 220

Tyr Gly Met Asn Trp Val Arg Gln Ala Pro Gly Lys Gly Leu Glu Trp
```

-continued

```
            225                 230                 235                 240
        Val Gly Trp Ile Asn Thr Tyr Thr Gly Glu Pro Thr Tyr Ala Ala Asp
                        245                 250                 255
        Phe Lys Arg Arg Phe Thr Phe Ser Leu Asp Thr Ser Lys Ser Thr Ala
                        260                 265                 270
        Tyr Leu Gln Met Asn Ser Leu Arg Ala Glu Asp Thr Ala Val Tyr Tyr
                        275                 280                 285
        Cys Ala Lys Tyr Pro His Tyr Tyr Gly Ser Ser His Trp Tyr Phe Asp
                        290                 295                 300
        Val Trp Gly Gln Gly Thr Leu Val Thr Val Ser Ser Ala Ser Thr Lys
        305                 310                 315                 320
        Gly Pro Ser Val Phe Pro Leu Ala Pro Ser Ser Lys Ser Thr Ser Gly
                        325                 330                 335
        Gly Thr Ala Ala Leu Gly Cys Leu Val Lys Asp Tyr Phe Pro Glu Pro
                        340                 345                 350
        Val Thr Val Ser Trp Asn Ser Gly Ala Leu Thr Ser Gly Val His Thr
                        355                 360                 365
        Phe Pro Ala Val Leu Gln Ser Ser Gly Leu Tyr Ser Leu Ser Ser Val
                        370                 375                 380
        Val Thr Val Pro Ser Ser Ser Leu Gly Thr Gln Thr Tyr Ile Cys Asn
        385                 390                 395                 400
        Val Asn His Lys Pro Ser Asn Thr Lys Val Asp Lys Lys Val Glu Pro
                        405                 410                 415
        Lys Ser Cys Asp Lys Thr His Thr Cys Pro Pro Cys Pro Ala Pro Glu
                        420                 425                 430
        Leu Leu Gly Gly Pro Ser Val Phe Leu Phe Pro Pro Lys Pro Lys Asp
                        435                 440                 445
        Thr Leu Met Ile Ser Arg Thr Pro Glu Val Thr Cys Val Val Val Asp
                        450                 455                 460
        Val Ser His Glu Asp Pro Glu Val Lys Phe Asn Trp Tyr Val Asp Gly
        465                 470                 475                 480
        Val Glu Val His Asn Ala Lys Thr Lys Pro Arg Glu Glu Gln Tyr Asn
                        485                 490                 495
        Ser Thr Tyr Arg Val Val Ser Val Leu Thr Val Leu His Gln Asp Trp
                        500                 505                 510
        Leu Asn Gly Lys Glu Tyr Lys Cys Lys Val Ser Asn Lys Ala Leu Pro
                        515                 520                 525
        Ala Pro Ile Glu Lys Thr Ile Ser Lys Ala Lys Gly Gln Pro Arg Glu
                        530                 535                 540
        Pro Gln Val Tyr Thr Leu Pro Pro Ser Arg Glu Glu Met Thr Lys Asn
        545                 550                 555                 560
        Gln Val Ser Leu Thr Cys Leu Val Lys Gly Phe Tyr Pro Ser Asp Ile
                        565                 570                 575
        Ala Val Glu Trp Glu Ser Asn Gly Gln Pro Glu Asn Asn Tyr Lys Thr
                        580                 585                 590
        Thr Pro Pro Val Leu Asp Ser Asp Gly Ser Phe Phe Leu Tyr Ser Lys
                        595                 600                 605
        Leu Thr Val Asp Lys Ser Arg Trp Gln Gln Gly Asn Val Phe Ser Cys
                        610                 615                 620
        Ser Val Met His Glu Ala Leu His Asn His Tyr Thr Gln Lys Ser Leu
        625                 630                 635                 640
        Ser Leu Ser Pro Gly Lys
                        645
```

<210> SEQ ID NO 35
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 35

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Trp Tyr Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asn Val Thr Gln Val Gly Phe Glu Gln Lys Lys Cys Lys Tyr Ser Ile
65                  70                  75                  80

His Thr Phe Val Pro Gly Ser Gln Pro Gly Glu Phe Thr Leu Gly Asp
                85                  90                  95

Ile Lys Ser Trp Pro Gly Asp Thr Ser Leu Leu Val Arg Val Val Ser
            100                 105                 110

Thr Asn Tyr Asn Gln His Ala Met Val Phe Phe Lys Gly Val Met Gln
        115                 120                 125

Asn Arg Glu Val Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gly Ser Gly Gly Gly Gly Ser Gly Gly Gly Gly
            180                 185                 190

Ser Asp Ile Gln Met Thr Gln Ser Pro Ser Ser Leu Ser Ala Ser Val
        195                 200                 205

Gly Asp Arg Val Thr Ile Thr Cys Ser Ala Ser Gln Asp Ile Ser Asn
    210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285

Trp Thr Phe Gly Gln Gly Thr Lys Val Glu Ile Lys Arg Thr Val Ala
    290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
        355                 360                 365
```

```
Ser Ser Thr Leu Thr Leu Ser Lys Ala Asp Tyr Glu Lys His Lys Val
    370             375             380
Tyr Ala Cys Glu Val Thr His Gln Gly Leu Ser Ser Pro Val Thr Lys
385             390             395             400
Ser Phe Asn Arg Gly Glu Cys
            405

<210> SEQ ID NO 36
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 36

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
```

```
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Ser Gly
    450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                485                 490                 495

Gly Lys Trp Tyr Val Val Gly Glu Ala Gly Asn Val Glu Leu Arg Glu
            500                 505                 510

Asp Lys Asp Pro Val Lys Met Thr Ala Thr Ile Tyr Glu Leu Lys Glu
        515                 520                 525

Asp Lys Ser Tyr Asn Val Thr Glu Val Arg Phe Trp Leu Lys Lys Cys
    530                 535                 540

Lys Tyr Asn Ile His Thr Phe Val Pro Gly Ser Gln Pro Gly Glu Phe
545                 550                 555                 560

Thr Leu Gly Ala Ile Lys Ser Gly Pro Gly Met Thr Ser Thr Leu Val
                565                 570                 575

Arg Val Val Ser Thr Asn Tyr Asn Gln His Ala Met Val Phe Phe Lys
            580                 585                 590

Thr Val Met Gln Asn Arg Glu Trp Phe Trp Ile Thr Leu Tyr Gly Arg
        595                 600                 605

Thr Lys Glu Leu Thr Ser Glu Leu Lys Glu Asn Phe Ile Arg Phe Ser
    610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 37
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 37

Asp Ile Gln Met Thr Gln Ser Pro Ser Leu Ser Ala Ser Val Gly
1               5                   10                  15

Asp Arg Val Thr Ile Thr Cys Ser Ala Ser Gln Asp Ile Ser Asn Tyr
            20                  25                  30
```

```
Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Glu Ala Gly Asn Val Glu Leu Arg
            260                 265                 270

Glu Asp Lys Asp Pro Val Lys Met Thr Ala Thr Ile Tyr Glu Leu Lys
        275                 280                 285

Glu Asp Lys Ser Tyr Asn Val Thr Glu Val Arg Phe Trp Leu Lys Lys
    290                 295                 300

Cys Lys Tyr Asn Ile His Thr Phe Val Pro Gly Ser Gln Pro Gly Glu
305                 310                 315                 320

Phe Thr Leu Gly Ala Ile Lys Ser Gly Pro Gly Met Thr Ser Thr Leu
                325                 330                 335

Val Arg Val Val Ser Thr Asn Tyr Asn Gln His Ala Met Val Phe Phe
            340                 345                 350

Lys Thr Val Met Gln Asn Arg Glu Trp Phe Trp Ile Thr Leu Tyr Gly
        355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 38
<211> LENGTH: 646
<212> TYPE: PRT
<213> ORGANISM: Artificial Sequence
<220> FEATURE:
```

<223> OTHER INFORMATION: hNGAL fusion protein

<400> SEQUENCE: 38

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Val Glu Leu Arg Glu Asp Lys Asp Pro
        35                  40                  45

Val Lys Met Thr Ala Thr Ile Tyr Glu Leu Lys Glu Asp Lys Ser Tyr
    50                  55                  60

Asn Val Thr Glu Val Arg Phe Trp Leu Lys Lys Cys Lys Tyr Asn Ile
65                  70                  75                  80

His Thr Phe Val Pro Gly Ser Gln Pro Gly Glu Phe Thr Leu Gly Ala
                85                  90                  95

Ile Lys Ser Gly Pro Gly Met Thr Ser Thr Leu Val Arg Val Val Ser
            100                 105                 110

Thr Asn Tyr Asn Gln His Ala Met Val Phe Phe Lys Thr Val Met Gln
        115                 120                 125

Asn Arg Glu Trp Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Glu Val Gln Leu Val Glu Ser Gly Gly Leu Val Gln Pro Gly
    195                 200                 205

Gly Ser Leu Arg Leu Ser Cys Ala Ala Ser Gly Tyr Thr Phe Thr Asn
    210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
            260                 265                 270

Tyr Leu Gln Met Asn Ser Leu Arg Ala Glu Asp Thr Ala Val Tyr Tyr
        275                 280                 285

Cys Ala Lys Tyr Pro His Tyr Tyr Gly Ser Ser His Trp Tyr Phe Asp
    290                 295                 300

Val Trp Gly Gln Gly Thr Leu Val Thr Val Ser Ser Ala Ser Thr Lys
305                 310                 315                 320

Gly Pro Ser Val Phe Pro Leu Ala Pro Ser Ser Lys Ser Thr Ser Gly
                325                 330                 335

Gly Thr Ala Ala Leu Gly Cys Leu Val Lys Asp Tyr Phe Pro Glu Pro
            340                 345                 350

Val Thr Val Ser Trp Asn Ser Gly Ala Leu Thr Ser Gly Val His Thr
        355                 360                 365

Phe Pro Ala Val Leu Gln Ser Ser Gly Leu Tyr Ser Leu Ser Ser Val
    370                 375                 380

Val Thr Val Pro Ser Ser Ser Leu Gly Thr Gln Thr Tyr Ile Cys Asn
385                 390                 395                 400
```

-continued

```
Val Asn His Lys Pro Ser Asn Thr Lys Val Asp Lys Lys Val Glu Pro
                405                 410                 415
Lys Ser Cys Asp Lys Thr His Thr Cys Pro Pro Cys Pro Ala Pro Glu
            420                 425                 430
Leu Leu Gly Gly Pro Ser Val Phe Leu Phe Pro Pro Lys Pro Lys Asp
        435                 440                 445
Thr Leu Met Ile Ser Arg Thr Pro Glu Val Thr Cys Val Val Val Asp
    450                 455                 460
Val Ser His Glu Asp Pro Glu Val Lys Phe Asn Trp Tyr Val Asp Gly
465                 470                 475                 480
Val Glu Val His Asn Ala Lys Thr Lys Pro Arg Glu Glu Gln Tyr Asn
                485                 490                 495
Ser Thr Tyr Arg Val Val Ser Val Leu Thr Val Leu His Gln Asp Trp
            500                 505                 510
Leu Asn Gly Lys Glu Tyr Lys Cys Lys Val Ser Asn Lys Ala Leu Pro
        515                 520                 525
Ala Pro Ile Glu Lys Thr Ile Ser Lys Ala Lys Gly Gln Pro Arg Glu
    530                 535                 540
Pro Gln Val Tyr Thr Leu Pro Pro Ser Arg Glu Glu Met Thr Lys Asn
545                 550                 555                 560
Gln Val Ser Leu Thr Cys Leu Val Lys Gly Phe Tyr Pro Ser Asp Ile
                565                 570                 575
Ala Val Glu Trp Glu Ser Asn Gly Gln Pro Glu Asn Asn Tyr Lys Thr
            580                 585                 590
Thr Pro Pro Val Leu Asp Ser Asp Gly Ser Phe Phe Leu Tyr Ser Lys
        595                 600                 605
Leu Thr Val Asp Lys Ser Arg Trp Gln Gln Gly Asn Val Phe Ser Cys
    610                 615                 620
Ser Val Met His Glu Ala Leu His Asn His Tyr Thr Gln Lys Ser Leu
625                 630                 635                 640
Ser Leu Ser Pro Gly Lys
                645

<210> SEQ ID NO 39
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 39

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly Glu Ala Gly Asn Val Glu Leu Arg Glu Asp Lys Asp Pro
            35                  40                  45
Val Lys Met Thr Ala Thr Ile Tyr Glu Leu Lys Glu Asp Lys Ser Tyr
        50                  55                  60
Asn Val Thr Glu Val Arg Phe Trp Leu Lys Lys Cys Lys Tyr Asn Ile
65                  70                  75                  80
His Thr Phe Val Pro Gly Ser Gln Pro Gly Glu Phe Thr Leu Gly Ala
                85                  90                  95
Ile Lys Ser Gly Pro Gly Met Thr Ser Thr Leu Val Arg Val Val Ser
            100                 105                 110
```

```
Thr Asn Tyr Asn Gln His Ala Met Val Phe Lys Thr Val Met Gln
            115                 120                 125

Asn Arg Glu Trp Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Asp Ile Gln Met Thr Gln Ser Pro Ser Ser Leu Ser Ala Ser Val
            195                 200                 205

Gly Asp Arg Val Thr Ile Thr Cys Ser Ala Ser Gln Asp Ile Ser Asn
210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
275                 280                 285

Trp Thr Phe Gly Gln Gly Thr Lys Val Glu Ile Lys Arg Thr Val Ala
290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 40
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60
```

-continued

```
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gly
    450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
```

```
                    485                 490                 495
Gly Lys Trp Tyr Val Gly Gln Ala Gly Asn Tyr Trp Leu Arg Glu
            500                 505                 510

Asp Lys Asp Pro Ile Lys Met Ser Ala Thr Ile Tyr Glu Leu Lys Glu
            515                 520                 525

Asp Lys Ser Tyr Asn Val Thr Ile Val Tyr Phe Thr Arg Lys Lys Cys
        530                 535                 540

Ser Tyr Arg Ile Tyr Thr Phe Val Pro Gly Ser Gln Pro Gly Glu Phe
545                 550                 555                 560

Thr Leu Gly Pro Ile Lys Ser Tyr Pro Gly Asp Thr Ser Thr Leu Val
                565                 570                 575

Arg Val Val Ser Thr Asn Tyr Asn Gln His Ala Met Val Phe Phe Lys
                580                 585                 590

His Val Tyr Gln Asn Arg Glu Trp Phe Glu Ile Thr Leu Tyr Gly Arg
            595                 600                 605

Thr Lys Glu Leu Thr Ser Glu Leu Lys Glu Asn Phe Ile Arg Phe Ser
        610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 41
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

```
                195                 200                 205
Phe Asn Arg Gly Glu Cys Gly Gly Gly Ser Gly Gly Gly Ser
210                 215                 220
Gly Gly Gly Gly Ser Gln Asp Ser Thr Ser Asp Leu Ile Pro Ala Pro
225                 230                 235                 240
Pro Leu Ser Lys Val Pro Leu Gln Gln Asn Phe Gln Asp Asn Gln Phe
            245                 250                 255
His Gly Lys Trp Tyr Val Val Gly Gln Ala Gly Asn Tyr Trp Leu Arg
            260                 265                 270
Glu Asp Lys Asp Pro Ile Lys Met Ser Ala Thr Ile Tyr Glu Leu Lys
            275                 280                 285
Glu Asp Lys Ser Tyr Asn Val Thr Ile Val Tyr Phe Thr Arg Lys Lys
            290                 295                 300
Cys Ser Tyr Arg Ile Tyr Thr Phe Val Pro Gly Ser Gln Pro Gly Glu
305                 310                 315                 320
Phe Thr Leu Gly Pro Ile Lys Ser Tyr Pro Gly Asp Thr Ser Thr Leu
                325                 330                 335
Val Arg Val Val Ser Thr Asn Tyr Asn Gln His Ala Met Val Phe Phe
            340                 345                 350
Lys His Val Tyr Gln Asn Arg Glu Trp Phe Glu Ile Thr Leu Tyr Gly
            355                 360                 365
Arg Thr Lys Glu Leu Thr Ser Glu Leu Lys Glu Asn Phe Ile Arg Phe
370                 375                 380
Ser Lys Ser Leu Gly Leu Pro Glu Asn His Ile Val Phe Pro Val Pro
385                 390                 395                 400
Ile Asp Gln Cys Ile Asp Gly
                405

<210> SEQ ID NO 42
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 42

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly Gln Ala Gly Asn Tyr Trp Leu Arg Glu Asp Lys Asp Pro
            35                  40                  45
Ile Lys Met Ser Ala Thr Ile Tyr Glu Leu Lys Glu Asp Lys Ser Tyr
50                  55                  60
Asn Val Thr Ile Val Tyr Phe Thr Arg Lys Lys Cys Ser Tyr Arg Ile
65                  70                  75                  80
Tyr Thr Phe Val Pro Gly Ser Gln Pro Gly Glu Phe Thr Leu Gly Pro
                85                  90                  95
Ile Lys Ser Tyr Pro Gly Asp Thr Ser Thr Leu Val Arg Val Val Ser
            100                 105                 110
Thr Asn Tyr Asn Gln His Ala Met Val Phe Phe Lys His Val Tyr Gln
            115                 120                 125
Asn Arg Glu Trp Phe Glu Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
```

```
                145                 150                 155                 160
Leu Pro Glu Asn His Ile Val Phe Pro Val Pro Ile Asp Gln Cys Ile
                    165                 170                 175

Asp Gly Gly Gly Gly Ser Gly Gly Gly Ser Gly Gly Gly Gly
                180                 185                 190

Ser Glu Val Gln Leu Val Glu Ser Gly Gly Gly Leu Val Gln Pro Gly
                    195                 200                 205

Gly Ser Leu Arg Leu Ser Cys Ala Ala Ser Gly Tyr Thr Phe Thr Asn
                210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                    245                 250                 255

Phe Lys Arg Arg Phe Thr Phe Ser Leu Asp Thr Ser Lys Ser Thr Ala
                260                 265                 270

Tyr Leu Gln Met Asn Ser Leu Arg Ala Glu Asp Thr Ala Val Tyr Tyr
                    275                 280                 285

Cys Ala Lys Tyr Pro His Tyr Tyr Gly Ser Ser His Trp Tyr Phe Asp
                290                 295                 300

Val Trp Gly Gln Gly Thr Leu Val Thr Val Ser Ser Ala Ser Thr Lys
305                 310                 315                 320

Gly Pro Ser Val Phe Pro Leu Ala Pro Ser Ser Lys Ser Thr Ser Gly
                    325                 330                 335

Gly Thr Ala Ala Leu Gly Cys Leu Val Lys Asp Tyr Phe Pro Glu Pro
                340                 345                 350

Val Thr Val Ser Trp Asn Ser Gly Ala Leu Thr Ser Gly Val His Thr
                    355                 360                 365

Phe Pro Ala Val Leu Gln Ser Ser Gly Leu Tyr Ser Leu Ser Ser Val
                370                 375                 380

Val Thr Val Pro Ser Ser Ser Leu Gly Thr Gln Thr Tyr Ile Cys Asn
385                 390                 395                 400

Val Asn His Lys Pro Ser Asn Thr Lys Val Asp Lys Lys Val Glu Pro
                    405                 410                 415

Lys Ser Cys Asp Lys Thr His Thr Cys Pro Pro Cys Pro Ala Pro Glu
                420                 425                 430

Leu Leu Gly Gly Pro Ser Val Phe Leu Phe Pro Lys Pro Lys Asp
                435                 440                 445

Thr Leu Met Ile Ser Arg Thr Pro Glu Val Thr Cys Val Val Val Asp
                    450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                    485                 490                 495

Ser Thr Tyr Arg Val Val Ser Val Leu Thr Val Leu His Gln Asp Trp
                500                 505                 510

Leu Asn Gly Lys Glu Tyr Lys Cys Lys Val Ser Asn Lys Ala Leu Pro
                515                 520                 525

Ala Pro Ile Glu Lys Thr Ile Ser Lys Ala Lys Gly Gln Pro Arg Glu
                    530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                    565                 570                 575
```

```
Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
        595                 600                 605

Leu Thr Val Asp Lys Ser Arg Trp Gln Gln Gly Asn Val Phe Ser Cys
    610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 43
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 43

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Trp Leu Arg Glu Asp Lys Asp Pro
        35                  40                  45

Ile Lys Met Ser Ala Thr Ile Tyr Glu Leu Lys Glu Asp Lys Ser Tyr
    50                  55                  60

Asn Val Thr Ile Val Tyr Phe Thr Arg Lys Lys Cys Ser Tyr Arg Ile
65                  70                  75                  80

Tyr Thr Phe Val Pro Gly Ser Gln Pro Gly Glu Phe Thr Leu Gly Pro
                85                  90                  95

Ile Lys Ser Tyr Pro Gly Asp Thr Ser Thr Leu Val Arg Val Val Ser
            100                 105                 110

Thr Asn Tyr Asn Gln His Ala Met Val Phe Phe Lys His Val Tyr Gln
        115                 120                 125

Asn Arg Glu Trp Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gly Gly Gly Gly
            180                 185                 190

Ser Asp Ile Gln Met Thr Gln Ser Pro Ser Ser Leu Ser Ala Ser Val
        195                 200                 205

Gly Asp Arg Val Thr Ile Thr Cys Ser Ala Ser Gln Asp Ile Ser Asn
    210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285
```

```
Trp Thr Phe Gly Gln Gly Thr Lys Val Glu Ile Lys Arg Thr Val Ala
290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
                340                 345                 350

Gln Glu Ser Val Thr Glu Gln Asp Ser Lys Asp Ser Thr Tyr Ser Leu
                355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 44
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gly
    450                 455                 460

Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                485                 490                 495

Gly Lys Trp Tyr Val Val Gly Gln Ala Gly Asn Tyr Ile Leu Arg Glu
            500                 505                 510

Asp Lys Asp Pro Glu Lys Met Trp Ala Thr Ile Tyr Glu Leu Lys Glu
        515                 520                 525

Asp Lys Ser Tyr Asp Val Thr Gly Val Ser Phe Gly Pro Lys Lys Cys
    530                 535                 540

Asn Tyr Arg Ile Trp Thr Phe Val Pro Gly Ser Gln Pro Gly Glu Phe
545                 550                 555                 560

Thr Leu Gly Gly Ile Lys Ser Ser Pro Gly Gln Thr Ser Thr Leu Val
                565                 570                 575

Arg Val Val Ser Thr Asn Tyr Asn Gln His Ala Met Val Phe Phe Lys
            580                 585                 590

His Val Leu Gln Asn Arg Glu Phe Phe Glu Ile Thr Leu Tyr Gly Arg
        595                 600                 605

Thr Lys Glu Leu Thr Ser Glu Leu Lys Glu Asn Phe Ile Arg Phe Ser
    610                 615                 620

Lys Ser Leu Gly Leu Pro Glu Asn His Ile Val Phe Pro Val Pro Ile
625                 630                 635                 640

Asp Gln Cys Ile Asp Gly
                645
```

<210> SEQ ID NO 45
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Gln Ala Gly Asn Tyr Ile Leu Arg
            260                 265                 270

Glu Asp Lys Asp Pro Glu Lys Met Trp Ala Thr Ile Tyr Glu Leu Lys
        275                 280                 285

Glu Asp Lys Ser Tyr Asp Val Thr Gly Val Ser Phe Gly Pro Lys Lys
    290                 295                 300

Cys Asn Tyr Arg Ile Trp Thr Phe Val Pro Gly Ser Gln Pro Gly Glu
305                 310                 315                 320

Phe Thr Leu Gly Gly Ile Lys Ser Ser Pro Gly Gln Thr Ser Thr Leu
                325                 330                 335

Val Arg Val Val Ser Thr Asn Tyr Asn Gln His Ala Met Val Phe Phe
            340                 345                 350

Lys His Val Leu Gln Asn Arg Glu Phe Phe Glu Ile Thr Leu Tyr Gly
        355                 360                 365
```

```
Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 46
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 46

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Glu Lys Met Trp Ala Thr Ile Tyr Glu Leu Lys Glu Asp Lys Ser Tyr
50                  55                  60

Asp Val Thr Gly Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Ser Pro Gly Gln Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gly Ser Gly Gly Gly Gly Ser Gly Gly Gly Gly
            180                 185                 190

Ser Glu Val Gln Leu Val Glu Ser Gly Gly Leu Val Gln Pro Gly Gly
        195                 200                 205

Ser Leu Arg Leu Ser Cys Ala Ala Ser Gly Tyr Thr Phe Thr Asn
210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
            260                 265                 270

Tyr Leu Gln Met Asn Ser Leu Arg Ala Glu Asp Thr Ala Val Tyr Tyr
        275                 280                 285

Cys Ala Lys Tyr Pro His Tyr Tyr Gly Ser Ser His Trp Tyr Phe Asp
290                 295                 300

Val Trp Gly Gln Gly Thr Leu Val Thr Val Ser Ser Ala Ser Thr Lys
305                 310                 315                 320
```

```
Gly Pro Ser Val Phe Pro Leu Ala Pro Ser Ser Lys Ser Thr Ser Gly
            325                 330                 335

Gly Thr Ala Ala Leu Gly Cys Leu Val Lys Asp Tyr Phe Pro Glu Pro
        340                 345                 350

Val Thr Val Ser Trp Asn Ser Gly Ala Leu Thr Ser Gly Val His Thr
    355                 360                 365

Phe Pro Ala Val Leu Gln Ser Ser Gly Leu Tyr Ser Leu Ser Ser Val
370                 375                 380

Val Thr Val Pro Ser Ser Leu Gly Thr Gln Thr Tyr Ile Cys Asn
385                 390                 395                 400

Val Asn His Lys Pro Ser Asn Thr Lys Val Asp Lys Val Glu Pro
                405                 410                 415

Lys Ser Cys Asp Lys Thr His Thr Cys Pro Pro Cys Pro Ala Pro Glu
            420                 425                 430

Leu Leu Gly Gly Pro Ser Val Phe Leu Phe Pro Pro Lys Pro Lys Asp
        435                 440                 445

Thr Leu Met Ile Ser Arg Thr Pro Glu Val Thr Cys Val Val Val Asp
    450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
            500                 505                 510

Leu Asn Gly Lys Glu Tyr Lys Cys Lys Val Ser Asn Lys Ala Leu Pro
        515                 520                 525

Ala Pro Ile Glu Lys Thr Ile Ser Lys Ala Lys Gly Gln Pro Arg Glu
    530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
        595                 600                 605

Leu Thr Val Asp Lys Ser Arg Trp Gln Gln Gly Asn Val Phe Ser Cys
    610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 47
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

Val Val Gly Gln Ala Gly Asn Tyr Ile Leu Arg Glu Asp Lys Asp Pro
            35                  40                  45

Glu Lys Met Trp Ala Thr Ile Tyr Glu Leu Lys Glu Asp Lys Ser Tyr
 50                  55                  60

Asp Val Thr Gly Val Ser Phe Gly Pro Lys Lys Cys Asn Tyr Arg Ile
 65                  70                  75                  80

Trp Thr Phe Val Pro Gly Ser Gln Pro Gly Glu Phe Thr Leu Gly Gly
                 85                  90                  95

Ile Lys Ser Ser Pro Gly Gln Thr Ser Thr Leu Val Arg Val Val Ser
                100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
                180                 185                 190

Ser Asp Ile Gln Met Thr Gln Ser Pro Ser Ser Leu Ser Ala Ser Val
    195                 200                 205

Gly Asp Arg Val Thr Ile Thr Cys Ser Ala Ser Gln Asp Ile Ser Asn
    210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
                260                 265                 270

Pro Glu Asp Phe Ala Thr Tyr Tyr Cys Gln Gln Tyr Ser Thr Val Pro
    275                 280                 285

Trp Thr Phe Gly Gln Gly Thr Lys Val Glu Ile Lys Arg Thr Val Ala
    290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
                340                 345                 350

Gln Glu Ser Val Thr Glu Gln Asp Ser Lys Asp Ser Thr Tyr Ser Leu
            355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 48
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

-continued

```
                405                 410                 415
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Gly Gly Ser Gly Gly Gly Ser Gly
            450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                485                 490                 495

Gly Lys Trp Tyr Val Val Gly His Ala Gly Asn Tyr Ile Leu Arg Glu
            500                 505                 510

Asp Lys Asp Pro Glu Lys Met Trp Ala Thr Ile Tyr Glu Leu Lys Glu
            515                 520                 525

Asp Lys Ser Tyr Asp Val Thr Glu Val Ser Phe Gly Pro Lys Lys Cys
            530                 535                 540

Asn Tyr Arg Ile Trp Thr Phe Val Pro Gly Ser Gln Pro Gly Glu Phe
545                 550                 555                 560

Thr Leu Gly Gly Ile Lys Ser Pro Pro Gly Asp Thr Ser Thr Leu Val
                565                 570                 575

Arg Val Val Ser Thr Asn Tyr Asn Gln His Ala Met Val Phe Phe Lys
            580                 585                 590

His Val Leu Gln Asn Arg Glu Phe Phe Glu Ile Thr Leu Tyr Gly Arg
            595                 600                 605

Thr Lys Glu Leu Thr Ser Glu Leu Lys Glu Asn Phe Ile Arg Phe Ser
            610                 615                 620

Lys Ser Leu Gly Leu Pro Glu Asn His Ile Val Phe Pro Val Pro Ile
625                 630                 635                 640

Asp Gln Cys Ile Asp Gly
                645
```

<210> SEQ ID NO 49
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Gly Gly Ser Gly Gly Gly Gly Ser
    210                 215                 220
Gly Gly Gly Gly Ser Gln Asp Ser Thr Ser Asp Leu Ile Pro Ala Pro
225                 230                 235                 240
Pro Leu Ser Lys Val Pro Leu Gln Gln Asn Phe Gln Asp Asn Gln Phe
                245                 250                 255
His Gly Lys Trp Tyr Val Val Gly His Ala Gly Asn Tyr Ile Leu Arg
            260                 265                 270
Glu Asp Lys Asp Pro Glu Lys Met Trp Ala Thr Ile Tyr Glu Leu Lys
        275                 280                 285
Glu Asp Lys Ser Tyr Asp Val Thr Glu Val Ser Phe Gly Pro Lys Lys
    290                 295                 300
Cys Asn Tyr Arg Ile Trp Thr Phe Val Pro Gly Ser Gln Pro Gly Glu
305                 310                 315                 320
Phe Thr Leu Gly Gly Ile Lys Ser Pro Pro Gly Asp Thr Ser Thr Leu
                325                 330                 335
Val Arg Val Val Ser Thr Asn Tyr Asn Gln His Ala Met Val Phe Phe
            340                 345                 350
Lys His Val Leu Gln Asn Arg Glu Phe Phe Glu Ile Thr Leu Tyr Gly
        355                 360                 365
Arg Thr Lys Glu Leu Thr Ser Glu Leu Lys Glu Asn Phe Ile Arg Phe
    370                 375                 380
Ser Lys Ser Leu Gly Leu Pro Glu Asn His Ile Val Phe Pro Val Pro
385                 390                 395                 400
Ile Asp Gln Cys Ile Asp Gly
                405

<210> SEQ ID NO 50
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 50

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly His Ala Gly Asn Tyr Ile Leu Arg Glu Asp Lys Asp Pro
            35                  40                  45
Glu Lys Met Trp Ala Thr Ile Tyr Glu Leu Lys Glu Asp Lys Ser Tyr
        50                  55                  60
Asp Val Thr Glu Val Ser Phe Gly Pro Lys Lys Cys Asn Tyr Arg Ile
```

```
            65                  70                  75                  80
Trp Thr Phe Val Pro Gly Ser Gln Pro Gly Glu Phe Thr Leu Gly Gly
                    85                  90                  95
Ile Lys Ser Pro Pro Gly Asp Thr Ser Thr Leu Val Arg Val Val Ser
                    100                 105                 110
Thr Asn Tyr Asn Gln His Ala Met Val Phe Phe Lys His Val Leu Gln
                    115                 120                 125
Asn Arg Glu Phe Phe Glu Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                    165                 170                 175
Asp Gly Gly Gly Gly Ser Gly Gly Gly Ser Gly Gly Gly Gly
                    180                 185                 190
Ser Glu Val Gln Leu Val Glu Ser Gly Gly Leu Val Gln Pro Gly
                195                 200                 205
Gly Ser Leu Arg Leu Ser Cys Ala Ala Ser Gly Tyr Thr Phe Thr Asn
            210                 215                 220
Tyr Gly Met Asn Trp Val Arg Gln Ala Pro Gly Lys Gly Leu Glu Trp
225                 230                 235                 240
Val Gly Trp Ile Asn Thr Tyr Thr Gly Glu Pro Thr Tyr Ala Ala Asp
                    245                 250                 255
Phe Lys Arg Arg Phe Thr Phe Ser Leu Asp Thr Ser Lys Ser Thr Ala
                    260                 265                 270
Tyr Leu Gln Met Asn Ser Leu Arg Ala Glu Asp Thr Ala Val Tyr Tyr
                    275                 280                 285
Cys Ala Lys Tyr Pro His Tyr Tyr Gly Ser Ser His Trp Tyr Phe Asp
            290                 295                 300
Val Trp Gly Gln Gly Thr Leu Val Thr Val Ser Ser Ala Ser Thr Lys
305                 310                 315                 320
Gly Pro Ser Val Phe Pro Leu Ala Pro Ser Ser Lys Ser Thr Ser Gly
                    325                 330                 335
Gly Thr Ala Ala Leu Gly Cys Leu Val Lys Asp Tyr Phe Pro Glu Pro
                    340                 345                 350
Val Thr Val Ser Trp Asn Ser Gly Ala Leu Thr Ser Gly Val His Thr
                    355                 360                 365
Phe Pro Ala Val Leu Gln Ser Ser Gly Leu Tyr Ser Leu Ser Ser Val
            370                 375                 380
Val Thr Val Pro Ser Ser Ser Leu Gly Thr Gln Thr Tyr Ile Cys Asn
385                 390                 395                 400
Val Asn His Lys Pro Ser Asn Thr Lys Val Asp Lys Lys Val Glu Pro
                    405                 410                 415
Lys Ser Cys Asp Lys Thr His Thr Cys Pro Pro Cys Pro Ala Pro Glu
                    420                 425                 430
Leu Leu Gly Gly Pro Ser Val Phe Leu Phe Pro Pro Lys Pro Lys Asp
            435                 440                 445
Thr Leu Met Ile Ser Arg Thr Pro Glu Val Thr Cys Val Val Val Asp
            450                 455                 460
Val Ser His Glu Asp Pro Glu Val Lys Phe Asn Trp Tyr Val Asp Gly
465                 470                 475                 480
Val Glu Val His Asn Ala Lys Thr Lys Pro Arg Glu Glu Gln Tyr Asn
                    485                 490                 495
```

```
Ser Thr Tyr Arg Val Val Ser Val Leu Thr Val Leu His Gln Asp Trp
                500                 505                 510
Leu Asn Gly Lys Glu Tyr Lys Cys Lys Val Ser Asn Lys Ala Leu Pro
        515                 520                 525
Ala Pro Ile Glu Lys Thr Ile Ser Lys Ala Lys Gly Gln Pro Arg Glu
    530                 535                 540
Pro Gln Val Tyr Thr Leu Pro Pro Ser Arg Glu Glu Met Thr Lys Asn
545                 550                 555                 560
Gln Val Ser Leu Thr Cys Leu Val Lys Gly Phe Tyr Pro Ser Asp Ile
                565                 570                 575
Ala Val Glu Trp Glu Ser Asn Gly Gln Pro Glu Asn Asn Tyr Lys Thr
            580                 585                 590
Thr Pro Pro Val Leu Asp Ser Asp Gly Ser Phe Phe Leu Tyr Ser Lys
        595                 600                 605
Leu Thr Val Asp Lys Ser Arg Trp Gln Gln Gly Asn Val Phe Ser Cys
    610                 615                 620
Ser Val Met His Glu Ala Leu His Asn His Tyr Thr Gln Lys Ser Leu
625                 630                 635                 640
Ser Leu Ser Pro Gly Lys
                645

<210> SEQ ID NO 51
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 51

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly His Ala Gly Asn Tyr Ile Leu Arg Glu Asp Lys Asp Pro
        35                  40                  45
Glu Lys Met Trp Ala Thr Ile Tyr Glu Leu Lys Glu Asp Lys Ser Tyr
    50                  55                  60
Asp Val Thr Glu Val Ser Phe Gly Pro Lys Lys Cys Asn Tyr Arg Ile
65                  70                  75                  80
Trp Thr Phe Val Pro Gly Ser Gln Pro Gly Glu Phe Thr Leu Gly Gly
                85                  90                  95
Ile Lys Ser Pro Pro Gly Asp Thr Ser Thr Leu Val Arg Val Val Ser
            100                 105                 110
Thr Asn Tyr Asn Gln His Ala Met Val Phe Phe Lys His Val Leu Gln
        115                 120                 125
Asn Arg Glu Phe Phe Glu Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Gly Ser Gly Gly Gly Gly
            180                 185                 190
Ser Asp Ile Gln Met Thr Gln Ser Pro Ser Ser Leu Ser Ala Ser Val
        195                 200                 205
```

```
Gly Asp Arg Val Thr Ile Thr Cys Ser Ala Ser Gln Asp Ile Ser Asn
            210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285

Trp Thr Phe Gly Gln Gly Thr Lys Val Glu Ile Lys Arg Thr Val Ala
290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
            325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
        355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
            405

<210> SEQ ID NO 52
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

-continued

```
Thr Val Ser Trp Asn Ser Gly Ala Leu Thr Ser Gly Val His Thr Phe
            165                 170                 175
Pro Ala Val Leu Gln Ser Ser Gly Leu Tyr Ser Leu Ser Ser Val Val
        180                 185                 190
Thr Val Pro Ser Ser Ser Leu Gly Thr Gln Thr Tyr Ile Cys Asn Val
    195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys Gly Gly Gly Ser Gly Gly Gly Ser Gly
    450                 455                 460
Gly Gly Gly Ser Gln Asp Ser Thr Ser Asp Leu Ile Pro Ala Pro Pro
465                 470                 475                 480
Leu Ser Lys Val Pro Leu Gln Gln Asn Phe Gln Asp Asn Gln Phe His
                485                 490                 495
Gly Lys Trp Tyr Val Val Gly Gln Ala Gly Asn Tyr Ile Leu Arg Glu
            500                 505                 510
Asp Lys Asp Pro Gln Lys Met Trp Ala Thr Ile Tyr Glu Leu Lys Glu
        515                 520                 525
Asp Lys Ser Tyr Asp Val Thr Gly Val Ser Phe Gly Ala Lys Lys Cys
    530                 535                 540
Val Tyr Arg Ile Trp Thr Phe Val Pro Gly Ser Gln Pro Gly Glu Phe
545                 550                 555                 560
Thr Leu Gly Gly Ile Lys Ser Pro Pro Gly Gly Thr Ser Thr Leu Val
                565                 570                 575
```

Arg Val Val Ser Thr Asn Tyr Asn Gln His Ala Met Val Phe Phe Lys
            580                 585                 590

His Val Leu Gln Asn Arg Glu Phe Phe Glu Ile Thr Leu Tyr Gly Arg
        595                 600                 605

Thr Lys Glu Leu Thr Ser Glu Leu Lys Glu Asn Phe Ile Arg Phe Ser
    610                 615                 620

Lys Ser Leu Gly Leu Pro Glu Asn His Ile Val Phe Pro Val Pro Ile
625                 630                 635                 640

Asp Gln Cys Ile Asp Gly
            645

<210> SEQ ID NO 53
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Gln Ala Gly Asn Tyr Ile Leu Arg
            260                 265                 270

Glu Asp Lys Asp Pro Gln Lys Met Trp Ala Thr Ile Tyr Glu Leu Lys
        275                 280                 285

```
Glu Asp Lys Ser Tyr Asp Val Thr Gly Val Ser Phe Gly Ala Lys Lys
    290                 295                 300
Cys Val Tyr Arg Ile Trp Thr Phe Val Pro Gly Ser Gln Pro Gly Glu
305                 310                 315                 320
Phe Thr Leu Gly Gly Ile Lys Ser Pro Pro Gly Gly Thr Ser Thr Leu
                325                 330                 335
Val Arg Val Val Ser Thr Asn Tyr Asn Gln His Ala Met Val Phe Phe
            340                 345                 350
Lys His Val Leu Gln Asn Arg Glu Phe Phe Glu Ile Thr Leu Tyr Gly
        355                 360                 365
Arg Thr Lys Glu Leu Thr Ser Glu Leu Lys Glu Asn Phe Ile Arg Phe
370                 375                 380
Ser Lys Ser Leu Gly Leu Pro Glu Asn His Ile Val Phe Pro Val Pro
385                 390                 395                 400
Ile Asp Gln Cys Ile Asp Gly
                405

<210> SEQ ID NO 54
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 54

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Tyr Ile Leu Arg Glu Asp Lys Asp Pro
        35                  40                  45
Gln Lys Met Trp Ala Thr Ile Tyr Glu Leu Lys Glu Asp Lys Ser Tyr
    50                  55                  60
Asp Val Thr Gly Val Ser Phe Gly Ala Lys Lys Cys Val Tyr Arg Ile
65                  70                  75                  80
Trp Thr Phe Val Pro Gly Ser Gln Pro Gly Glu Phe Thr Leu Gly Gly
                85                  90                  95
Ile Lys Ser Pro Pro Gly Gly Thr Ser Thr Leu Val Arg Val Val Ser
            100                 105                 110
Thr Asn Tyr Asn Gln His Ala Met Val Phe Phe Lys His Val Leu Gln
        115                 120                 125
Asn Arg Glu Phe Phe Glu Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Gly Ser Gly Gly Gly Gly Ser Gly Gly Gly Gly
            180                 185                 190
Ser Glu Val Gln Leu Val Glu Ser Gly Gly Leu Val Gln Pro Gly
        195                 200                 205
Gly Ser Leu Arg Leu Ser Cys Ala Ala Ser Gly Tyr Thr Phe Thr Asn
    210                 215                 220
Tyr Gly Met Asn Trp Val Arg Gln Ala Pro Gly Lys Gly Leu Glu Trp
225                 230                 235                 240
```

```
Val Gly Trp Ile Asn Thr Tyr Thr Gly Glu Pro Thr Tyr Ala Ala Asp
                    245                 250                 255
Phe Lys Arg Arg Phe Thr Phe Ser Leu Asp Thr Ser Lys Ser Thr Ala
            260                 265                 270
Tyr Leu Gln Met Asn Ser Leu Arg Ala Glu Asp Thr Ala Val Tyr Tyr
            275                 280                 285
Cys Ala Lys Tyr Pro His Tyr Tyr Gly Ser Ser His Trp Tyr Phe Asp
            290                 295                 300
Val Trp Gly Gln Gly Thr Leu Val Thr Val Ser Ala Ser Thr Lys
305                 310                 315                 320
Gly Pro Ser Val Phe Pro Leu Ala Pro Ser Ser Lys Ser Thr Ser Gly
                325                 330                 335
Gly Thr Ala Ala Leu Gly Cys Leu Val Lys Asp Tyr Phe Pro Glu Pro
                340                 345                 350
Val Thr Val Ser Trp Asn Ser Gly Ala Leu Thr Ser Gly Val His Thr
                355                 360                 365
Phe Pro Ala Val Leu Gln Ser Ser Gly Leu Tyr Ser Leu Ser Ser Val
            370                 375                 380
Val Thr Val Pro Ser Ser Ser Leu Gly Thr Gln Thr Tyr Ile Cys Asn
385                 390                 395                 400
Val Asn His Lys Pro Ser Asn Thr Lys Val Asp Lys Val Glu Pro
                405                 410                 415
Lys Ser Cys Asp Lys Thr His Thr Cys Pro Pro Cys Pro Ala Pro Glu
                420                 425                 430
Leu Leu Gly Gly Pro Ser Val Phe Leu Phe Pro Pro Lys Pro Lys Asp
            435                 440                 445
Thr Leu Met Ile Ser Arg Thr Pro Glu Val Thr Cys Val Val Val Asp
            450                 455                 460
Val Ser His Glu Asp Pro Glu Val Lys Phe Asn Trp Tyr Val Asp Gly
465                 470                 475                 480
Val Glu Val His Asn Ala Lys Thr Lys Pro Arg Glu Glu Gln Tyr Asn
                485                 490                 495
Ser Thr Tyr Arg Val Val Ser Val Leu Thr Val Leu His Gln Asp Trp
            500                 505                 510
Leu Asn Gly Lys Glu Tyr Lys Cys Lys Val Ser Asn Lys Ala Leu Pro
            515                 520                 525
Ala Pro Ile Glu Lys Thr Ile Ser Lys Ala Lys Gly Gln Pro Arg Glu
            530                 535                 540
Pro Gln Val Tyr Thr Leu Pro Pro Ser Arg Glu Glu Met Thr Lys Asn
545                 550                 555                 560
Gln Val Ser Leu Thr Cys Leu Val Lys Gly Phe Tyr Pro Ser Asp Ile
                565                 570                 575
Ala Val Glu Trp Glu Ser Asn Gly Gln Pro Glu Asn Asn Tyr Lys Thr
            580                 585                 590
Thr Pro Pro Val Leu Asp Ser Asp Gly Ser Phe Phe Leu Tyr Ser Lys
            595                 600                 605
Leu Thr Val Asp Lys Ser Arg Trp Gln Gln Gly Asn Val Phe Ser Cys
            610                 615                 620
Ser Val Met His Glu Ala Leu His Asn His Tyr Thr Gln Lys Ser Leu
625                 630                 635                 640
Ser Leu Ser Pro Gly Lys
                645
```

-continued

```
<210> SEQ ID NO 55
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 55
```

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                      45

Gln Lys Met Trp Ala Thr Ile Tyr Glu Leu Lys Glu Asp Lys Ser Tyr
    50                  55                  60

Asp Val Thr Gly Val Ser Phe Gly Ala Lys Lys Cys Val Tyr Arg Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Gly Ser Gly Gly Gly Gly
            180                 185                 190

Ser Asp Ile Gln Met Thr Gln Ser Pro Ser Ser Leu Ser Ala Ser Val
        195                 200                 205

Gly Asp Arg Val Thr Ile Thr Cys Ser Ala Ser Gln Asp Ile Ser Asn
210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285

Trp Thr Phe Gly Gln Gly Thr Lys Val Glu Ile Lys Arg Thr Val Ala
    290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
        355                 360                 365

Ser Ser Thr Leu Thr Leu Ser Lys Ala Asp Tyr Glu Lys His Lys Val

```
                370               375               380
Tyr Ala Cys Glu Val Thr His Gln Gly Leu Ser Ser Pro Val Thr Lys
385               390               395               400

Ser Phe Asn Arg Gly Glu Cys
                405

<210> SEQ ID NO 56
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                    325                 330                 335
Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gly
    450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                485                 490                 495

Gly Lys Trp Tyr Val Val Gly Gln Ala Gly Asn Tyr Ile Leu Arg Glu
            500                 505                 510

Asp Lys Asp Pro Val Lys Met Trp Ala Thr Ile Tyr Glu Leu Lys Glu
        515                 520                 525

Asp Lys Ser Tyr Asp Val Thr Glu Val Ser Phe Gly Pro Lys Lys Cys
    530                 535                 540

Asn Tyr Arg Ile Trp Thr Phe Val Pro Gly Ser Gln Pro Gly Glu Phe
545                 550                 555                 560

Thr Leu Gly Gly Ile Lys Ser Leu Pro Gly Gly Thr Ser Thr Leu Val
                565                 570                 575

Arg Val Val Ser Thr Asn Tyr Asn Gln His Ala Met Val Phe Phe Lys
            580                 585                 590

His Val Leu Gln Asn Arg Glu Phe Phe Glu Ile Thr Leu Tyr Gly Arg
        595                 600                 605

Thr Lys Glu Leu Thr Ser Glu Leu Lys Glu Asn Phe Ile Arg Phe Ser
    610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 57
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
```

```
            35                  40                  45
Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Gln Ala Gly Asn Tyr Ile Leu Arg
            260                 265                 270

Glu Asp Lys Asp Pro Val Lys Met Trp Ala Thr Ile Tyr Glu Leu Lys
        275                 280                 285

Glu Asp Lys Ser Tyr Asp Val Thr Glu Val Ser Phe Gly Pro Lys Lys
    290                 295                 300

Cys Asn Tyr Arg Ile Trp Thr Phe Val Pro Gly Ser Gln Pro Gly Glu
305                 310                 315                 320

Phe Thr Leu Gly Gly Ile Lys Ser Leu Pro Gly Gly Thr Ser Thr Leu
                325                 330                 335

Val Arg Val Val Ser Thr Asn Tyr Asn Gln His Ala Met Val Phe Phe
            340                 345                 350

Lys His Val Leu Gln Asn Arg Glu Phe Phe Glu Ile Thr Leu Tyr Gly
        355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405
```

<210> SEQ ID NO 58
<211> LENGTH: 646
<212> TYPE: PRT
<213> ORGANISM: Artificial Sequence
<220> FEATURE:
<223> OTHER INFORMATION: hNGAL fusion protein

```
<400> SEQUENCE: 58

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Val Lys Met Trp Ala Thr Ile Tyr Glu Leu Lys Glu Asp Lys Ser Tyr
    50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Leu Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Glu Val Gln Leu Val Glu Ser Gly Gly Gly Leu Val Gln Pro Gly
    195                 200                 205

Gly Ser Leu Arg Leu Ser Cys Ala Ala Ser Gly Tyr Thr Phe Thr Asn
    210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
            260                 265                 270

Tyr Leu Gln Met Asn Ser Leu Arg Ala Glu Asp Thr Ala Val Tyr Tyr
        275                 280                 285

Cys Ala Lys Tyr Pro His Tyr Tyr Gly Ser Ser His Trp Tyr Phe Asp
    290                 295                 300

Val Trp Gly Gln Gly Thr Leu Val Thr Val Ser Ser Ala Ser Thr Lys
305                 310                 315                 320

Gly Pro Ser Val Phe Pro Leu Ala Pro Ser Ser Lys Ser Thr Ser Gly
                325                 330                 335

Gly Thr Ala Ala Leu Gly Cys Leu Val Lys Asp Tyr Phe Pro Glu Pro
            340                 345                 350

Val Thr Val Ser Trp Asn Ser Gly Ala Leu Thr Ser Gly Val His Thr
        355                 360                 365

Phe Pro Ala Val Leu Gln Ser Ser Gly Leu Tyr Ser Leu Ser Ser Val
    370                 375                 380

Val Thr Val Pro Ser Ser Ser Leu Gly Thr Gln Thr Tyr Ile Cys Asn
385                 390                 395                 400

Val Asn His Lys Pro Ser Asn Thr Lys Val Asp Lys Lys Val Glu Pro
                405                 410                 415
```

```
Lys Ser Cys Asp Lys Thr His Thr Cys Pro Pro Cys Pro Ala Pro Glu
                420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
        450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
            500                 505                 510

Leu Asn Gly Lys Glu Tyr Lys Cys Lys Val Ser Asn Lys Ala Leu Pro
        515                 520                 525

Ala Pro Ile Glu Lys Thr Ile Ser Lys Ala Lys Gly Gln Pro Arg Glu
530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
        595                 600                 605

Leu Thr Val Asp Lys Ser Arg Trp Gln Gln Gly Asn Val Phe Ser Cys
610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 59
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 59

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Val Lys Met Trp Ala Thr Ile Tyr Glu Leu Lys Glu Asp Lys Ser Tyr
    50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Leu Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125
```

Asn Arg Glu Phe Phe Glu Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
                180                 185                 190

Ser Asp Ile Gln Met Thr Gln Ser Pro Ser Ser Leu Ser Ala Ser Val
            195                 200                 205

Gly Asp Arg Val Thr Ile Thr Cys Ser Ala Ser Gln Asp Ile Ser Asn
        210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285

Trp Thr Phe Gly Gln Gly Thr Lys Val Glu Ile Lys Arg Thr Val Ala
290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
        355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 60
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Lys Gly Gly Gly Gly Ser Gly Gly Gly Gly Ser Gly
    450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                485                 490                 495
```

```
Gly Lys Trp Tyr Val Gly Val Ala Gly Asn Trp Tyr Leu Arg Glu
            500                 505                 510

Asp Lys Asp Pro Ile Lys Met Thr Ala Thr Ile Tyr Glu Leu Lys Glu
            515                 520                 525

Asp Lys Ser Tyr Asp Val Thr Gln Val Gly Phe Glu Gln Glu Lys Cys
            530                 535                 540

Lys Tyr Ser Ile His Thr Phe Val Pro Gly Ser Gln Pro Gly Glu Phe
545                 550                 555                 560

Thr Leu Gly Asn Ile Lys Ser Trp Pro Gly Asp Thr Ser Pro Leu Val
                565                 570                 575

Arg Val Val Ser Thr Asn Tyr Asp Gln His Ala Met Val Phe Phe Lys
                580                 585                 590

Gly Val Met Gln Asp Arg Glu Val Phe Ala Ile Thr Leu Tyr Gly Arg
                595                 600                 605

Thr Lys Glu Leu Thr Ser Glu Leu Lys Glu Asn Phe Ile Arg Phe Ser
            610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 61
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Gly Gly Gly Ser Gly Gly Gly Ser
    210             215                 220

Gly Gly Gly Gly Ser Gln Asp Ser Thr Ser Asp Leu Ile Pro Ala Pro
225             230                 235                 240

Pro Leu Ser Lys Val Pro Leu Gln Gln Asn Phe Gln Asp Asn Gln Phe
                245                 250                 255

His Gly Lys Trp Tyr Val Val Gly Val Ala Gly Asn Trp Tyr Leu Arg
            260                 265                 270

Glu Asp Lys Asp Pro Ile Lys Met Thr Ala Thr Ile Tyr Glu Leu Lys
        275                 280                 285

Glu Asp Lys Ser Tyr Asp Val Thr Gln Val Gly Phe Glu Gln Glu Lys
290                 295                 300

Cys Lys Tyr Ser Ile His Thr Phe Val Pro Gly Ser Gln Pro Gly Glu
305                 310                 315                 320

Phe Thr Leu Gly Asn Ile Lys Ser Trp Pro Gly Asp Thr Ser Pro Leu
                325                 330                 335

Val Arg Val Val Ser Thr Asn Tyr Asp Gln His Ala Met Val Phe Phe
            340                 345                 350

Lys Gly Val Met Gln Asp Arg Glu Val Phe Ala Ile Thr Leu Tyr Gly
        355                 360                 365

Arg Thr Lys Glu Leu Thr Ser Glu Leu Lys Glu Asn Phe Ile Arg Phe
370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 62
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 62

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Trp Tyr Leu Arg Glu Asp Lys Asp Pro
            35                  40                  45

Ile Lys Met Thr Ala Thr Ile Tyr Glu Leu Lys Glu Asp Lys Ser Tyr
        50                  55                  60

Asp Val Thr Gln Val Gly Phe Glu Gln Glu Lys Cys Lys Tyr Ser Ile
65                  70                  75                  80

His Thr Phe Val Pro Gly Ser Gln Pro Gly Glu Phe Thr Leu Gly Asn
                85                  90                  95

Ile Lys Ser Trp Pro Gly Asp Thr Ser Pro Leu Val Arg Val Val Ser
            100                 105                 110

Thr Asn Tyr Asp Gln His Ala Met Val Phe Phe Lys Gly Val Met Gln
        115                 120                 125

Asp Arg Glu Val Phe Ala Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160
```

```
Leu Pro Glu Asn His Ile Val Phe Pro Val Pro Ile Asp Gln Cys Ile
                165                 170                 175
Asp Gly Gly Gly Gly Ser Gly Gly Gly Ser Gly Gly Gly Gly
            180                 185                 190
Ser Glu Val Gln Leu Val Glu Ser Gly Gly Leu Val Gln Pro Gly
            195                 200                 205
Gly Ser Leu Arg Leu Ser Cys Ala Ala Ser Gly Tyr Thr Phe Thr Asn
            210                 215                 220
Tyr Gly Met Asn Trp Val Arg Gln Ala Pro Lys Gly Leu Glu Trp
225                 230                 235                 240
Val Gly Trp Ile Asn Thr Tyr Thr Gly Glu Pro Thr Tyr Ala Ala Asp
                245                 250                 255
Phe Lys Arg Arg Phe Thr Phe Ser Leu Asp Thr Ser Lys Ser Thr Ala
                260                 265                 270
Tyr Leu Gln Met Asn Ser Leu Arg Ala Glu Asp Thr Ala Val Tyr Tyr
                275                 280                 285
Cys Ala Lys Tyr Pro His Tyr Tyr Gly Ser Ser His Trp Tyr Phe Asp
                290                 295                 300
Val Trp Gly Gln Gly Thr Leu Val Thr Val Ser Ser Ala Ser Thr Lys
305                 310                 315                 320
Gly Pro Ser Val Phe Pro Leu Ala Pro Ser Ser Lys Ser Thr Ser Gly
                325                 330                 335
Gly Thr Ala Ala Leu Gly Cys Leu Val Lys Asp Tyr Phe Pro Glu Pro
                340                 345                 350
Val Thr Val Ser Trp Asn Ser Gly Ala Leu Thr Ser Gly Val His Thr
                355                 360                 365
Phe Pro Ala Val Leu Gln Ser Ser Gly Leu Tyr Ser Leu Ser Ser Val
                370                 375                 380
Val Thr Val Pro Ser Ser Ser Leu Gly Thr Gln Thr Tyr Ile Cys Asn
385                 390                 395                 400
Val Asn His Lys Pro Ser Asn Thr Lys Val Asp Lys Lys Val Glu Pro
                405                 410                 415
Lys Ser Cys Asp Lys Thr His Thr Cys Pro Pro Cys Pro Ala Pro Glu
                420                 425                 430
Leu Leu Gly Gly Pro Ser Val Phe Leu Phe Pro Pro Lys Pro Lys Asp
                435                 440                 445
Thr Leu Met Ile Ser Arg Thr Pro Glu Val Thr Cys Val Val Val Asp
                450                 455                 460
Val Ser His Glu Asp Pro Glu Val Lys Phe Asn Trp Tyr Val Asp Gly
465                 470                 475                 480
Val Glu Val His Asn Ala Lys Thr Lys Pro Arg Glu Glu Gln Tyr Asn
                485                 490                 495
Ser Thr Tyr Arg Val Val Ser Val Leu Thr Val Leu His Gln Asp Trp
                500                 505                 510
Leu Asn Gly Lys Glu Tyr Lys Cys Lys Val Ser Asn Lys Ala Leu Pro
                515                 520                 525
Ala Pro Ile Glu Lys Thr Ile Ser Lys Ala Lys Gly Gln Pro Arg Glu
                530                 535                 540
Pro Gln Val Tyr Thr Leu Pro Pro Ser Arg Glu Met Thr Lys Asn
545                 550                 555                 560
Gln Val Ser Leu Thr Cys Leu Val Lys Gly Phe Tyr Pro Ser Asp Ile
                565                 570                 575
Ala Val Glu Trp Glu Ser Asn Gly Gln Pro Glu Asn Asn Tyr Lys Thr
```

```
                  580             585             590
Thr Pro Pro Val Leu Asp Ser Asp Gly Ser Phe Phe Leu Tyr Ser Lys
            595             600             605

Leu Thr Val Asp Lys Ser Arg Trp Gln Gln Gly Asn Val Phe Ser Cys
            610             615             620

Ser Val Met His Glu Ala Leu His Asn His Tyr Thr Gln Lys Ser Leu
625             630             635             640

Ser Leu Ser Pro Gly Lys
                645

<210> SEQ ID NO 63
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 63

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Trp Tyr Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asp Val Thr Gln Val Gly Phe Glu Gln Glu Lys Cys Lys Tyr Ser Ile
65                  70                  75                  80

His Thr Phe Val Pro Gly Ser Gln Pro Gly Glu Phe Thr Leu Gly Asn
                85                  90                  95

Ile Lys Ser Trp Pro Gly Asp Thr Ser Pro Leu Val Arg Val Val Ser
            100                 105                 110

Thr Asn Tyr Asp Gln His Ala Met Val Phe Phe Lys Gly Val Met Gln
        115                 120                 125

Asp Arg Glu Val Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Asp Ile Gln Met Thr Gln Ser Pro Ser Ser Leu Ser Ala Ser Val
        195                 200                 205

Gly Asp Arg Val Thr Ile Thr Cys Ser Ala Ser Gln Asp Ile Ser Asn
    210                 215                 220

Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285

Trp Thr Phe Gly Gln Gly Thr Lys Val Glu Ile Lys Arg Thr Val Ala
```

```
            290                 295                 300
Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
                340                 345                 350

Gln Glu Ser Val Thr Glu Gln Asp Ser Lys Asp Ser Thr Tyr Ser Leu
            355                 360                 365

Ser Ser Thr Leu Thr Leu Ser Lys Ala Asp Tyr Glu Lys His Lys Val
        370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 64
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
```

```
            245                 250                 255
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                    325                 330                 335

Pro Ile Glu Lys Thr Ile Ser Lys Ala Lys Gly Gln Pro Arg Glu Pro
                    340                 345                 350

Gln Val Tyr Thr Leu Pro Pro Ser Arg Glu Glu Met Thr Lys Asn Gln
                    355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                    405                 410                 415

Thr Val Asp Lys Ser Arg Trp Gln Gln Gly Asn Val Phe Ser Cys Ser
                    420                 425                 430

Val Met His Glu Ala Leu His Asn His Tyr Thr Gln Lys Ser Leu Ser
            435                 440                 445

Leu Ser Pro Gly Lys Gly Gly Gly Ser Gly Gly Gly Ser Gly
450                 455                 460

Gly Gly Gly Ser Gln Asp Ser Thr Ser Asp Leu Ile Pro Ala Pro Pro
465                 470                 475                 480

Leu Ser Lys Val Pro Leu Gln Gln Asn Phe Gln Asp Asn Gln Phe His
                    485                 490                 495

Gly Lys Trp Tyr Val Val Gly Val Ala Gly Asn Trp Tyr Leu Arg Glu
                    500                 505                 510

Asp Lys Asp Pro Ile Lys Met Thr Ala Thr Ile Tyr Glu Leu Lys Glu
            515                 520                 525

Asp Lys Ser Tyr Asp Val Thr Gln Val Gly Phe Glu Gln Glu Lys Cys
530                 535                 540

Lys Tyr Ser Ile His Thr Phe Val Pro Gly Ser Gln Pro Gly Glu Phe
545                 550                 555                 560

Thr Leu Gly Asp Ile Lys Ser Trp Pro Gly Asp Thr Ser Pro Leu Val
                    565                 570                 575

Arg Val Val Ser Thr Asn Tyr Asn Gln His Ala Met Val Phe Phe Lys
            580                 585                 590

Gly Met Met Gln Asp Arg Glu Val Phe Ala Ile Thr Leu Tyr Gly Arg
                    595                 600                 605

Thr Lys Glu Leu Thr Ser Glu Leu Lys Glu Asn Phe Ile Arg Phe Ser
610                 615                 620

Lys Ser Leu Gly Leu Pro Glu Asn His Ile Val Phe Pro Val Pro Ile
625                 630                 635                 640

Asp Gln Cys Ile Asp Gly
                    645

<210> SEQ ID NO 65
```

<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Val Ala Gly Asn Trp Tyr Leu Arg
            260                 265                 270

Glu Asp Lys Asp Pro Ile Lys Met Thr Ala Thr Ile Tyr Glu Leu Lys
        275                 280                 285

Glu Asp Lys Ser Tyr Asp Val Thr Gln Val Gly Phe Glu Gln Glu Lys
    290                 295                 300

Cys Lys Tyr Ser Ile His Thr Phe Val Pro Gly Ser Gln Pro Gly Glu
305                 310                 315                 320

Phe Thr Leu Gly Asp Ile Lys Ser Trp Pro Gly Asp Thr Ser Pro Leu
                325                 330                 335

Val Arg Val Val Ser Thr Asn Tyr Asn Gln His Ala Met Val Phe Phe
            340                 345                 350

Lys Gly Met Met Gln Asp Arg Glu Val Phe Ala Ile Thr Leu Tyr Gly
        355                 360                 365

Arg Thr Lys Glu Leu Thr Ser Glu Leu Lys Glu Asn Phe Ile Arg Phe
    370                 375                 380
```

-continued

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 66
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 66

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Trp Tyr Leu Arg Glu Asp Lys Asp Pro
            35                  40                  45

Ile Lys Met Thr Ala Thr Ile Tyr Glu Leu Lys Glu Asp Lys Ser Tyr
        50                  55                  60

Asn Val Thr Gln Val Gly Phe Glu Gln Glu Lys Cys Lys Tyr Ser Ile
65                  70                  75                  80

His Thr Phe Val Pro Gly Ser Gln Pro Gly Glu Phe Thr Leu Gly Asp
                85                  90                  95

Ile Lys Ser Trp Pro Gly Asp Thr Ser Pro Leu Val Arg Val Val Ser
            100                 105                 110

Thr Asn Tyr Asn Gln His Ala Met Val Phe Phe Lys Gly Met Met Gln
        115                 120                 125

Asp Arg Glu Val Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Glu Val Gln Leu Val Glu Ser Gly Gly Gly Leu Val Gln Pro Gly
    195                 200                 205

Gly Ser Leu Arg Leu Ser Cys Ala Ala Ser Gly Tyr Thr Phe Thr Asn
    210                 215                 220

Tyr Gly Met Asn Trp Val Arg Gln Ala Pro Gly Lys Gly Leu Glu Trp
225                 230                 235                 240

Val Gly Trp Ile Asn Thr Tyr Thr Gly Glu Pro Thr Tyr Ala Ala Asp
                245                 250                 255

Phe Lys Arg Arg Phe Thr Phe Ser Leu Asp Thr Ser Lys Ser Thr Ala
            260                 265                 270

Tyr Leu Gln Met Asn Ser Leu Arg Ala Glu Asp Thr Ala Val Tyr Tyr
        275                 280                 285

Cys Ala Lys Tyr Pro His Tyr Tyr Gly Ser Ser His Trp Tyr Phe Asp
    290                 295                 300

Val Trp Gly Gln Gly Thr Leu Val Thr Val Ser Ser Ala Ser Thr Lys
305                 310                 315                 320

Gly Pro Ser Val Phe Pro Leu Ala Pro Ser Ser Lys Ser Thr Ser Gly
                325                 330                 335

```
Gly Thr Ala Ala Leu Gly Cys Leu Val Lys Asp Tyr Phe Pro Glu Pro
                340                 345                 350

Val Thr Val Ser Trp Asn Ser Gly Ala Leu Thr Ser Gly Val His Thr
            355                 360                 365

Phe Pro Ala Val Leu Gln Ser Ser Gly Leu Tyr Ser Leu Ser Ser Val
        370                 375                 380

Val Thr Val Pro Ser Ser Leu Gly Thr Gln Thr Tyr Ile Cys Asn
385                 390                 395                 400

Val Asn His Lys Pro Ser Asn Thr Lys Val Asp Lys Lys Val Glu Pro
                405                 410                 415

Lys Ser Cys Asp Lys Thr His Thr Cys Pro Pro Cys Pro Ala Pro Glu
                420                 425                 430

Leu Leu Gly Gly Pro Ser Val Phe Leu Phe Pro Pro Lys Pro Lys Asp
                435                 440                 445

Thr Leu Met Ile Ser Arg Thr Pro Glu Val Thr Cys Val Val Val Asp
                450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
                500                 505                 510

Leu Asn Gly Lys Glu Tyr Lys Cys Lys Val Ser Asn Lys Ala Leu Pro
                515                 520                 525

Ala Pro Ile Glu Lys Thr Ile Ser Lys Ala Lys Gly Gln Pro Arg Glu
                530                 535                 540

Pro Gln Val Tyr Thr Leu Pro Pro Ser Arg Glu Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
                580                 585                 590

Thr Pro Pro Val Leu Asp Ser Asp Gly Ser Phe Phe Leu Tyr Ser Lys
                595                 600                 605

Leu Thr Val Asp Lys Ser Arg Trp Gln Gln Gly Asn Val Phe Ser Cys
                610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 67
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 67

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Trp Tyr Leu Arg Glu Asp Lys Asp Pro
            35                  40                  45
```

```
Ile Lys Met Thr Ala Thr Ile Tyr Glu Leu Lys Glu Asp Lys Ser Tyr
 50                  55                  60
Asp Val Thr Gln Val Gly Phe Glu Gln Lys Cys Lys Tyr Ser Ile
 65                  70                  75                  80
His Thr Phe Val Pro Gly Ser Gln Pro Gly Glu Phe Thr Leu Gly Asp
                 85                  90                  95
Ile Lys Ser Trp Pro Gly Asp Thr Ser Pro Leu Val Arg Val Val Ser
                100                 105                 110
Thr Asn Tyr Asn Gln His Ala Met Val Phe Phe Lys Gly Met Met Gln
            115                 120                 125
Asp Arg Glu Val Phe Ala Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Ser Gly Gly Gly Gly
            180                 185                 190
Ser Asp Ile Gln Met Thr Gln Ser Pro Ser Ser Leu Ser Ala Ser Val
            195                 200                 205
Gly Asp Arg Val Thr Ile Thr Cys Ser Ala Ser Gln Asp Ile Ser Asn
        210                 215                 220
Tyr Leu Asn Trp Tyr Gln Gln Lys Pro Gly Lys Ala Pro Lys Val Leu
225                 230                 235                 240
Ile Tyr Phe Thr Ser Ser Leu His Ser Gly Val Pro Ser Arg Phe Ser
                245                 250                 255
Gly Ser Gly Ser Gly Thr Asp Phe Thr Leu Thr Ile Ser Ser Leu Gln
            260                 265                 270
Pro Glu Asp Phe Ala Thr Tyr Tyr Cys Gln Gln Tyr Ser Thr Val Pro
        275                 280                 285
Trp Thr Phe Gly Gln Gly Thr Lys Val Glu Ile Lys Arg Thr Val Ala
    290                 295                 300
Ala Pro Ser Val Phe Ile Phe Pro Pro Ser Asp Glu Gln Leu Lys Ser
305                 310                 315                 320
Gly Thr Ala Ser Val Val Cys Leu Leu Asn Asn Phe Tyr Pro Arg Glu
                325                 330                 335
Ala Lys Val Gln Trp Lys Val Asp Asn Ala Leu Gln Ser Gly Asn Ser
            340                 345                 350
Gln Glu Ser Val Thr Glu Gln Asp Ser Lys Asp Ser Thr Tyr Ser Leu
        355                 360                 365
Ser Ser Thr Leu Thr Leu Ser Lys Ala Asp Tyr Glu Lys His Lys Val
370                 375                 380
Tyr Ala Cys Glu Val Thr His Gln Gly Leu Ser Ser Pro Val Thr Lys
385                 390                 395                 400
Ser Phe Asn Arg Gly Glu Cys
                405

<210> SEQ ID NO 68
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 68
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Gly Ser Gly
450                 455                 460

Gly Gly Gly Ser Gln Asp Ser Thr Ser Asp Leu Ile Pro Ala Pro Pro
465             470                 475                 480

Leu Ser Lys Val Pro Leu Gln Gln Asn Phe Gln Asp Asn Gln Phe His
                485                 490                 495

Gly Lys Trp Tyr Val Val Gly Met Ala Gly Asn Trp Asp Leu Arg Glu
            500                 505                 510

Asp Lys Asp Pro Ile Lys Met Thr Ala Thr Ile Tyr Glu Leu Lys Glu
        515                 520                 525

Asp Lys Ser Tyr Asp Val Thr Gln Val Ala Phe Glu Gln Lys Lys Cys
    530                 535                 540

Lys Tyr Ser Ile His Thr Phe Val Pro Gly Ser Gln Pro Gly Glu Phe
545                 550                 555                 560

Thr Leu Gly Gln Ile Lys Ser Trp Pro Gly Asp Thr Ser Pro Leu Val
                565                 570                 575

Arg Val Val Ser Thr Asn Tyr Asn Gln His Ala Met Val Phe Phe Lys
            580                 585                 590

Gly Val Met Gln Asn Arg Glu Val Phe Ala Ile Thr Leu Tyr Gly Arg
        595                 600                 605

Thr Lys Glu Leu Thr Ser Glu Leu Lys Glu Asn Phe Ile Arg Phe Ser
    610                 615                 620

Lys Ser Leu Gly Leu Pro Glu Asn His Ile Val Phe Pro Val Pro Ile
625                 630                 635                 640

Asp Gln Cys Ile Asp Gly
                645

<210> SEQ ID NO 69
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Met Ala Gly Asn Trp Asp Leu Arg
            260                 265                 270

Glu Asp Lys Asp Pro Ile Lys Met Thr Ala Thr Ile Tyr Glu Leu Lys
        275                 280                 285

Glu Asp Lys Ser Tyr Asp Val Thr Gln Val Ala Phe Glu Gln Lys Lys
    290                 295                 300

Cys Lys Tyr Ser Ile His Thr Phe Val Pro Gly Ser Gln Pro Gly Glu
305                 310                 315                 320

Phe Thr Leu Gly Gln Ile Lys Ser Trp Pro Gly Asp Thr Ser Pro Leu
                325                 330                 335

Val Arg Val Val Ser Thr Asn Tyr Asn Gln His Ala Met Val Phe Phe
            340                 345                 350

Lys Gly Val Met Gln Asn Arg Glu Val Phe Ala Ile Thr Leu Tyr Gly
        355                 360                 365

Arg Thr Lys Glu Leu Thr Ser Glu Leu Lys Glu Asn Phe Ile Arg Phe
    370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 70
<211> LENGTH: 646
<212> TYPE: PRT
<213> ORGANISM: Artificial Sequence
<220> FEATURE:
<223> OTHER INFORMATION: hNGAL fusion protein

<400> SEQUENCE: 70

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Met Ala Gly Asn Trp Asp Leu Arg Glu Asp Lys Asp Pro
            35                  40                  45

Ile Lys Met Thr Ala Thr Ile Tyr Glu Leu Lys Glu Asp Lys Ser Tyr
        50                  55                  60

Asp Val Thr Gln Val Ala Phe Glu Gln Lys Lys Cys Lys Tyr Ser Ile
65                  70                  75                  80
```

-continued

```
His Thr Phe Val Pro Gly Ser Gln Pro Gly Glu Phe Thr Leu Gly Gln
                 85                  90                  95
Ile Lys Ser Trp Pro Gly Asp Thr Ser Pro Leu Val Arg Val Val Ser
            100                 105                 110
Thr Asn Tyr Asn Gln His Ala Met Val Phe Phe Lys Gly Val Met Gln
        115                 120                 125
Asn Arg Glu Val Phe Ala Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Ser Gly Gly Gly Gly
            180                 185                 190
Ser Glu Val Gln Leu Val Glu Ser Gly Gly Gly Leu Val Gln Pro Gly
        195                 200                 205
Gly Ser Leu Arg Leu Ser Cys Ala Ala Ser Gly Tyr Thr Phe Thr Asn
    210                 215                 220
Tyr Gly Met Asn Trp Val Arg Gln Ala Pro Gly Lys Gly Leu Glu Trp
225                 230                 235                 240
Val Gly Trp Ile Asn Thr Tyr Thr Gly Glu Pro Thr Tyr Ala Ala Asp
                245                 250                 255
Phe Lys Arg Arg Phe Thr Phe Ser Leu Asp Thr Ser Lys Ser Thr Ala
            260                 265                 270
Tyr Leu Gln Met Asn Ser Leu Arg Ala Glu Asp Thr Ala Val Tyr Tyr
        275                 280                 285
Cys Ala Lys Tyr Pro His Tyr Tyr Gly Ser Ser His Trp Tyr Phe Asp
    290                 295                 300
Val Trp Gly Gln Gly Thr Leu Val Thr Val Ser Ser Ala Ser Thr Lys
305                 310                 315                 320
Gly Pro Ser Val Phe Pro Leu Ala Pro Ser Ser Lys Ser Thr Ser Gly
                325                 330                 335
Gly Thr Ala Ala Leu Gly Cys Leu Val Lys Asp Tyr Phe Pro Glu Pro
            340                 345                 350
Val Thr Val Ser Trp Asn Ser Gly Ala Leu Thr Ser Gly Val His Thr
        355                 360                 365
Phe Pro Ala Val Leu Gln Ser Ser Gly Leu Tyr Ser Leu Ser Ser Val
    370                 375                 380
Val Thr Val Pro Ser Ser Ser Leu Gly Thr Gln Thr Tyr Ile Cys Asn
385                 390                 395                 400
Val Asn His Lys Pro Ser Asn Thr Lys Val Asp Lys Lys Val Glu Pro
                405                 410                 415
Lys Ser Cys Asp Lys Thr His Thr Cys Pro Pro Cys Pro Ala Pro Glu
            420                 425                 430
Leu Leu Gly Gly Pro Ser Val Phe Leu Phe Pro Pro Lys Pro Lys Asp
        435                 440                 445
Thr Leu Met Ile Ser Arg Thr Pro Glu Val Thr Cys Val Val Val Asp
    450                 455                 460
Val Ser His Glu Asp Pro Glu Val Lys Phe Asn Trp Tyr Val Asp Gly
465                 470                 475                 480
Val Glu Val His Asn Ala Lys Thr Lys Pro Arg Glu Glu Gln Tyr Asn
                485                 490                 495
Ser Thr Tyr Arg Val Val Ser Val Leu Thr Val Leu His Gln Asp Trp
```

```
              500                 505                 510
Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
        530                 535                 540

Pro Gln Val Tyr Thr Leu Pro Pro Ser Arg Glu Met Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
        595                 600                 605

Leu Thr Val Asp Lys Ser Arg Trp Gln Gln Gly Asn Val Phe Ser Cys
    610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 71
<211> LENGTH: 407
<212> TYPE: PRT
<213> ORGANISM: Artificial Sequence
<220> FEATURE:
<223> OTHER INFORMATION: hNGAL fusion protein

<400> SEQUENCE: 71

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Trp Asp Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asp Val Thr Gln Val Ala Phe Glu Gln Lys Lys Cys Lys Tyr Ser Ile
65                  70                  75                  80

His Thr Phe Val Pro Gly Ser Gln Pro Gly Glu Phe Thr Leu Gly Gln
                85                  90                  95

Ile Lys Ser Trp Pro Gly Asp Thr Ser Pro Leu Val Arg Val Val Ser
            100                 105                 110

Thr Asn Tyr Asn Gln His Ala Met Val Phe Phe Lys Gly Val Met Gln
        115                 120                 125

Asn Arg Glu Val Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Asp Ile Gln Met Thr Gln Ser Pro Ser Ser Leu Ser Ala Ser Val
        195                 200                 205

Gly Asp Arg Val Thr Ile Thr Cys Ser Ala Ser Gln Asp Ile Ser Asn
```

```
                     210                 215                 220
Tyr Leu Asn Trp Tyr Gln Gln Lys Pro Gly Lys Ala Pro Lys Val Leu
225                 230                 235                 240

Ile Tyr Phe Thr Ser Ser Leu His Ser Gly Val Pro Ser Arg Phe Ser
                245                 250                 255

Gly Ser Gly Ser Gly Thr Asp Phe Thr Leu Thr Ile Ser Ser Leu Gln
            260                 265                 270

Pro Glu Asp Phe Ala Thr Tyr Tyr Cys Gln Gln Tyr Ser Thr Val Pro
        275                 280                 285

Trp Thr Phe Gly Gln Gly Thr Lys Val Glu Ile Lys Arg Thr Val Ala
    290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
        355                 360                 365

Ser Ser Thr Leu Thr Leu Ser Lys Ala Asp Tyr Glu Lys His Lys Val
    370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 72
<211> LENGTH: 534
<212> TYPE: DNA
<213> ORGANISM: Artificial Sequence
<220> FEATURE:
<223> OTHER INFORMATION: hNGAL mutein

<400> SEQUENCE: 72
caggactcca cctcagacct gatcccagcc ccacctctga gcaaggtccc tctgcagcag      60
aacttccagg acaaccaatt ccatgggaaa tggtatgtcg tgggccaagc cggaaattac     120
atcctgcgtg aggataagga tccgggaaaa atgtgggcga ccatttacga gttgaaagaa     180
gataaatcat ataacgtcac cggagtgagc tttggaccta agaaatgcaa ttacaccatt     240
tggacctttg tgccggggag ccagccgggc gagtttactt taggcggaat taaaagtcct     300
ccgggcggaa catcaacctt ggtccgcgtc gtgagcacca actacaacca gcatgccatg     360
gtgttcttca gcacgtgctg cagaaccgcg agttctttg agatcacact gtacgggcgc     420
acgaaagaac tgacaagcga gctgaaggaa aattttatcc gcttttccaa atctctgggc     480
ctccctgaaa accacatcgt cttccctgtc caatcgacc agtgtatcga cggc           534

<210> SEQ ID NO 73
<211> LENGTH: 534
<212> TYPE: DNA
<213> ORGANISM: Artificial Sequence
<220> FEATURE:
<223> OTHER INFORMATION: hNGAL mutein

<400> SEQUENCE: 73
caggactcca cctcagacct gatcccagcc ccacctctga gcaaggtccc tctgcagcag      60
aacttccagg acaaccaatt ccatgggaaa tggtatgtcg tgggcttcgc cggaaatcac     120
```
cgtctgcgtg aggataagga tccgggaaaa atgcacgcga ccatttacga gttgaaagaa    180
gataaatcat ataacgtcac cgacgtgacc tttgcattca agaaatgcaa ttaccgtatt    240
cacacctttg tgccggggag ccagccgggc gagtttactt taggcaatat taaaagttgg    300
ccgggcgaga catcaacctt ggtccgcgtc gtgagcacca actacaacca gcatgccatg    360
gtgttcttca agaccgtgat gcagaaccgc gagtggtttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc    534

```
<210> SEQ ID NO 74
<211> LENGTH: 534
<212> TYPE: DNA
<213> ORGANISM: Artificial Sequence
<220> FEATURE:
<223> OTHER INFORMATION: hNGAL mutein
```

<400> SEQUENCE: 74
caggactcca cctcagacct gatcccagcc ccacctctga gcaaggtccc tctgcagcag    60
aacttccagg acaaccaatt ccatgggaaa tggtatgtcg tgggcgttgc cggaaattgg    120
tacctgcgtg aggataagga tccgatcaaa atgaccgcga ccatttacga gttgaaagaa    180
gataaatcat ataacgtcac ccaagtggga tttgagcaaa agaaatgcaa atacagcatt    240
cacacctttg tgccggggag ccagccgggc gagtttactt taggcgacat taaaagttgg    300
ccgggcgaca catcactgtt ggtccgcgtc gtgagcacca actacaacca gcatgccatg    360
gtgttcttca agggagtgat gcagaaccgc gaggtttttg caatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc    534

```
<210> SEQ ID NO 75
<211> LENGTH: 534
<212> TYPE: DNA
<213> ORGANISM: Artificial Sequence
<220> FEATURE:
<223> OTHER INFORMATION: hNGAL mutein
```

<400> SEQUENCE: 75
caggactcca cctcagacct gatcccagcc ccacctctga gcaaggtccc tctgcagcag    60
aacttccagg acaaccaatt ccatgggaaa tggtatgtcg tgggcgaggc cggaaatgtt    120
gagctgcgtg aggataagga tccggttaaa atgaccgcga ccatttacga gttgaaagaa    180
gataaatcat ataacgtcac cgaggtgcgt ttttggctga agaaatgcaa atacaatatt    240
cacacctttg tgccggggag ccagccgggc gagtttactt taggcgcaat taaaagtgga    300
ccgggcatga catcaacctt ggtccgcgtc gtgagcacca actacaacca gcatgccatg    360
gtgttcttca agaccgtgat gcagaaccgc gagtggtttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc    534

```
<210> SEQ ID NO 76
<211> LENGTH: 534
<212> TYPE: DNA
<213> ORGANISM: Artificial Sequence
<220> FEATURE:
<223> OTHER INFORMATION: hNGAL mutein
```

<400> SEQUENCE: 76

```
caggactcca cctcagacct gatcccagcc ccacctctga gcaaggtccc tctgcagcag    60
aacttccagg acaaccaatt ccatgggaaa tggtatgtcg tgggccaagc cggaaattac   120
tggctgcgtg aggataagga tccgatcaaa atgtctgcga ccatttacga gttgaaagaa   180
gataaatcat ataacgtcac catcgtgtac tttacccgta agaaatgcag ctaccgtatt   240
tacacctttg tgccggggag ccagccgggc gagtttactt taggccctat taaaagttac   300
ccgggcgaca catcaacctt ggtccgcgtc gtgagcacca actacaacca gcatgccatg   360
gtgttcttca agcacgtgta ccagaaccgc gagtggtttg agatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

<210> SEQ ID NO 77
<211> LENGTH: 534
<212> TYPE: DNA
<213> ORGANISM: Artificial Sequence
<220> FEATURE:
<223> OTHER INFORMATION: hNGAL mutein

<400> SEQUENCE: 77

```
caggactcca cctcagacct gatcccagcc ccacctctga gcaaggtccc tctgcagcag    60
aacttccagg acaaccaatt ccatgggaaa tggtacgtag ttgggcaggc cggaaattat   120
attctgcgtg aggataagga tccggagaaa atgtgggcga ccatttacga gttgaaagaa   180
gataaatcat atgacgtcac cggggtgtcg tttgggccta agaaatgcaa ttacaggatt   240
tggacctttg tgccggggag ccagccgggc gagtttactt taggcgggat taaaagttct   300
ccgggctaga catcaacgtt ggtccgcgtc gtgagcacca actacaacca gcatgccatg   360
gtgttcttca agcatgtgct tcagaaccgc gagttttttg agatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

<210> SEQ ID NO 78
<211> LENGTH: 534
<212> TYPE: DNA
<213> ORGANISM: Artificial Sequence
<220> FEATURE:
<223> OTHER INFORMATION: hNGAL mutein

<400> SEQUENCE: 78

```
caggactcca cctcagacct gatcccagcc ccacctctga gcaaggtccc tctgcagcag    60
aacttccagg acaaccaatt ccatgggaaa tggtacgtag ttgggcatgc cggaaattat   120
attctgcgtg aggataagga tccggagaaa atgtgggcga ccatttacga gttgaaagaa   180
gataaatcat atgacgtcac cgaggtgtct tttgggccga agaaatgcaa ttacaggatt   240
tggacctttg tgccggggag ccagccgggc gagtttactt taggcggtat taaaagtcct   300
ccgggcgata catcaacgtt ggtccgcgtc gtgagcacca actacaacca gcatgccatg   360
gtgttcttca agcatgtgct tcagaaccgc gagttttttg agatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

<210> SEQ ID NO 79
<211> LENGTH: 534

```
<212> TYPE: DNA
<213> ORGANISM: Artificial Sequence
<220> FEATURE:
<223> OTHER INFORMATION: hNGAL mutein

<400> SEQUENCE: 79
caggactcca cctcagacct gatcccagcc ccacctctga gcaaggtccc tctgcagcag      60
aacttccagg acaaccaatt ccatgggaaa tggtacgtag ttgggcaggc cggaaattat     120
attctgcgtg aggataagga tccggggaaa atgtgggcga ccatttacga gttgaaagaa     180
gataaatcat atgacgtcac cgaggtgtcg tttgggcta agaaatgcaa ttacaggatt      240
tggacctttg tgccggggag ccagccgggc gagtttactt taggcggtat taaaagtgat     300
ccgggcggga catcaacgtt ggtccgcgtc gtgagcacca actacaacca gcatgccatg     360
gtgttcttca gcatgtgct tcagaaccgc gagttttttg agatcacact gtacgggcgc      420
acgaaagaac tgacaagcga gctgaaggaa aatttatcc gcttttccaa atctctgggc      480
ctcccctgaaa accacatcgt cttccctgtc ccaatcgacc agtgtatcga cggc          534

<210> SEQ ID NO 80
<211> LENGTH: 534
<212> TYPE: DNA
<213> ORGANISM: Artificial Sequence
<220> FEATURE:
<223> OTHER INFORMATION: hNGAL mutein

<400> SEQUENCE: 80
caggactcca cctcagacct gatcccagcc ccacctctga gcaaggtccc tctgcagcag      60
aacttccagg acaaccaatt ccatgggaaa tggtacgtag ttgggcatgc cggaaattat     120
attctgcgtg aggataagga tccggggaaa atgtgggcga ccatttacga gttgaaagaa     180
gataaatcat atgacgtcac cgaggtgtct tttgggccta agaaatgcaa ttacaggatt     240
tggacctttg tgccggggag ccagccgggc gagtttactt taggcggtat taaaagtccg     300
ccgggcggta catcaacgtt ggtccgcgtc gtgagcacca actacaacca gcatgccatg     360
gtgttcttca gcatgtgct tcagaaccgc gagttttttg agatcacact gtacgggcgc      420
acgaaagaac tgacaagcga gctgaaggaa aatttatcc gcttttccaa atctctgggc      480
ctcccctgaaa accacatcgt cttccctgtc ccaatcgacc agtgtatcga cggc          534

<210> SEQ ID NO 81
<211> LENGTH: 534
<212> TYPE: DNA
<213> ORGANISM: Artificial Sequence
<220> FEATURE:
<223> OTHER INFORMATION: hNGAL mutein

<400> SEQUENCE: 81
caggactcca cctcagacct gatcccagcc ccacctctga gcaaggtccc tctgcagcag      60
aacttccagg acaaccaatt ccatgggaaa tggtacgtag ttgggcaggc cggaaattat     120
attctgcgtg aggataagga tccgtagaaa atgtgggcga ccatttacga gttgaaagaa     180
gataaatcat atgacgtcac cggtgtgtct tttgggccta agaaatgcgt ttacaggatt     240
tggacctttg tgccggggag ccagccgggc gagtttactt taggcggtat taaaagtccg     300
ccgggcggta catcaacgtt ggtccgcgtc gtgagcacca actacaacca gcatgccatg     360
gtgttcttca gcatgtgct tcagaaccgc gagttttttg agatcacact gtacgggcgc      420
acgaaagaac tgacaagcga gctgaaggaa aatttatcc gcttttccaa atctctgggc      480
```

```
ctccctgaaa accacatcgt cttccctgtc ccaatcgacc agtgtatcga cggc      534
```

<210> SEQ ID NO 82
<211> LENGTH: 534
<212> TYPE: DNA
<213> ORGANISM: Artificial Sequence
<220> FEATURE:
<223> OTHER INFORMATION: hNGAL mutein

<400> SEQUENCE: 82

```
caggactcca cctcagacct gatcccagcc ccacctctga gcaaggtccc tctgcagcag   60
aacttccagg acaaccaatt ccatgggaaa tggtacgtag ttgggcaggc cggaaattat  120
attctgcgtg aggataagga tccggttaaa atgtgggcga ccatttacga gttgaaagaa  180
gataaatcat atgacgtcac cgaggtgtct tttggtccta agaaatgcaa ttacaggatt  240
tggacctttg tgccggggag ccagccgggc gagtttactt taggcgggat taaaagtctt  300
ccgggcggta catcaacttt ggtccgcgtc gtgagcacca actacaacca gcatgccatg  360
gtgttcttca agcatgtgct tcagaaccgc gagttttttg agatcacact gtacgggcgc  420
acgaaagaac tgacaagcga gctgaaggaa aattttatcc gcttttccaa atctctgggc  480
ctccctgaaa accacatcgt cttccctgtc ccaatcgacc agtgtatcga cggc         534
```

<210> SEQ ID NO 83
<211> LENGTH: 534
<212> TYPE: DNA
<213> ORGANISM: Artificial Sequence
<220> FEATURE:
<223> OTHER INFORMATION: hNGAL mutein

<400> SEQUENCE: 83

```
caggactcca cctcagacct gatcccagcc ccacctctga gcaaggtccc tctgcagcag   60
aacttccagg acaaccaatt ccatgggaaa tggtatgtcg tgggcgttgc cggaaattgg  120
tacctgcgtg aggataagga tccgatcaaa atgaccgcga ccatttacga gttgaaagaa  180
gataaatcat atgacgtcac ccaagtggga tttgagcaag agaaatgcaa atacagcatt  240
cacacctttg tgccggggag ccagccgggc gagtttactt taggcaacat taaaagttgg  300
ccgggcgaca catcaccgtt ggtccgcgtc gtgagcacca actacgacca gcatgccatg  360
gtgttcttca agggagtgat gcaggatcgc gaggttttt gcaatcacact gtacgggcgc  420
acgaaagaac tgacaagcga gctgaaggaa aattttatcc gcttttccaa atctctgggc  480
ctccctgaaa accacatcgt cttccctgtc ccaatcgacc agtgtatcga cggc         534
```

<210> SEQ ID NO 84
<211> LENGTH: 534
<212> TYPE: DNA
<213> ORGANISM: Artificial Sequence
<220> FEATURE:
<223> OTHER INFORMATION: hNGAL mutein

<400> SEQUENCE: 84

```
caggactcca cctcagacct gatcccagcc ccacctctga gcaaggtccc tctgcagcag   60
aacttccagg acaaccaatt ccatgggaaa tggtatgtcg tgggcgttgc cggaaattgg  120
tacctgcgtg aggataagga tccgatcaaa atgaccgcga ccatttacga gttgaaagaa  180
gataaatcat atgacgtcac ccaagtggga tttgagcaag agaaatgcaa atacagcatt  240
cacacctttg tgccggggag ccagccgggc gagtttactt taggcgacat taagagttgg  300
ccgggcgaca catcaccgtt ggtccgcgtc gtgagcacca actacaacca gcatgccatg  360
```

```
gtgttcttca agggaatgat gcaggaccgc gaggttttg caatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 85
<211> LENGTH: 534
<212> TYPE: DNA
<213> ORGANISM: Artificial Sequence
<220> FEATURE:
<223> OTHER INFORMATION: hNGAL mutein

<400> SEQUENCE: 85

```
caggactcca cctcagacct gatcccagcc ccacctctga gcaaggtccc tctgcagcag      60
aacttccagg acaaccaatt ccatgggaaa tggtacgtag taggtatggc cggaaattgg     120
gatctgcgtg aggataagga tccgattaaa atgacggcga ccatttacga gttgaaagaa     180
gataaatcat atgacgtcac ccaggtggcg tttgagcaga gaaatgcaa gtactcgatt      240 catacctttg tgccggggag ccagccgggc gagtttactt taggctagat taaaagttgg     300
ccgggcgata catcaccttt ggtccgcgtc gtgagcacca actacaacca gcatgccatg     360
gtgttcttca aggggggtgat gcagaaccgc gaggtgtttg ctatcacact gtacgggcgc    420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 86
<211> LENGTH: 178
<212> TYPE: PRT
<213> ORGANISM: Artificial Sequence
<220> FEATURE:
<223> OTHER INFORMATION: hNGAL mutein

<400> SEQUENCE: 86

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Gly Lys Met Trp Ala Thr Ile Tyr Glu Leu Lys Glu Asp Lys Ser Tyr
    50                  55                  60

Asn Val Thr Gly Val Ser Phe Gly Pro Lys Lys Cys Asn Tyr Thr Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 87
<211> LENGTH: 178
<212> TYPE: PRT
<213> ORGANISM: Artificial Sequence
<220> FEATURE:
<223> OTHER INFORMATION: hNGAL mutein

<400> SEQUENCE: 87

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Phe Ala Gly Asn His Arg Leu Arg Glu Asp Lys Asp Pro
        35                  40                  45
Gly Lys Met His Ala Thr Ile Tyr Glu Leu Lys Glu Asp Lys Ser Tyr
    50                  55                  60
Asn Val Thr Asp Val Thr Phe Ala Phe Lys Lys Cys Asn Tyr Arg Ile
65                  70                  75                  80
His Thr Phe Val Pro Gly Ser Gln Pro Gly Glu Phe Thr Leu Gly Asn
                85                  90                  95
Ile Lys Ser Trp Pro Gly Glu Thr Ser Thr Leu Val Arg Val Val Ser
            100                 105                 110
Thr Asn Tyr Asn Gln His Ala Met Val Phe Phe Lys Thr Val Met Gln
        115                 120                 125
Asn Arg Glu Trp Phe Trp Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 88
<211> LENGTH: 178
<212> TYPE: PRT
<213> ORGANISM: Artificial Sequence
<220> FEATURE:
<223> OTHER INFORMATION: hNGAL mutein

<400> SEQUENCE: 88

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Val Ala Gly Asn Trp Tyr Leu Arg Glu Asp Lys Asp Pro
        35                  40                  45
Ile Lys Met Thr Ala Thr Ile Tyr Glu Leu Lys Glu Asp Lys Ser Tyr
    50                  55                  60
Asn Val Thr Gln Val Gly Phe Glu Gln Lys Lys Cys Lys Tyr Ser Ile
65                  70                  75                  80
His Thr Phe Val Pro Gly Ser Gln Pro Gly Glu Phe Thr Leu Gly Asp
                85                  90                  95
Ile Lys Ser Trp Pro Gly Asp Thr Ser Leu Leu Val Arg Val Val Ser
            100                 105                 110
Thr Asn Tyr Asn Gln His Ala Met Val Phe Phe Lys Gly Val Met Gln
        115                 120                 125
```

```
Asn Arg Glu Val Phe Ala Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 89
<211> LENGTH: 178
<212> TYPE: PRT
<213> ORGANISM: Artificial Sequence
<220> FEATURE:
<223> OTHER INFORMATION: hNGAL mutein

<400> SEQUENCE: 89

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Glu Ala Gly Asn Val Glu Leu Arg Glu Asp Lys Asp Pro
            35                  40                  45

Val Lys Met Thr Ala Thr Ile Tyr Glu Leu Lys Glu Asp Lys Ser Tyr
50                  55                  60

Asn Val Thr Glu Val Arg Phe Trp Leu Lys Lys Cys Lys Tyr Asn Ile
65                  70                  75                  80

His Thr Phe Val Pro Gly Ser Gln Pro Gly Glu Phe Thr Leu Gly Ala
                85                  90                  95

Ile Lys Ser Gly Pro Gly Met Thr Ser Thr Leu Val Arg Val Val Ser
            100                 105                 110

Thr Asn Tyr Asn Gln His Ala Met Val Phe Phe Lys Thr Val Met Gln
                115                 120                 125

Asn Arg Glu Trp Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 90
<211> LENGTH: 178
<212> TYPE: PRT
<213> ORGANISM: Artificial Sequence
<220> FEATURE:
<223> OTHER INFORMATION: hNGAL mutein

<400> SEQUENCE: 90

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Tyr Trp Leu Arg Glu Asp Lys Asp Pro
            35                  40                  45

Ile Lys Met Ser Ala Thr Ile Tyr Glu Leu Lys Glu Asp Lys Ser Tyr
50                  55                  60
```

```
Asn Val Thr Ile Val Tyr Phe Thr Arg Lys Lys Cys Ser Tyr Arg Ile
 65                  70                  75                  80

Tyr Thr Phe Val Pro Gly Ser Gln Pro Gly Glu Phe Thr Leu Gly Pro
                 85                  90                  95

Ile Lys Ser Tyr Pro Gly Asp Thr Ser Thr Leu Val Arg Val Val Ser
                100                 105                 110

Thr Asn Tyr Asn Gln His Ala Met Val Phe Phe Lys His Val Tyr Gln
            115                 120                 125

Asn Arg Glu Trp Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 91
<211> LENGTH: 178
<212> TYPE: PRT
<213> ORGANISM: Artificial Sequence
<220> FEATURE:
<223> OTHER INFORMATION: hNGAL mutein

<400> SEQUENCE: 91

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Gln Ala Gly Asn Tyr Ile Leu Arg Glu Asp Lys Asp Pro
         35                  40                  45

Glu Lys Met Trp Ala Thr Ile Tyr Glu Leu Lys Glu Asp Lys Ser Tyr
 50                  55                  60

Asp Val Thr Gly Val Ser Phe Gly Pro Lys Lys Cys Asn Tyr Arg Ile
 65                  70                  75                  80

Trp Thr Phe Val Pro Gly Ser Gln Pro Gly Glu Phe Thr Leu Gly Gly
                 85                  90                  95

Ile Lys Ser Ser Pro Gly Gln Thr Ser Thr Leu Val Arg Val Val Ser
                100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 92
<211> LENGTH: 178
<212> TYPE: PRT
<213> ORGANISM: Artificial Sequence
<220> FEATURE:
<223> OTHER INFORMATION: hNGAL mutein

<400> SEQUENCE: 92

```
Gln Asp Ser Thr Ser Asp Leu Ile Pro Ala Pro Pro Leu Ser Lys Val
```

```
        1               5                  10                 15
    Pro Leu Gln Gln Asn Phe Gln Asp Asn Gln Phe His Gly Lys Trp Tyr
                    20                  25                  30

Val Val Gly His Ala Gly Asn Tyr Ile Leu Arg Glu Asp Lys Asp Pro
                    35                  40                  45

Glu Lys Met Trp Ala Thr Ile Tyr Glu Leu Lys Glu Asp Lys Ser Tyr
                50                  55                  60

Asp Val Thr Glu Val Ser Phe Gly Pro Lys Lys Cys Asn Tyr Arg Ile
    65                  70                  75                  80

Trp Thr Phe Val Pro Gly Ser Gln Pro Gly Glu Phe Thr Leu Gly Gly
                    85                  90                  95

Ile Lys Ser Pro Pro Gly Asp Thr Ser Thr Leu Val Arg Val Val Ser
                    100                 105                 110

Thr Asn Tyr Asn Gln His Ala Met Val Phe Phe Lys His Val Leu Gln
                    115                 120                 125

Asn Arg Glu Phe Phe Glu Ile Thr Leu Tyr Gly Arg Thr Lys Glu Leu
                    130                 135                 140

Thr Ser Glu Leu Lys Glu Asn Phe Ile Arg Phe Ser Lys Ser Leu Gly
    145                 150                 155                 160

Leu Pro Glu Asn His Ile Val Phe Pro Val Pro Ile Asp Gln Cys Ile
                    165                 170                 175

Asp Gly

<210> SEQ ID NO 93
<211> LENGTH: 178
<212> TYPE: PRT
<213> ORGANISM: Artificial Sequence
<220> FEATURE:
<223> OTHER INFORMATION: hNGAL mutein

<400> SEQUENCE: 93

Gln Asp Ser Thr Ser Asp Leu Ile Pro Ala Pro Pro Leu Ser Lys Val
    1               5                   10                  15

Pro Leu Gln Gln Asn Phe Gln Asp Asn Gln Phe His Gly Lys Trp Tyr
                    20                  25                  30

Val Val Gly Gln Ala Gly Asn Tyr Ile Leu Arg Glu Asp Lys Asp Pro
                    35                  40                  45

Gln Lys Met Trp Ala Thr Ile Tyr Glu Leu Lys Glu Asp Lys Ser Tyr
                50                  55                  60

Asp Val Thr Gly Val Ser Phe Gly Ala Lys Lys Cys Val Tyr Arg Ile
    65                  70                  75                  80

Trp Thr Phe Val Pro Gly Ser Gln Pro Gly Glu Phe Thr Leu Gly Gly
                    85                  90                  95

Ile Lys Ser Pro Pro Gly Gly Thr Ser Thr Leu Val Arg Val Val Ser
                    100                 105                 110

Thr Asn Tyr Asn Gln His Ala Met Val Phe Phe Lys His Val Leu Gln
                    115                 120                 125

Asn Arg Glu Phe Phe Glu Ile Thr Leu Tyr Gly Arg Thr Lys Glu Leu
                    130                 135                 140

Thr Ser Glu Leu Lys Glu Asn Phe Ile Arg Phe Ser Lys Ser Leu Gly
    145                 150                 155                 160

Leu Pro Glu Asn His Ile Val Phe Pro Val Pro Ile Asp Gln Cys Ile
                    165                 170                 175

Asp Gly
```

<210> SEQ ID NO 94
<211> LENGTH: 178
<212> TYPE: PRT
<213> ORGANISM: Artificial Sequence
<220> FEATURE:
<223> OTHER INFORMATION: hNGAL mutein

<400> SEQUENCE: 94

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Val Lys Met Trp Ala Thr Ile Tyr Glu Leu Lys Glu Asp Lys Ser Tyr
    50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Leu Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 95
<211> LENGTH: 178
<212> TYPE: PRT
<213> ORGANISM: Artificial Sequence
<220> FEATURE:
<223> OTHER INFORMATION: hNGAL mutein

<400> SEQUENCE: 95

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Trp Tyr Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asp Val Thr Gln Val Gly Phe Glu Gln Glu Lys Cys Lys Tyr Ser Ile
65                  70                  75                  80

His Thr Phe Val Pro Gly Ser Gln Pro Gly Glu Phe Thr Leu Gly Asn
                85                  90                  95

Ile Lys Ser Trp Pro Gly Asp Thr Ser Pro Leu Val Arg Val Val Ser
            100                 105                 110

Thr Asn Tyr Asp Gln His Ala Met Val Phe Phe Lys Gly Val Met Gln
        115                 120                 125

Asp Arg Glu Val Phe Ala Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 96
<211> LENGTH: 178
<212> TYPE: PRT
<213> ORGANISM: Artificial Sequence
<220> FEATURE:
<223> OTHER INFORMATION: hNGAL mutein

<400> SEQUENCE: 96

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Trp Tyr Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asp Val Thr Gln Val Gly Phe Glu Gln Glu Lys Cys Lys Tyr Ser Ile
65                  70                  75                  80

His Thr Phe Val Pro Gly Ser Gln Pro Gly Glu Phe Thr Leu Gly Asp
                85                  90                  95

Ile Lys Ser Trp Pro Gly Asp Thr Ser Pro Leu Val Arg Val Val Ser
            100                 105                 110

Thr Asn Tyr Asn Gln His Ala Met Val Phe Phe Lys Gly Met Met Gln
        115                 120                 125

Asp Arg Glu Val Phe Ala Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 97
<211> LENGTH: 178
<212> TYPE: PRT
<213> ORGANISM: Artificial Sequence
<220> FEATURE:
<223> OTHER INFORMATION: hNGAL mutein

<400> SEQUENCE: 97

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Trp Asp Leu Arg Glu Asp Lys Asp Pro
        35                  40                  45

Ile Lys Met Thr Ala Thr Ile Tyr Glu Leu Lys Glu Asp Lys Ser Tyr
    50                  55                  60

Asp Val Thr Gln Val Ala Phe Glu Gln Lys Lys Cys Lys Tyr Ser Ile

-continued

```
        65                  70                  75                  80
His Thr Phe Val Pro Gly Ser Gln Pro Gly Glu Phe Thr Leu Gly Gln
                85                  90                  95
Ile Lys Ser Trp Pro Gly Asp Thr Ser Pro Leu Val Arg Val Val Ser
                100                 105                 110
Thr Asn Tyr Asn Gln His Ala Met Val Phe Phe Lys Gly Val Met Gln
                115                 120                 125
Asn Arg Glu Val Phe Ala Ile Thr Leu Tyr Gly Arg Thr Lys Glu Leu
                130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

UNITED STATES PATENT AND TRADEMARK OFFICE
CERTIFICATE OF CORRECTION

PATENT NO. : 10,703,810 B2
APPLICATION NO. : 15/777340
DATED : July 7, 2020
INVENTOR(S) : Shane Olwill et al.

Page 1 of 1

It is certified that error appears in the above-identified patent and that said Letters Patent is hereby corrected as shown below:

In the Claims

In Claim 7, Column 250, Line 42, replace "Tyr 52 Thr" with --Tyr 52→Thr--.

In Claim 7, Column 250, Line 59, replace "Tyr 52 Trp" with --Tyr 52→Trp--.

In Claim 7, Column 250, Line 65, replace "Tyr 52 Trp" with --Tyr 52→Trp--.

In Claim 7, Column 251, Line 4, replace "Tyr 52 Trp" with --Tyr 52→Trp--.

In Claim 7, Column 251, Line 9, replace "Tyr 52 Trp" with --Tyr 52→Trp--.

In Claim 7, Column 251, Line 15, replace "Tyr 52 Trp" with --Tyr 52→Trp--.

In Claim 7, Column 251, Line 21, replace "Tyr 52 Trp" with --Tyr 52→Trp--.

In Claim 7, Column 251, Line 28, replace "Tyr 52 Thr" with --Tyr 52→Thr--.

In Claim 7, Column 251, Line 35, replace "Tyr 52 Thr" with --Tyr 52→Thr--.

Signed and Sealed this
Ninth Day of March, 2021

Drew Hirshfeld
*Performing the Functions and Duties of the
Under Secretary of Commerce for Intellectual Property and
Director of the United States Patent and Trademark Office*